(12) United States Patent
Scheller et al.

(10) Patent No.: US 11,497,518 B2
(45) Date of Patent: Nov. 15, 2022

(54) ULTRASONIC SURGICAL HANDPIECE

(71) Applicant: Kogent Surgical, LLC, Chesterfield, MO (US)

(72) Inventors: Gregg D Scheller, Wildwood, MO (US); Steven J Apperson, Ballwin, MO (US); Johanna L Bryan, Chesterfield, MO (US); David G Wuchinich, Bronx, NY (US)

( * ) Notice: Subject to any disclaimer, the term of this patent is extended or adjusted under 35 U.S.C. 154(b) by 862 days.

(21) Appl. No.: 16/405,732

(22) Filed: May 7, 2019

(65) Prior Publication Data
US 2019/0336161 A1 Nov. 7, 2019

Related U.S. Application Data

(60) Provisional application No. 62/667,892, filed on May 7, 2018.

(51) Int. Cl.
*A61B 17/32* (2006.01)

(52) U.S. Cl.
CPC ............. *A61B 17/320068* (2013.01); *A61B 2017/32007* (2017.08); *A61B 2017/320071* (2017.08); *A61B 2017/320084* (2013.01)

(58) Field of Classification Search
CPC .. A61B 17/320068; A61B 2017/32007; A61B 2017/320071; A61B 2017/320084
See application file for complete search history.

(56) References Cited

U.S. PATENT DOCUMENTS

| 4,587,958 | A | * | 5/1986 | Noguchi | A61B 17/22012 601/2 |
|---|---|---|---|---|---|
| 2019/0291135 | A1 | * | 9/2019 | Downey | B06B 1/0614 |
| 2020/0289132 | A1 | * | 9/2020 | Mayer | A61B 10/025 |

* cited by examiner

*Primary Examiner* — Ashley L Fishback

(57) ABSTRACT

An ultrasonic surgical handpiece may include an assembled handpiece, an ultrasonic tip, a tubing set, and an irrigation sleeve. The assembled handpiece may include an assembled motor, a housing sleeve, and a nosecone. The housing sleeve and the nosecone may be disposed over a portion of the assembled motor. The assembled motor may include an assembled transducer, a transducer sleeve, and an angled adaptor. The transducer sleeve may be disposed over a portion of the assembled transducer. The assembled transducer may include an amplifier, one or more piezoelectric rings, and a connector block. A surgeon may use the ultrasonic surgical handpiece to perform a portion of a surgical procedure.

20 Claims, 41 Drawing Sheets

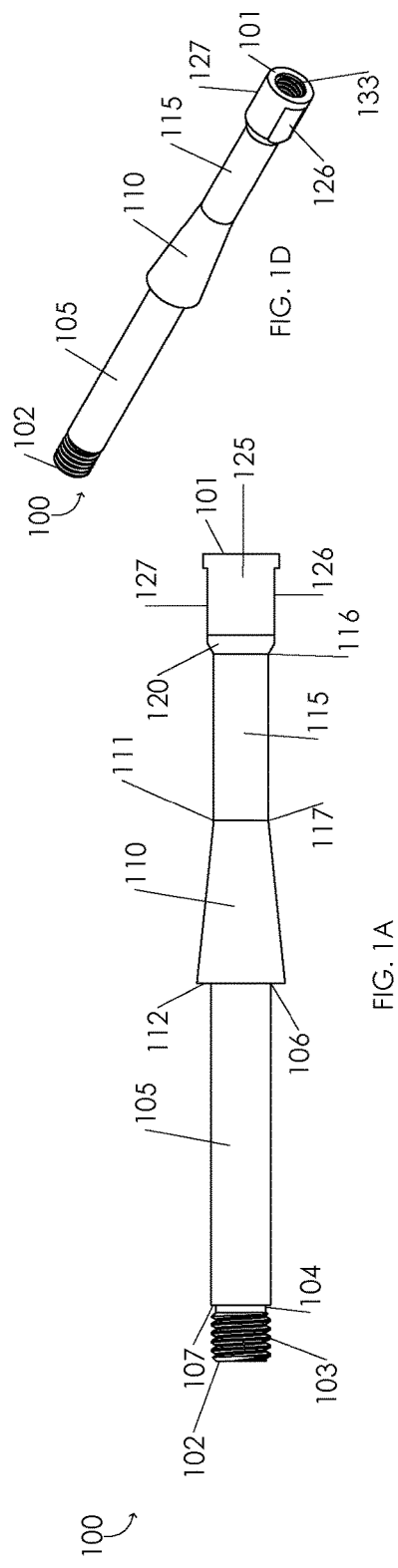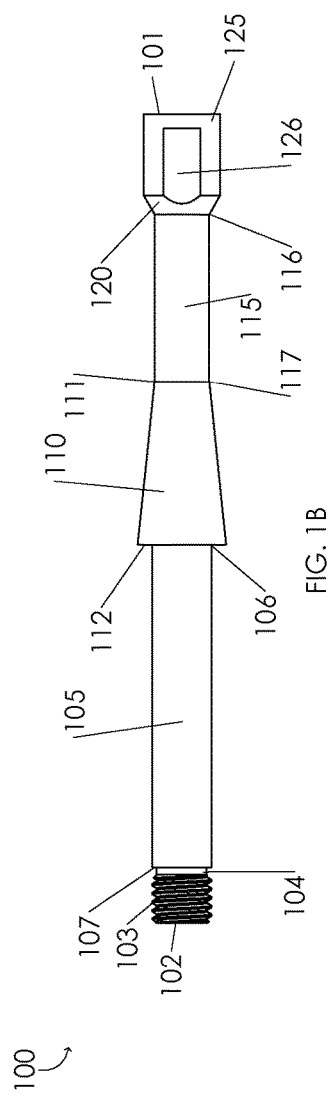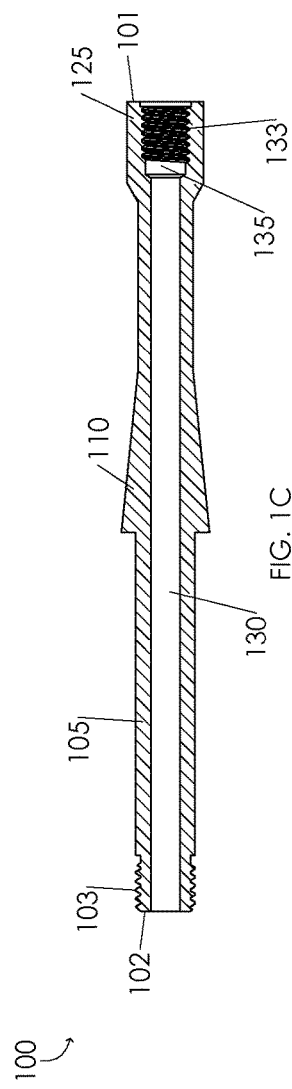

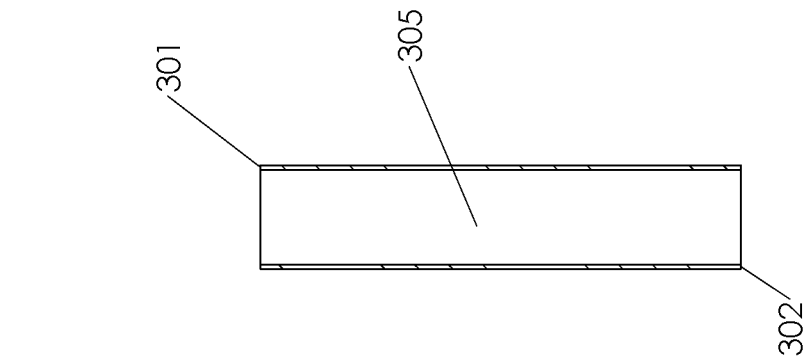
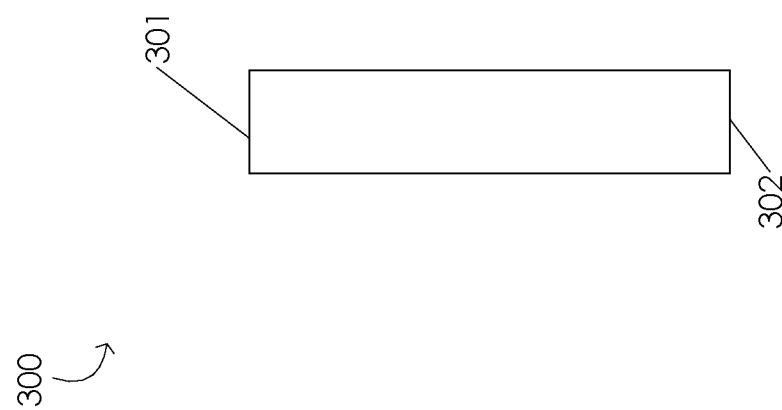

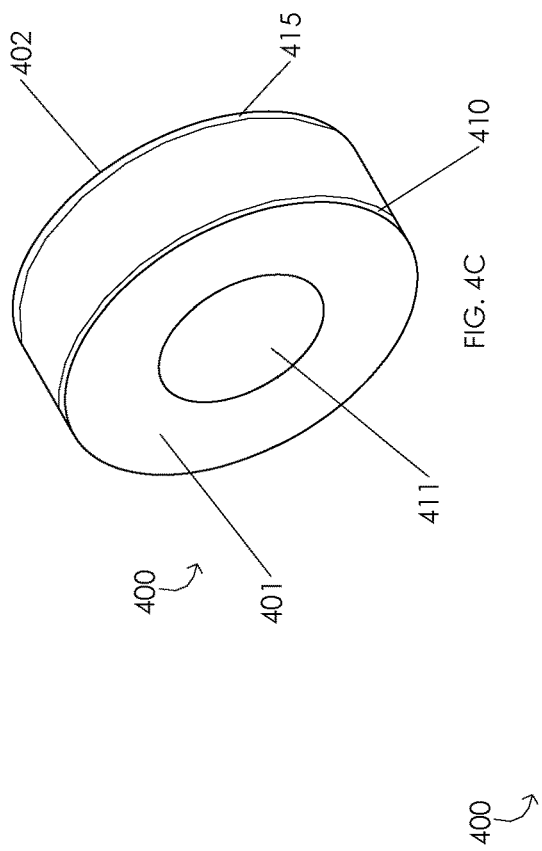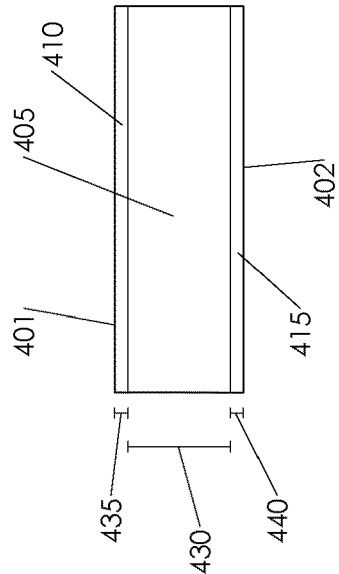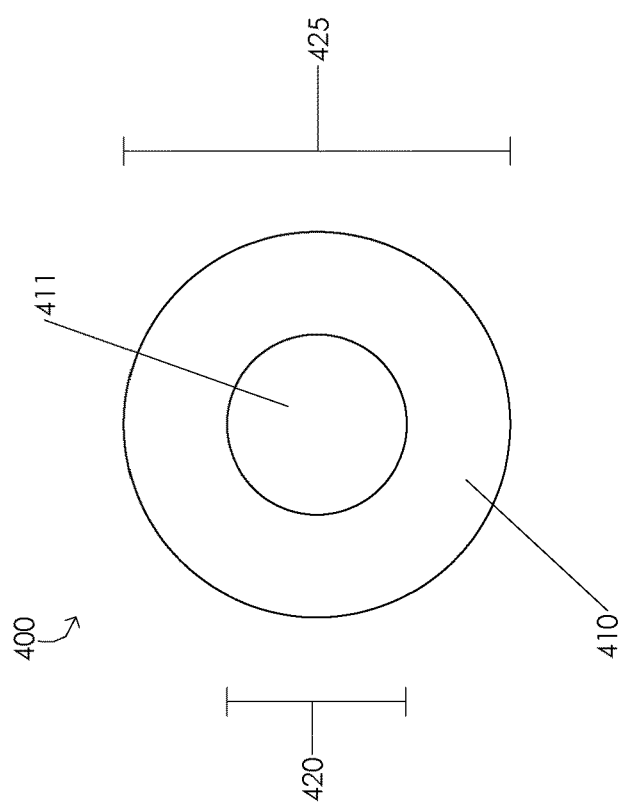

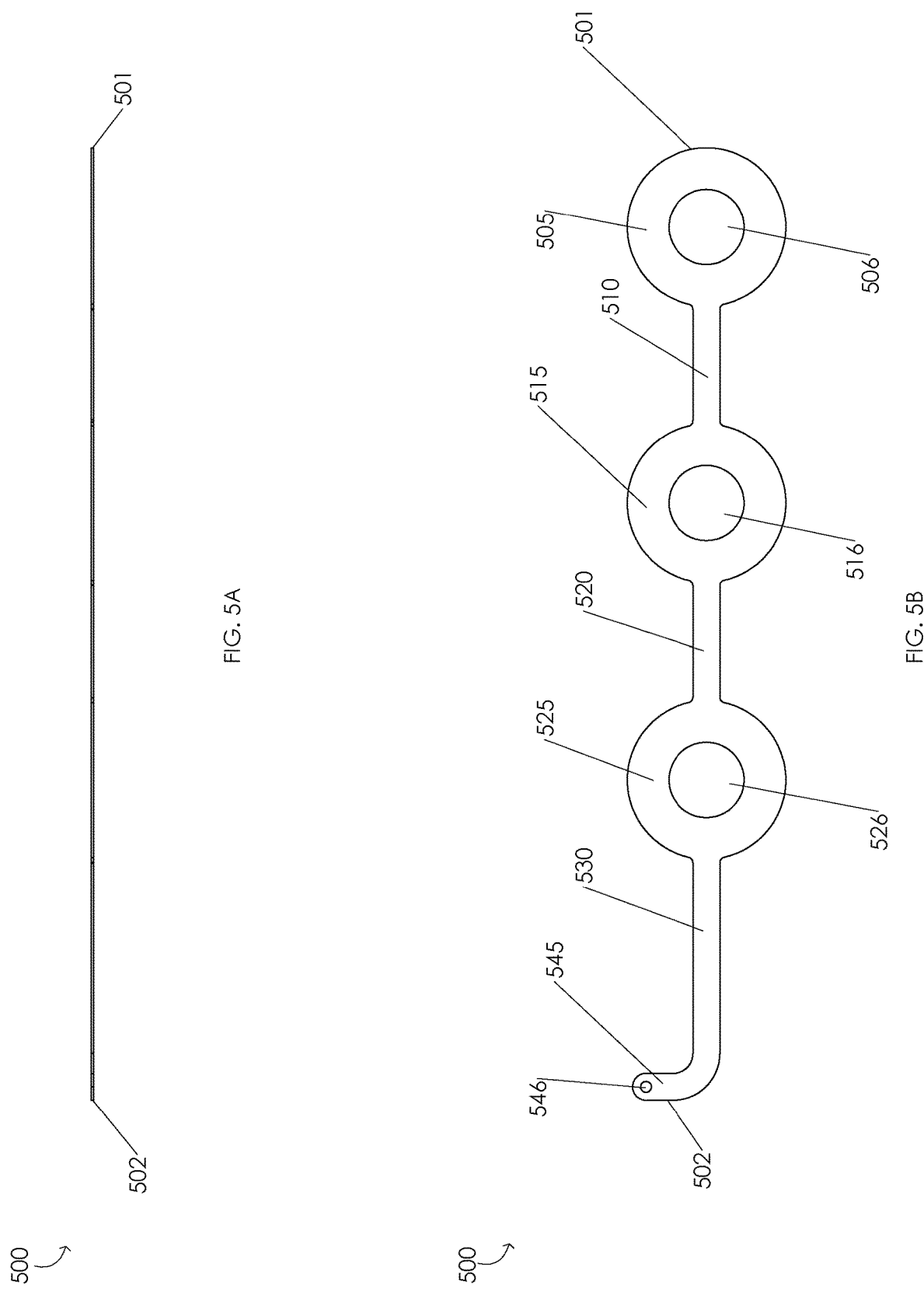

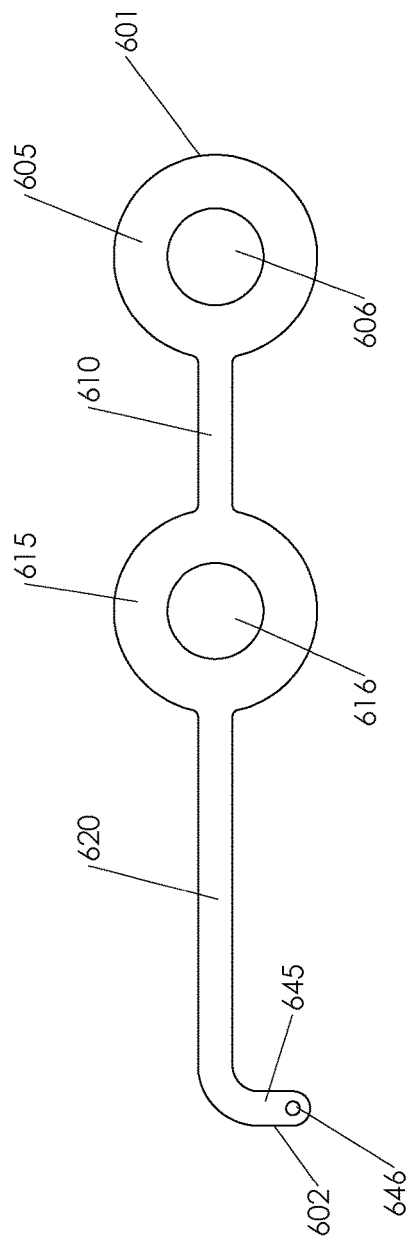

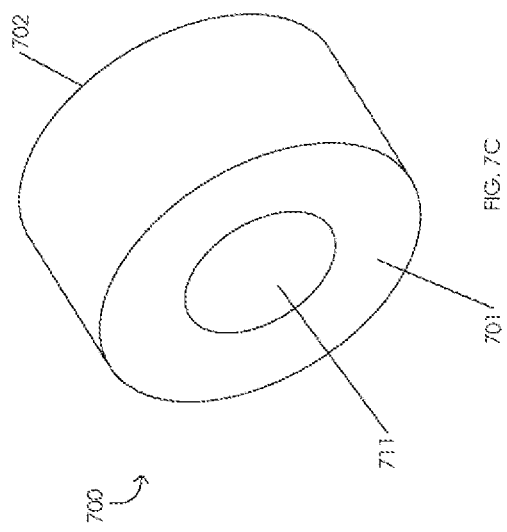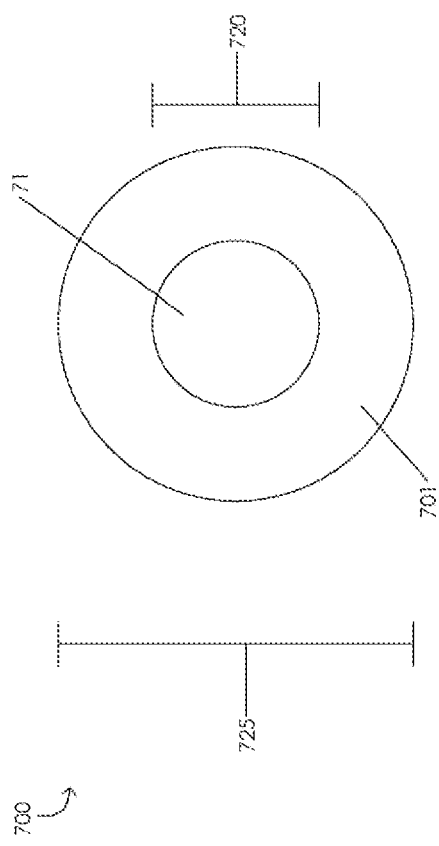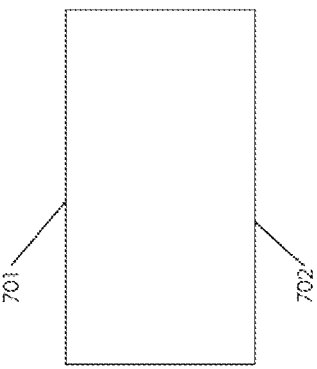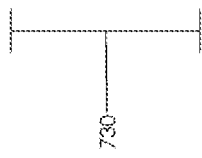

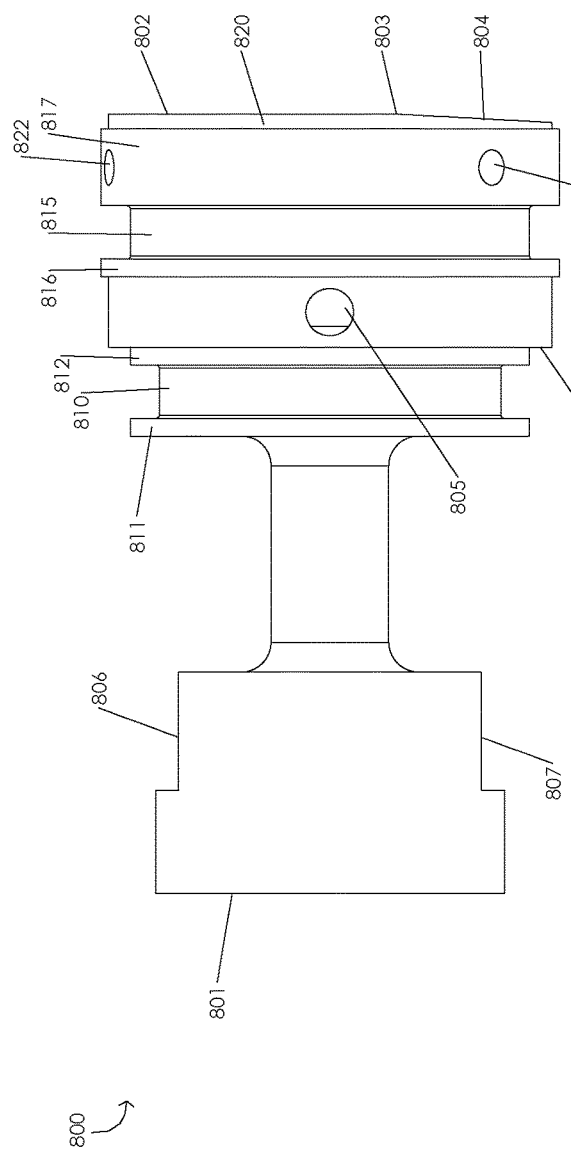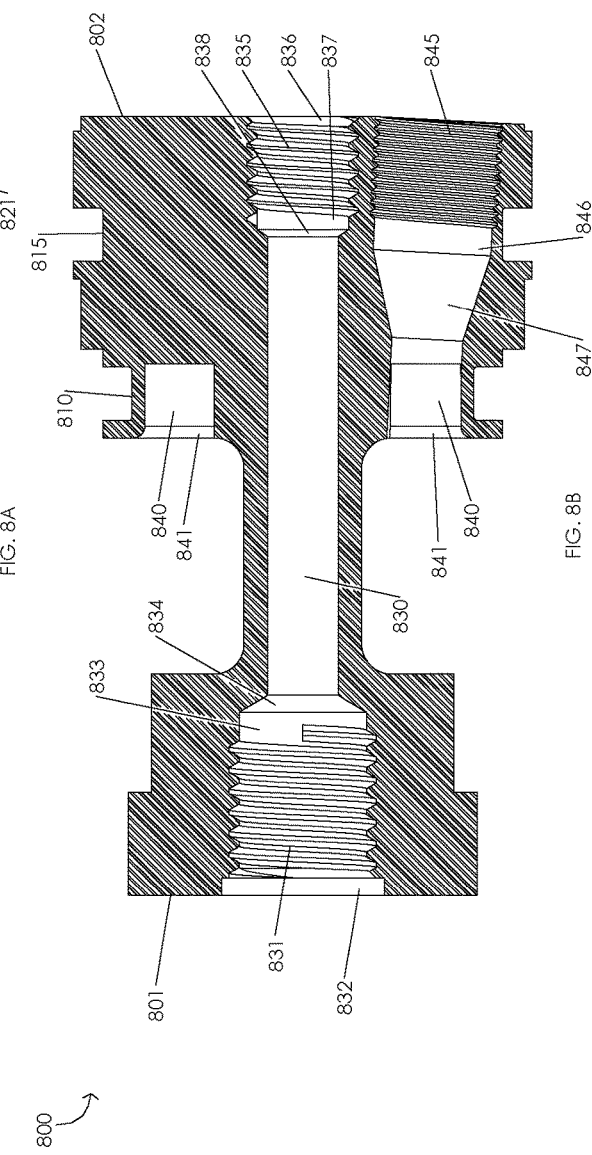
FIG. 8A
FIG. 8B

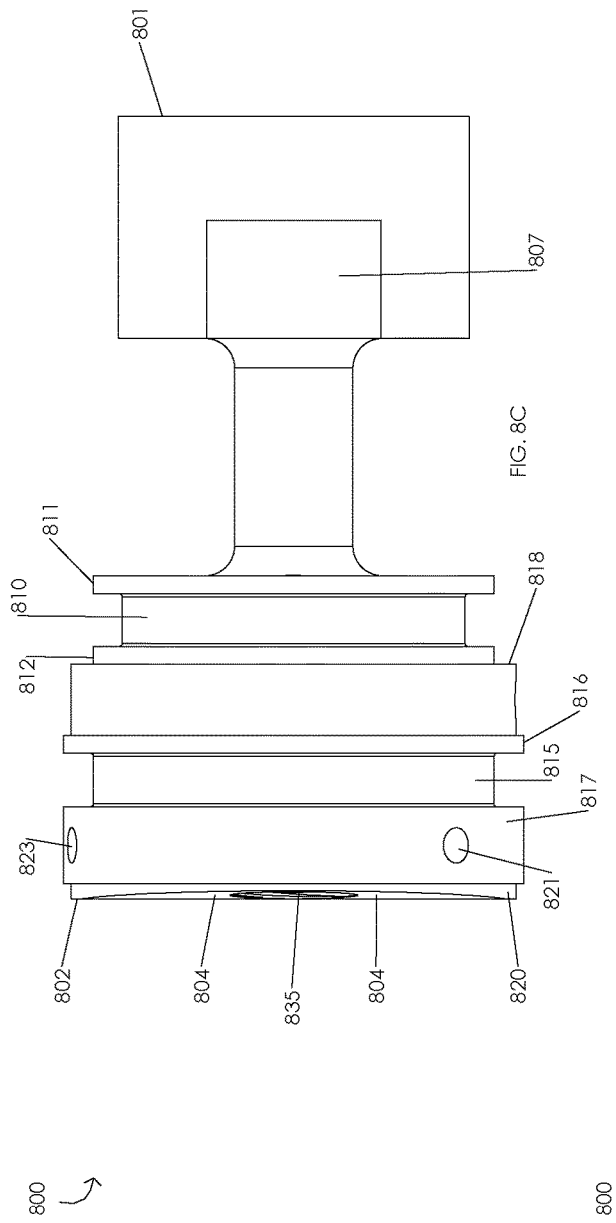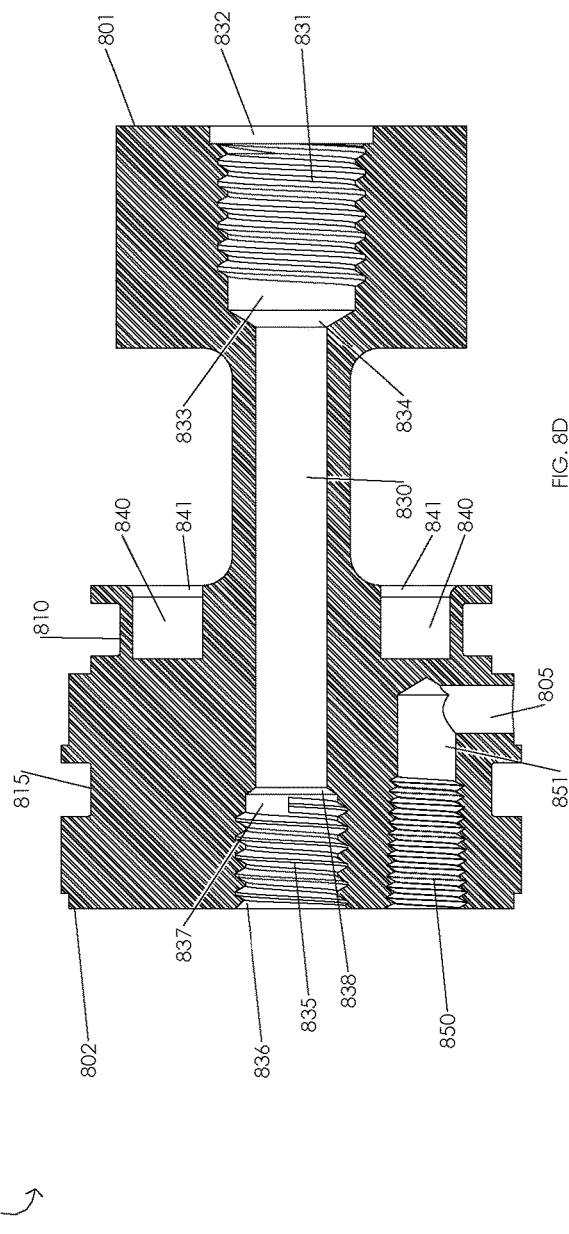

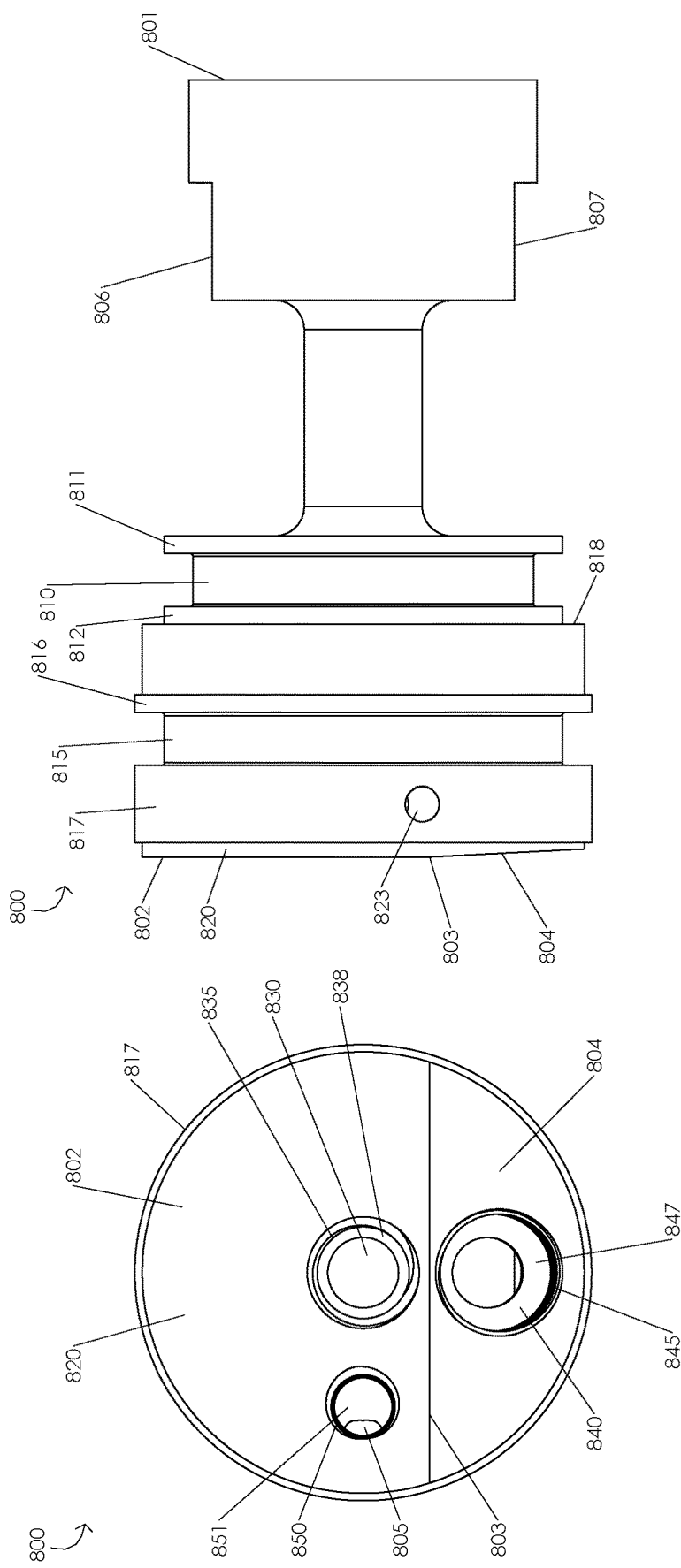

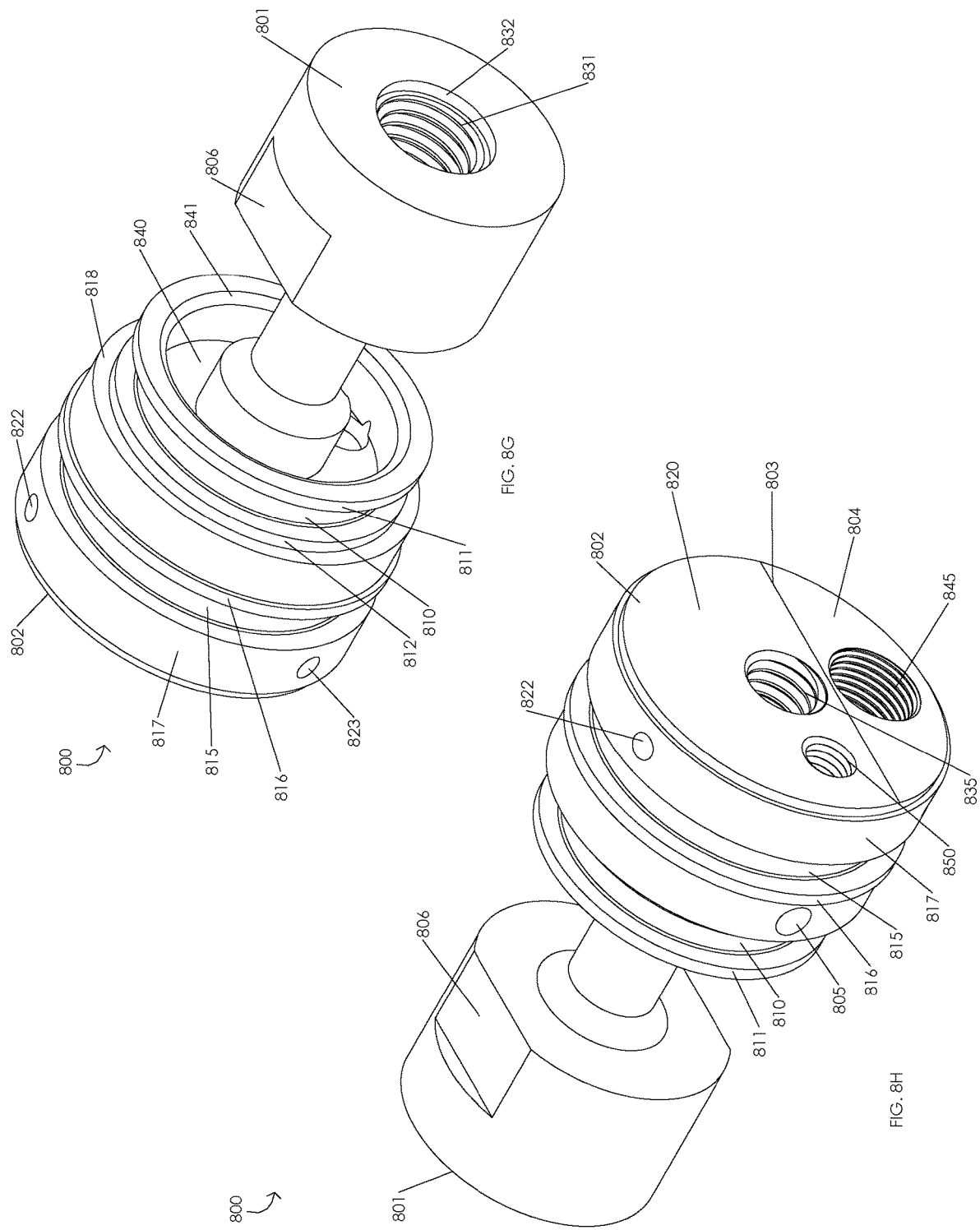

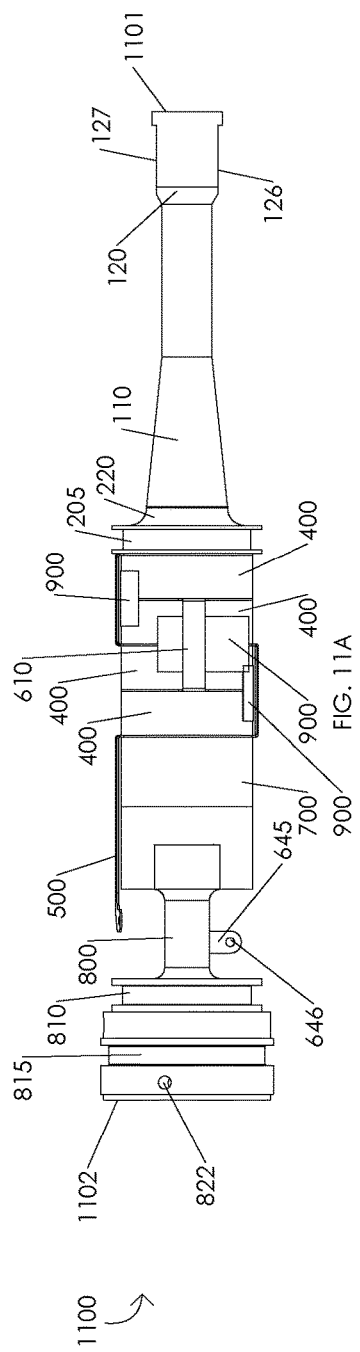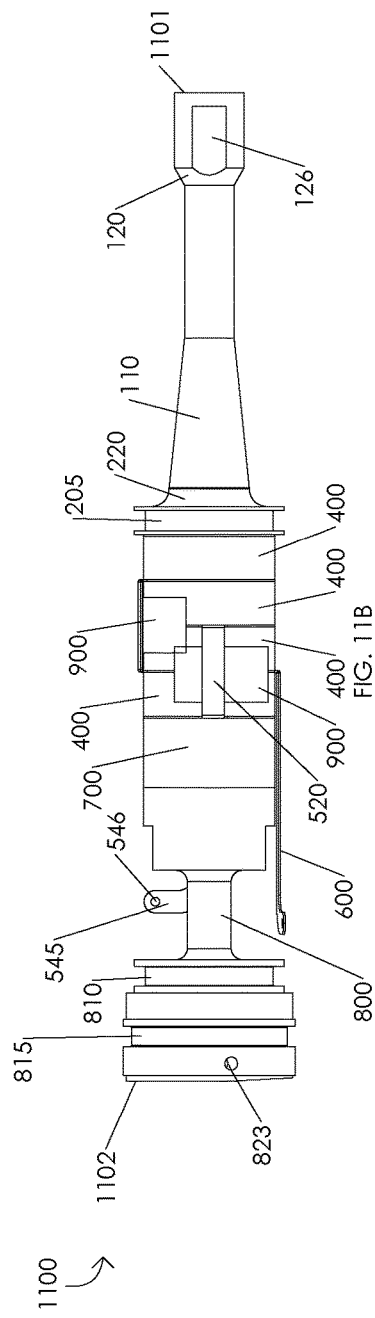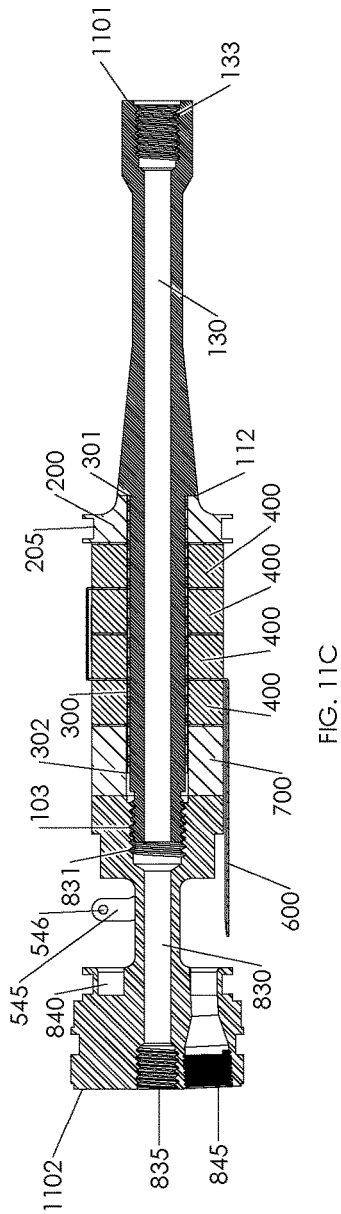

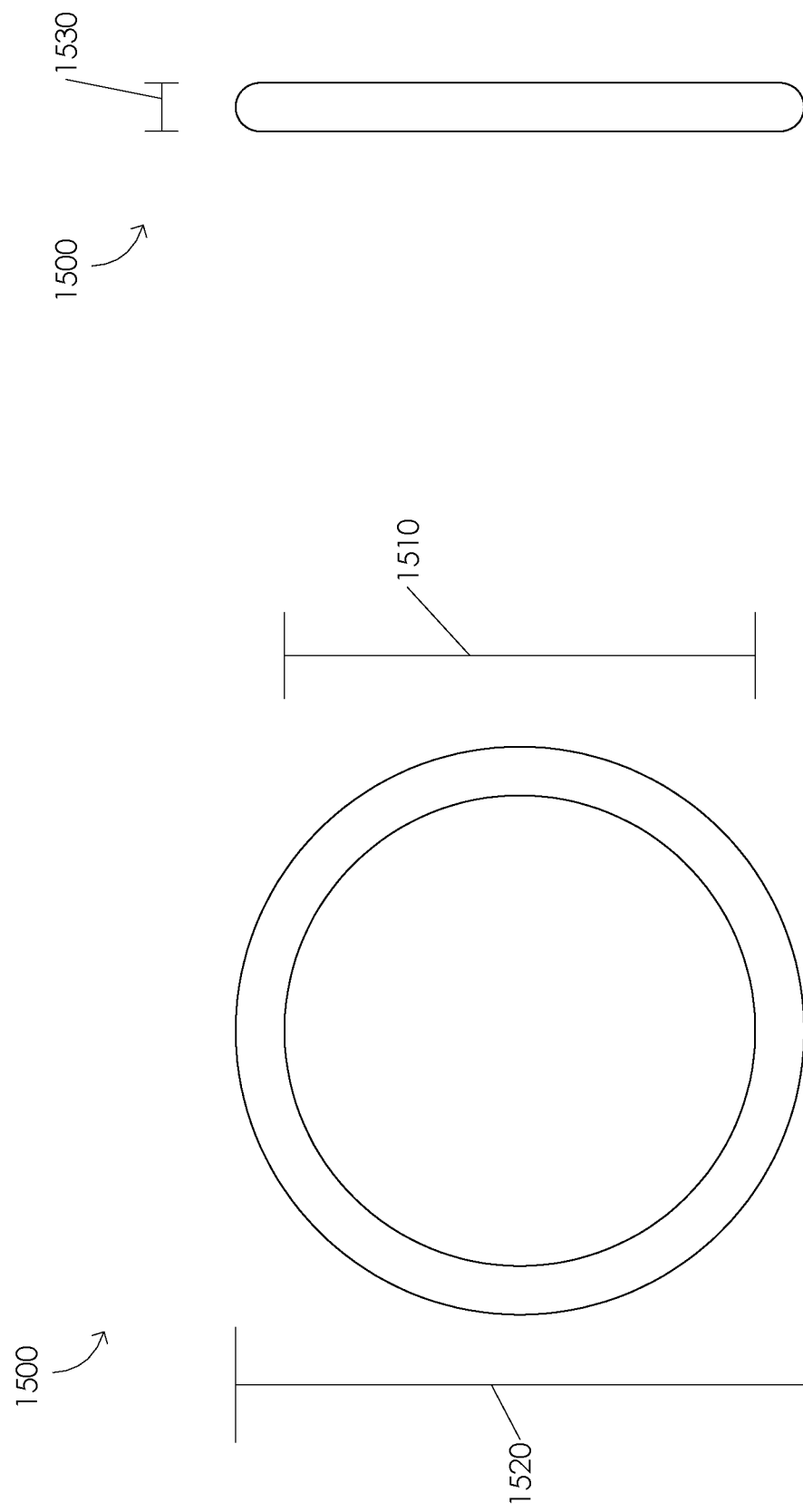

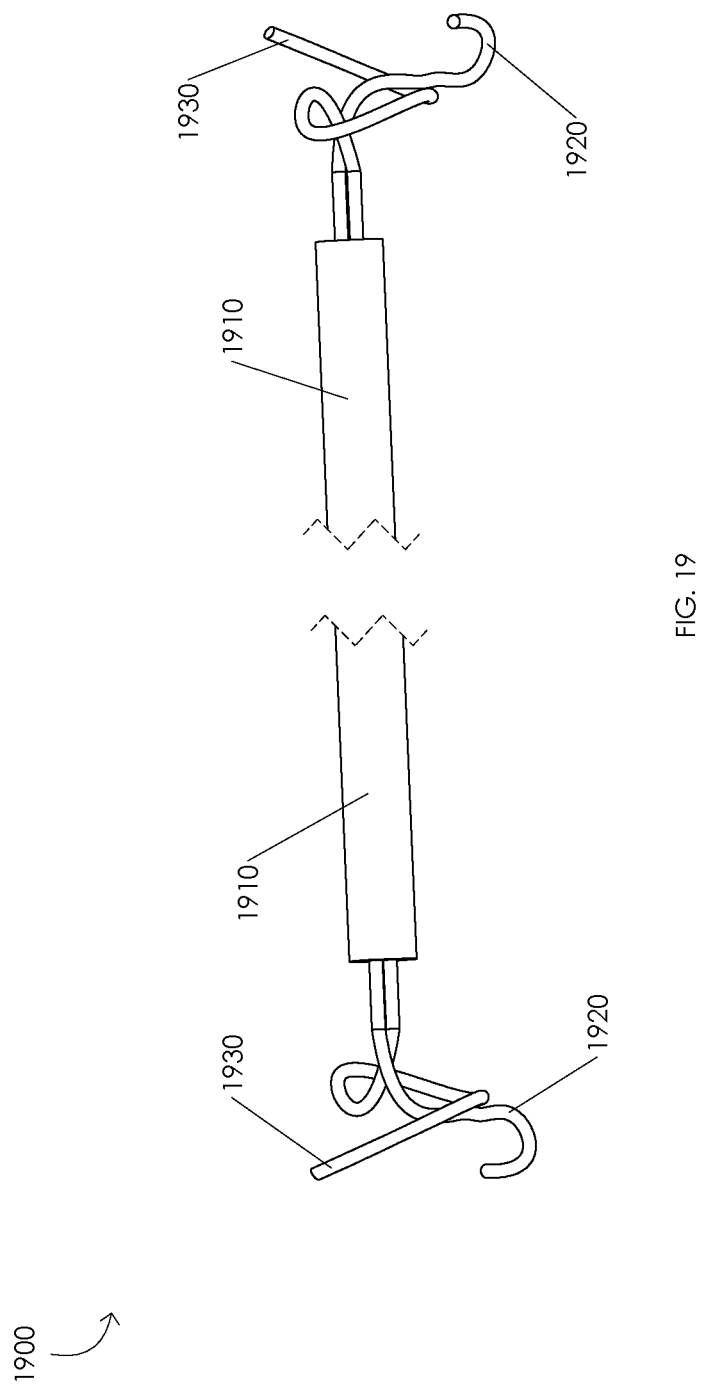

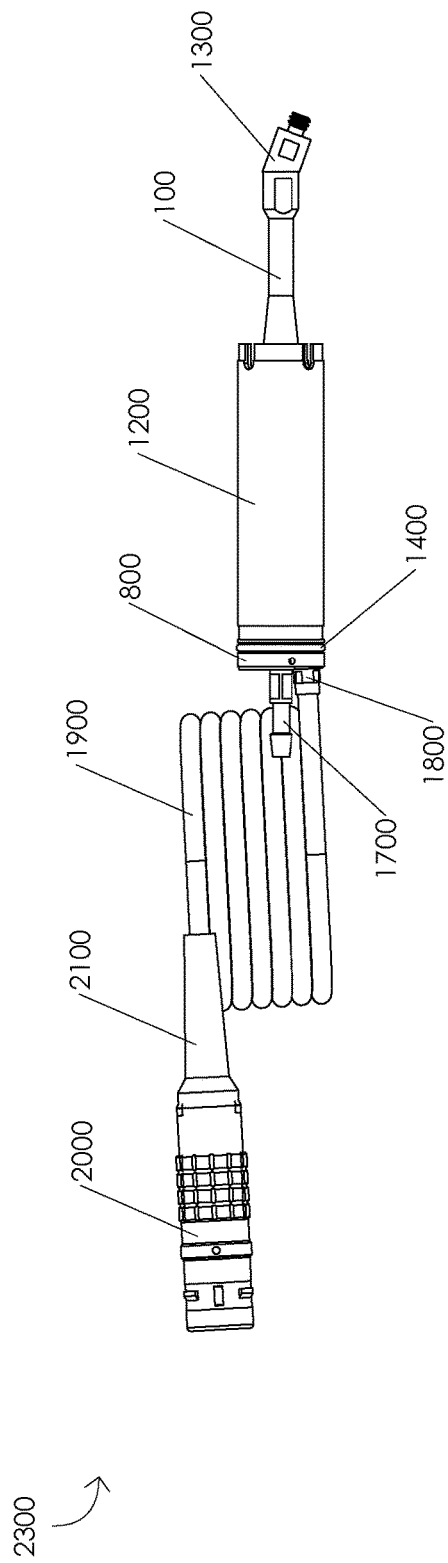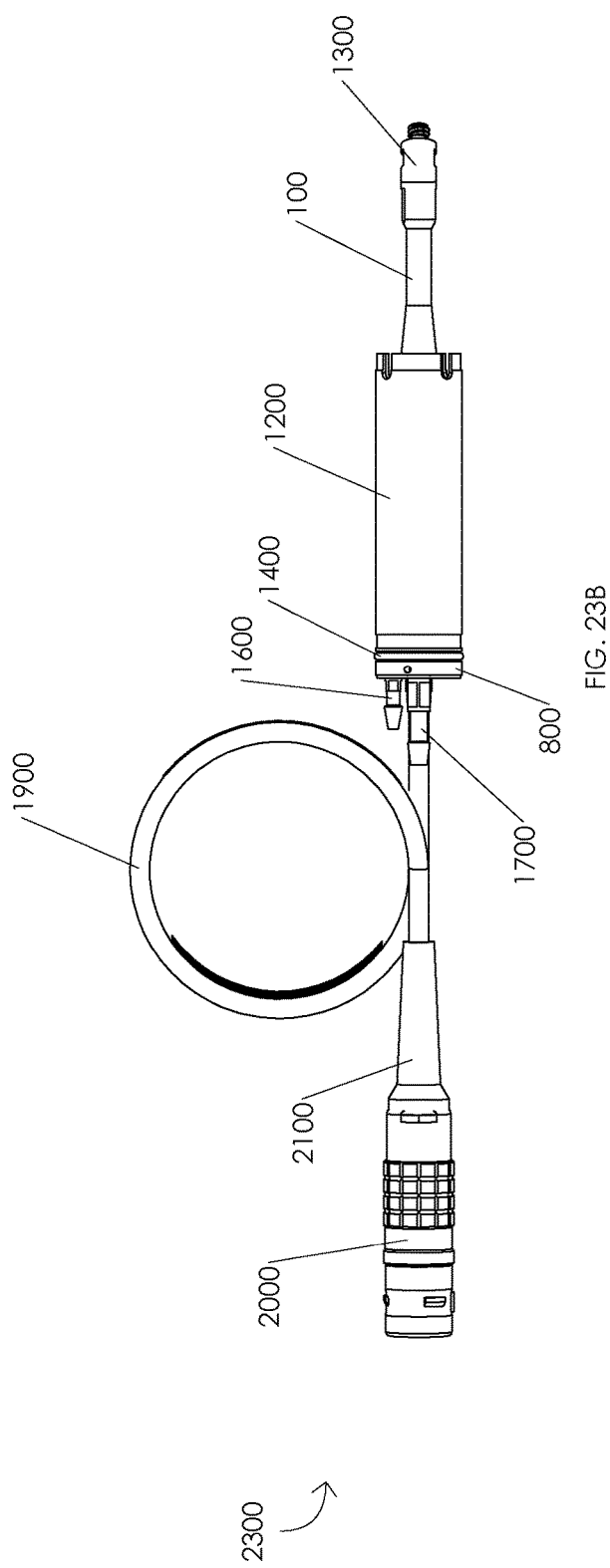

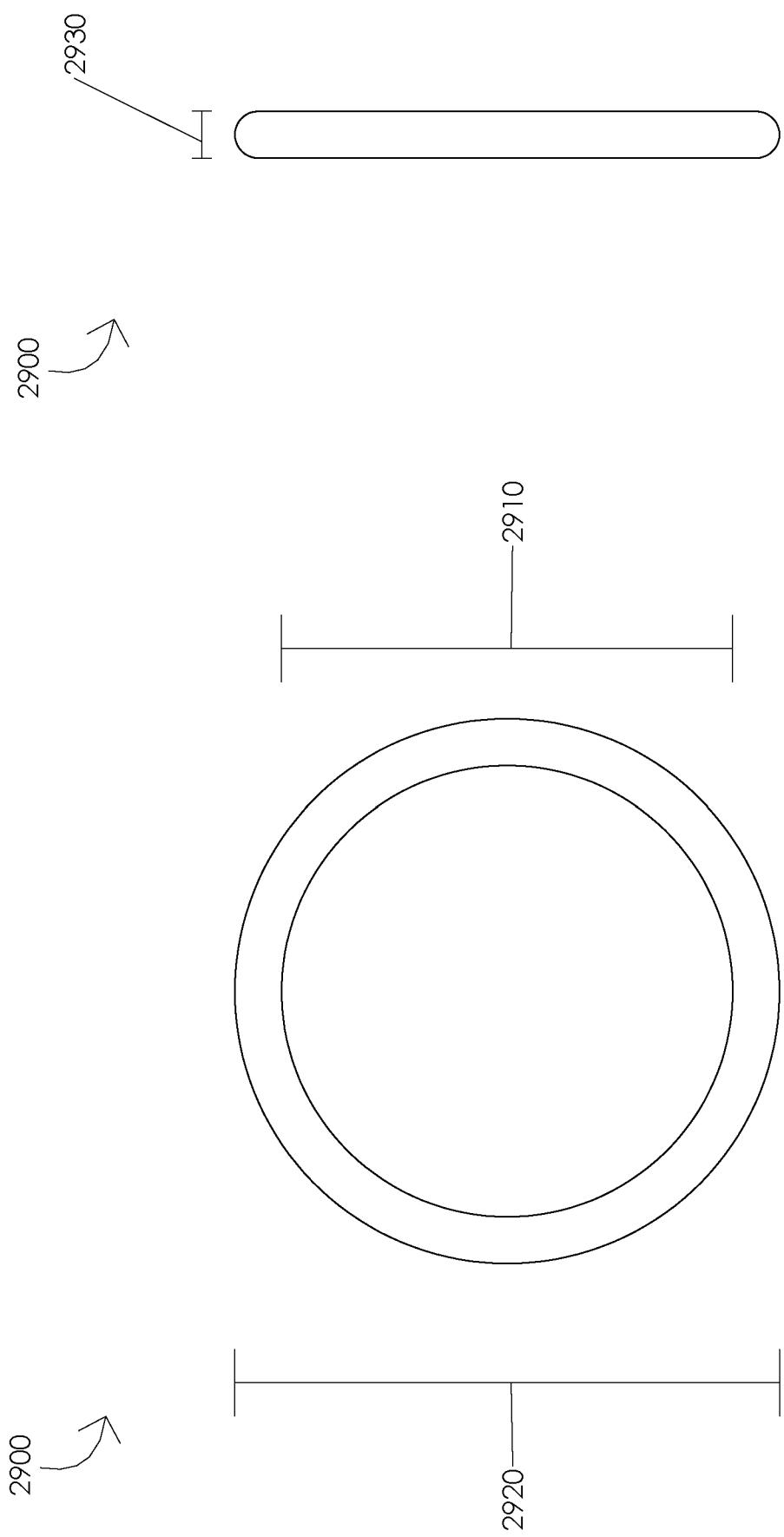

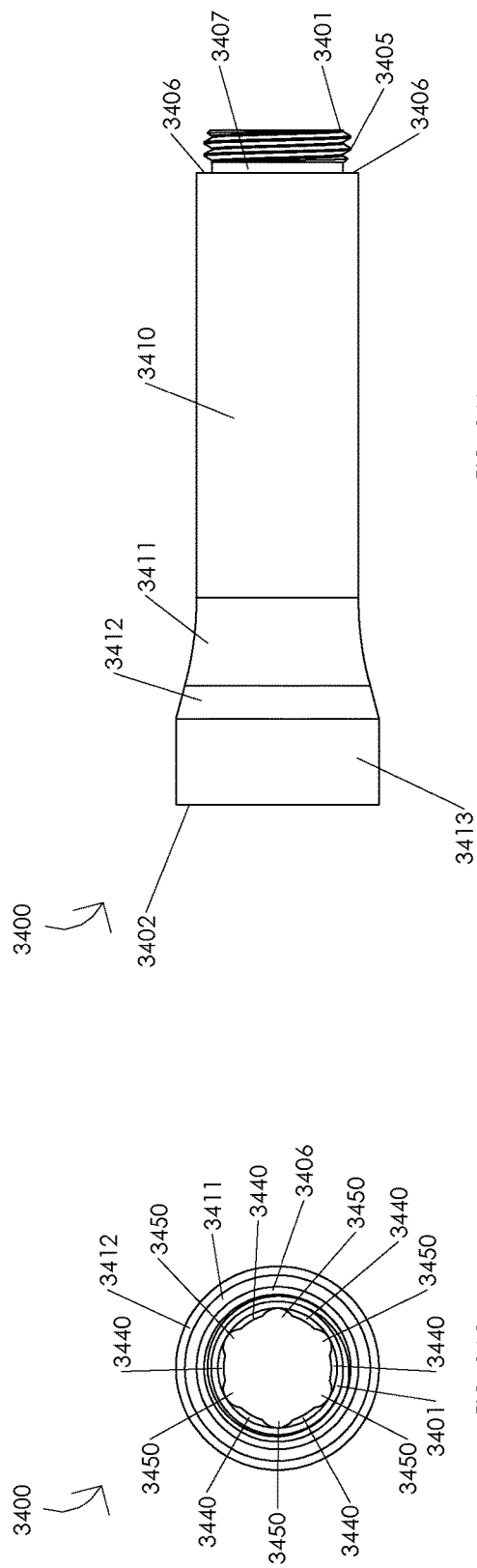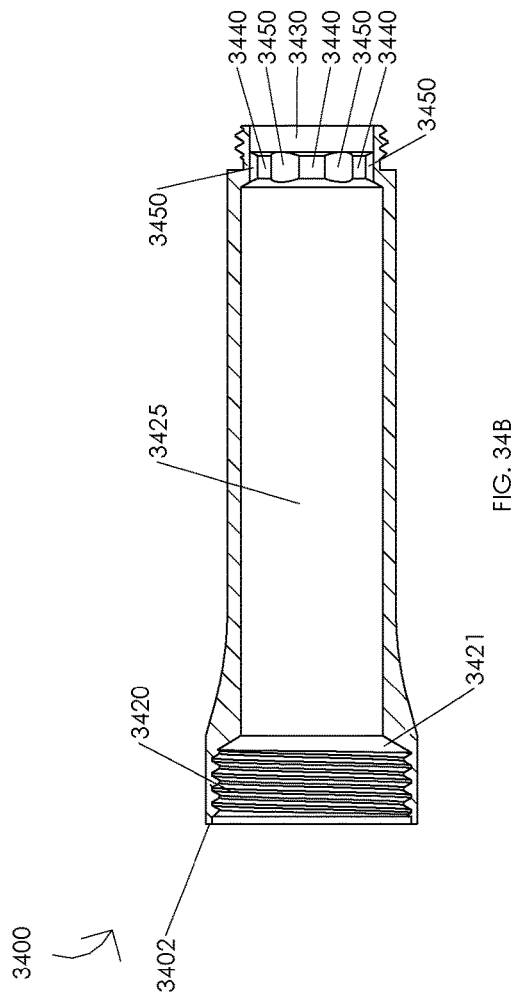

ULTRASONIC SURGICAL HANDPIECE

RELATED APPLICATIONS

This application is related to Ser. No. 62/667,892, filed May 7, 2018, titled "ULTRASONIC SURGICAL HANDPIECE," which is hereby expressly incorporated herein in its entirety including the specification, claims, drawings and abstract.

BACKGROUND OF THE INVENTION

The subject matter herein relates generally to a medical device, and, more particularly, to a surgical handpiece.

Ultrasonic energy is useful for a variety of surgical procedures, such, ultrasonic surgical systems may be used to precisely cut and remove tissue and bone. A typical ultrasonic surgical system comprises a generator and a transducer. The generator may be configured to supply an electrical power at a particular ultrasonic frequency or ultrasonic frequency range to the transducer. The transducer may be configured to convert the electrical power into a mechanical vibration. For example, the transducer may be designed to receive the electrical power wherein the particular ultrasonic frequency or ultrasonic frequency range is a resonance frequency or resonance frequency range of the transducer. The transducer may be disposed in a handpiece which isolates the transducer from contact with a patient or user.

A surgical tip may be connected to a distal end of the transducer or the surgical tip may be connected to a distal end of an ultrasonic horn wherein a proximal end of the ultrasonic horn is connected to the distal end of the transducer. The transducer's mechanical vibration may be transferred to the surgical tip which causes the surgical tip to oscillate at the particular ultrasonic frequency or ultrasonic frequency range. A surgeon may manipulate the handpiece and use the surgical tip to perform a portion of a surgical procedure, e.g., a surgeon may use the ultrasonic oscillation of the surgical tip to cut tissue or bone.

An irrigation fluid may be used to prevent the surgical tip from overheating. The ultrasonic surgical system may comprise a source of the irrigation fluid. For example, an irrigation tube may connect to a first portion of the handpiece and connect to the source of the irrigation fluid to direct the irrigation fluid to the surgical tip.

Aspiration or suction may be used to remove tissue, bone, and the irrigation fluid from a surgical site, e.g., aspiration or suction may be used to remove tissue or bone that is cut by the ultrasonic oscillation of the surgical tip. The ultrasonic surgical system may comprise a source of aspiration or suction. For example, an aspiration or suction tube may connect to a second portion of the handpiece and connect to the source of aspiration or suction to remove tissue, bone, and the irrigation fluid from the surgical site.

Cutting performance of an ultrasonic surgical handpiece is maximized by increasing a maximum oscillation amplitude of an ultrasonic tip wherein the maximum oscillation amplitude of the ultrasonic tip is a distance traveled by a distal end of the ultrasonic tip when a generator is driving the ultrasonic surgical handpiece at full power. The maximum oscillation amplitude of the ultrasonic tip may be calculated as the product of a transducer displacement and a gain of the ultrasonic tip. The gain of the ultrasonic tip may be increased by decreasing a cross-sectional area of the ultrasonic tip.

BRIEF DESCRIPTION OF THE INVENTION

The present disclosure provided an ultrasonic surgical handpiece. In one or more embodiments, an ultrasonic surgical handpiece may comprise an assembled handpiece, an ultrasonic tip, a tubing set, and an irrigation sleeve. Illustratively, the assembled handpiece may comprise an assembled motor, a housing sleeve, and a nosecone. In one or more embodiments, the housing sleeve and the nosecone may be disposed over a portion of the assembled motor. Illustratively, the assembled motor may comprise an assembled transducer, a transducer sleeve, and an angled adaptor. In one or more embodiments, the transducer sleeve may be disposed over a portion of the assembled transducer. Illustratively, the assembled transducer may comprise an amplifier, one or more piezoelectric rings, and a connector block. In one or more embodiments, a surgeon may use the ultrasonic surgical handpiece to perform a portion of a surgical procedure.

BRIEF DESCRIPTION OF THE DRAWINGS

FIGS. 1A, 1B, 1C, and 1D are schematic diagrams illustrating an amplifier.

FIGS. 3A and 3B are schematic diagrams illustrating an amplifier sleeve.

FIGS. 4A, 4B, and 4C are schematic diagrams illustrating a piezoelectric ring.

FIGS. 5A and 5B are schematic diagrams illustrating an outer electrode stack.

FIGS. 6A and 6B are schematic diagrams illustrating an inner electrode stack.

FIGS. 7A, 7B, and 7C are schematic diagrams illustrating an inert ring.

FIGS. 8A, 8B, 8C, 8D, 8E, 8F, 8G, and 8H are schematic diagrams illustrating a connector block.

FIGS. 11A, 11B, and 11C are schematic diagrams illustrating an assembled transducer.

FIGS. 15A and 15B are schematic diagrams illustrating a second fluid seal.

FIG. 19 is a schematic diagram illustrating a cable.

FIGS. 23A and 23B are schematic diagrams illustrating an assembled motor.

FIGS. 29A and 29B are schematic diagrams illustrating a second nosecone grip.

FIGS. 34A, 34B, and 34C are schematic diagrams illustrating a proximal irrigation sleeve.

DETAILED DESCRIPTION OF THE INVENTION

Figure 2B:
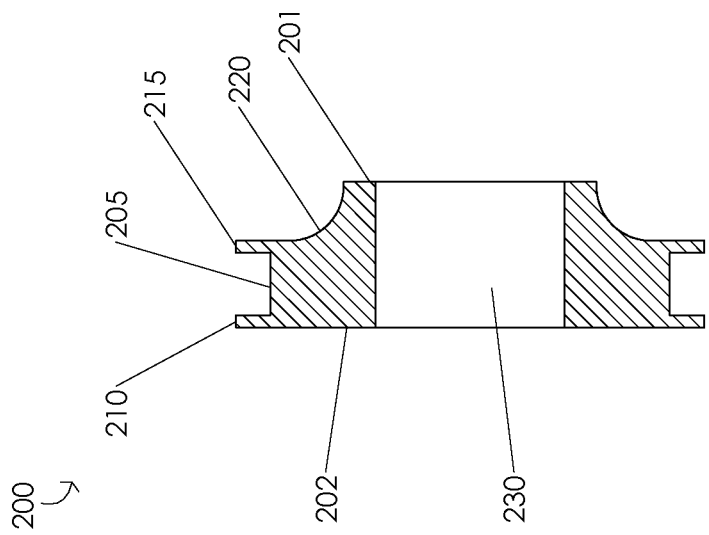
FIGS. 2A and 2B are schematic diagrams illustrating a flange.

FIGS. 1A, 1B, 1C, and 1D are schematic diagrams illustrating an amplifier 100. FIG. 1A illustrates a top view of an amplifier 100. FIG. 1B illustrates a side view of an amplifier 100. FIG. 1C illustrates a cross-sectional view in a sagittal plane of an amplifier 100. FIG. 1D illustrates an isometric view of an amplifier 100. In one or more embodiments, amplifier 100 may comprise an amplifier distal end 101 and an amplifier proximal end 102. Illustratively, amplifier 100 may comprise an amplifier proximal thread 103. In one or more embodiments, amplifier 100 may comprise an amplifier proximal undercut 104. Illustratively, amplifier 100 may comprise a proximal base 105 having a proximal base distal end 106 and a proximal base proximal end 107. In one or more embodiments, amplifier proximal undercut 104 may be disposed between amplifier proximal thread 103 and proximal base 105, e.g., amplifier proximal undercut 104 may be disposed between amplifier proximal thread 103 and proximal base proximal end 107. Illustratively, amplifier 100 may comprise a flange interface taper 110 having a flange interface taper distal end 111 and a flange interface taper proximal end 112. In one or more embodiments, proximal base 105 may be disposed between amplifier proximal thread 103 and flange interface taper 110. Illustratively, amplifier 100 may comprise a distal base 115 having a distal base distal end 116 and a distal base proximal end 117. In one or more embodiments, flange interface taper 110 may be disposed between proximal base 105 and distal base 115. Illustratively, amplifier 100 may comprise an antinode step 120. In one or more embodiments, amplifier 100 may comprise an amplifier interface 125. Illustratively, antinode step 120 may be disposed between distal base 115 and amplifier interface 125. In one or more embodiments, amplifier 100 may comprise a first tool interface 126 and a second tool interface 127. Illustratively, amplifier 100 may comprise an amplifier inner bore 130. In one or more embodiments, amplifier 100 may comprise an amplifier distal thread 133. Illustratively, amplifier distal thread 133 may be disposed in amplifier interface 125. In one or more embodiments, amplifier 100 may comprise an amplifier distal undercut 135. Illustratively, amplifier distal undercut 135 may be disposed in amplifier interface 125.

In one or more embodiments, amplifier 100 may be manufactured from any suitable material, e.g., polymers, metals, metal alloys, etc., or from any combination of suitable materials. Illustratively, amplifier 100 may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, etc. For example, amplifier 100 may be manufactured from a stainless steel, a brass, a bronze, a duralumin, a nitinol, etc. Illustratively, amplifier 100 may be manufactured from an underdamped material. In one or more embodiments, amplifier 100 may be manufactured from a material having a Q factor greater than 0.5. Illustratively, amplifier 100 may be manufactured from a metal alloy in an annealed condition, e.g., amplifier 100 may be manufactured from a titanium alloy in an annealed condition. In one or more embodiments, amplifier 100 may be manufactured from Ti-6Al-4V extra-low interstitials in an annealed condition.

Figure 2A:
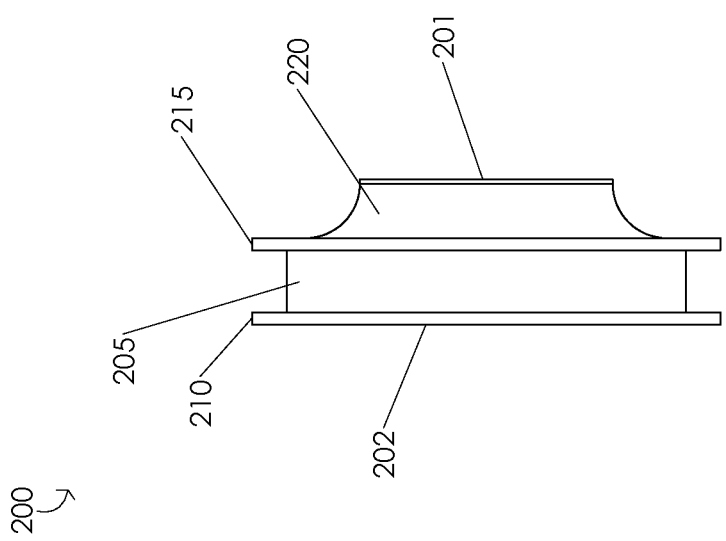

FIGS. 2A and 2B are schematic diagrams illustrating a flange 200. FIG. 2A illustrates a side view of a flange 200. FIG. 2B illustrates a cross-sectional view in a sagittal plane of a flange 200. In one or more embodiments, a flange 200 may comprise a flange distal end 201 and a flange proximal end 202. Illustratively, flange 200 may comprise a first seal housing 205. In one or more embodiments, flange 200 may comprise a flange proximal lip 210. Illustratively, flange 200 may comprise a flange distal lip 215. In one or more embodiments, first seal housing 205 may be disposed between flange proximal lip 210 and flange distal lip 215. Illustratively, flange 200 may comprise a flange fillet 220.

In one or more embodiments, flange 200 may be manufactured from any suitable material, e.g., polymers, metals, metal alloys, etc., or from any combination of suitable materials. Illustratively, flange 200 may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, etc. For example, flange 200 may be manufactured from a stainless steel, a brass, a bronze, a duralumin, a nitinol, etc. Illustratively, flange 200 may be manufactured from an underdamped material. In one or more embodiments, flange 200 may be manufactured from a material having a Q factor greater than 0.5. Illustratively, flange 200 may be manufactured from a metal alloy in an annealed condition, e.g., flange 200 may be manufactured from a titanium alloy in an annealed condition. In one or more embodiments, flange 200 may be manufactured from Ti-6Al-4V extra-low interstitials in an annealed condition. Illustratively, flange 200 and amplifier 100 may be manufactured from a same material. In one or more embodiments, flange 200 and amplifier 100 may be manufactured from different materials, e.g., flange 200 may be manufactured from a first material and amplifier 100 may be manufactured from a second material.

FIGS. 3A and 3B are schematic diagrams illustrating an amplifier sleeve 300. FIG. 3A illustrates a side view of an amplifier sleeve 300. FIG. 3B illustrates a cross-sectional view in a sagittal plane of an amplifier sleeve 300. In one or more embodiments, an amplifier sleeve 300 may comprise an amplifier sleeve distal end 301 and an amplifier sleeve proximal end 302. Illustratively, amplifier sleeve 300 may comprise an amplifier sleeve inner bore 305. In one or more embodiments, amplifier sleeve 300 may be manufactured from any suitable material, e.g., polymers, metals, metal alloys, etc., or from any combination of suitable materials. Illustratively, amplifier sleeve 300 may be manufactured from an electrical insulator material. In one or more embodiments, amplifier sleeve 300 may be manufactured from a thermoplastic polymer material, e.g., amplifier sleeve 300 may be manufactured from polyether ether ketone, polysulfone, poly(methyl methacrylate), acrylonitrile butadiene styrene, polylactide, polycarbonate, polybenzimidazole, polyetherether ketone, polyoxymethylene, polyether sulfone, polyetherimide, polyethylene, polyphenylene sulfide, polyphenylene oxide, polyvinyl chloride, polytetrafluoroethylene, polypropylene, polystyrene, etc.

FIGS. 4A, 4B, and 4C are schematic diagrams illustrating a piezoelectric ring 400. FIG. 4A illustrates a top view of a piezoelectric ring 400. FIG. 4B illustrates a side view of a piezoelectric ring 400. FIG. 4C illustrates an isometric view of a piezoelectric ring 400. In one or more embodiments, a piezoelectric ring 400 may comprise a piezoelectric ring distal end 401 and a piezoelectric ring proximal end 402. Illustratively, piezoelectric ring 400 may comprise a piezoelectric ring base 405. In one or more embodiments, piezoelectric ring base 405 may have a piezoelectric ring thickness 430. Illustratively, piezoelectric ring thickness 430 may be a distance in a range of 0.145 to 0.215 inches, e.g., piezoelectric ring thickness 430 may be a distance of 0.0197 inches. In one or more embodiments, piezoelectric ring thickness 430 may be a distance of less than 0.145 inches or greater than 0.215 inches.

Illustratively, piezoelectric ring 400 may comprise a distal coating 410. In one or more embodiments, distal coating 410 may have a distal coating thickness 435. Illustratively, piezoelectric ring 400 may comprise a proximal coating 415. In one or more embodiments, proximal coating 415 may have a proximal coating thickness 440. Illustratively, piezoelectric ring base 405 may be disposed between proximal coating 415 and distal coating 410. In one or more embodiments, piezoelectric ring 400 may comprise a piezoelectric ring inner bore 411. Illustratively, piezoelectric ring 400 may have a piezoelectric ring inner diameter 420. In one or more embodiments, piezoelectric ring 400 may have a piezoelectric ring outer diameter 425. Illustratively, piezoelectric ring inner diameter 420 may be a distance in a range of 0.175 to 0.375 inches, e.g., piezoelectric ring inner diameter 420 may be a distance of 0.276 inches. In one or more embodiments, piezoelectric ring inner diameter 420 may be a distance of less than 0.175 inches or greater than 0.375 inches. Illustratively, piezoelectric ring outer diameter 425 may be a distance in a range of 0.465 to 0.655 inches, e.g., piezoelectric ring outer diameter 425 may be a distance of 0.591 inches. In one or more embodiments, piezoelectric ring outer diameter 425 may be a distance of less than 0.465 inches or greater than 0.655 inches.

Illustratively, distal coating 410 and proximal coating 415 may be electrical conductors, e.g., distal coating 410 and proximal coating 415 may be manufactured from an electrically conductive material. In one or more embodiments, distal coating 410 and proximal coating 415 may be manufactured from aluminum, an aluminum alloy, silver, a silver alloy, copper, a copper alloy, gold, a gold alloy, platinum, a platinum alloy, tin, a tin alloy, palladium, a palladium alloy, nickel, a nickel alloy, beryllium, a beryllium alloy, tungsten, a tungsten alloy, a steel, chromium, a chromium alloy, titanium, a titanium alloy, etc. Illustratively, distal coating 410 and proximal coating 415 may be manufactured from different materials, e.g., distal coating 410 may be manufactured from a first material and proximal coating 415 may be manufactured from a second material.

In one or more embodiments, piezoelectric ring 400 may be manufactured from a ceramic material, e.g., piezoelectric ring 400 may be manufactured from a piezoelectric ceramic material. Illustratively, piezoelectric ring 400 may be manufactured from a perovskite material, e.g., piezoelectric ring 400 may be manufactured from a lead zirconate titanate ("PZT") material. In one or more embodiments, piezoelectric ring 400 may be manufactured from a piezoxide material, e.g., piezoelectric ring 400 may be manufactured from a PXE 5 grade material, a PXE 52 grade material, a PXE 59 grade material, a PXE 21 grade material, a PXE 41 grade material, a PXE 42 grade material, a PXE 43 grade material, a PXE 71 grade material, etc. Illustratively, piezoelectric ring 400 may be manufactured from a material having a crystal structure with no center of symmetry, e.g., piezoelectric ring 400 may be manufactured from a material having a perovskite crystal structure. In one or more embodiments, piezoelectric ring 400 may be manufactured from a material having a tetragonal crystal lattice elementary cell below the material's Curie temperature, e.g., piezoelectric ring 400 may be manufactured from a material having a cubic crystal lattice elementary cell above the material's Curie temperature. Illustratively, piezoelectric ring 400 may be poled by applying a poling voltage between piezoelectric ring distal end 401 and piezoelectric ring proximal end 402 wherein the poling voltage has a first polarity. In one or more embodiments, an application of a voltage to piezoelectric ring 400 between piezoelectric ring distal end 401 and piezoelectric ring proximal end 402 having the first polarity may be configured to decrease piezoelectric ring thickness 430 and increase piezoelectric ring outer diameter 425. Illustratively, an application of a voltage to piezoelectric ring between piezoelectric ring distal end 401 and piezoelectric ring proximal end 402 having a second polarity may be configured to increase piezoelectric ring thickness 430 and decrease piezoelectric ring outer diameter 425.

FIGS. 5A and 5B are schematic diagrams illustrating an outer electrode stack 500. FIG. 5A illustrates a side view of an outer electrode stack 500. FIG. 5B illustrates a top view of an outer electrode stack 500. In one or more embodiments, an outer electrode stack 500 may comprise an outer electrode stack distal end 501 and an outer electrode stack proximal end 502. Illustratively, outer electrode stack 500 may comprise a first medial electrical conductor 505 having a first medial aperture 506. In one or more embodiments, outer electrode stack 500 may comprise a first lateral electrical conductor 510. Illustratively, outer electrode stack 500 may comprise a third medial electrical conductor 515 having a third medial aperture 516. In one or more embodiments, outer electrode stack 500 may comprise a third lateral electrical conductor 520. Illustratively, outer electrode stack 500 may comprise a fifth medial electrical conductor 525 having a fifth medial aperture 526. In one or more embodiments, outer electrode stack 500 may comprise a first lead 530. Illustratively, first lead 530 may comprise a first lead projection 545 and a first lead guide 546.

In one or more embodiments, outer electrode stack 500 may be manufactured from an electrically conductive material, e.g., outer electrode stack 500 may be manufactured from aluminum, an aluminum alloy, silver, a silver alloy, copper, a copper alloy, gold, a gold alloy, platinum, a platinum alloy, tin, a tin alloy, palladium, a palladium alloy, nickel, a nickel alloy, beryllium, a beryllium alloy, tungsten, a tungsten alloy, a steel, chromium, a chromium alloy, titanium, a titanium alloy, etc. Illustratively, outer electrode stack 500 may be manufactured from a beryllium copper. In one or more embodiments, outer electrode stack 500 may be manufactured from a stainless steel, e.g., outer electrode stack 500 may be manufactured from a spring steel.

FIGS. 6A and 6B are schematic diagrams illustrating an inner electrode stack 600. FIG. 6A illustrates a side view of an inner electrode stack 600. FIG. 6B illustrates a top view of an inner electrode stack 600. In one or more embodiments, an inner electrode stack 600 may comprise an inner electrode stack distal end 601 and an inner electrode stack proximal end 602. Illustratively, inner electrode stack 600 may comprise a second medial electrical conductor 605 having a second medial aperture 606. In one or more embodiments, inner electrode stack 600 may comprise a second lateral electrical conductor 610. Illustratively, inner electrode stack 600 may comprise a fourth medial electrical conductor 615 having a fourth medial aperture 616. In one or more embodiments, inner electrode stack 600 may comprise a second lead 620. Illustratively, second lead 620 may comprise a second lead projection 645 and a second lead guide 646.

In one or more embodiments, inner electrode stack 600 may be manufactured from an electrically conductive material, e.g., inner electrode stack 600 may be manufactured from aluminum, an aluminum alloy, silver, a silver alloy, copper, a copper alloy, gold, a gold alloy, platinum, a platinum alloy, tin, a tin alloy, palladium, a palladium alloy, nickel, a nickel alloy, beryllium, a beryllium alloy, tungsten, a tungsten alloy, a steel, chromium, a chromium alloy, titanium, a titanium alloy, etc. Illustratively, inner electrode stack 600 may be manufactured from a beryllium copper. In one or more embodiments, inner electrode stack 600 may be manufactured from a stainless steel, e.g., inner electrode stack 600 may be manufactured from a spring steel.

FIGS. 7A, 7B, and 7C are schematic diagrams illustrating an inert ring 700. FIG. 7A illustrates a top view of an inert ring 700. FIG. 7B illustrates a side view of an inert ring 700. FIG. 7C illustrates an isometric view of an inert ring 700. In one or more embodiments, an inert ring 700 may comprise an inert ring distal end 701 and an inert ring proximal end 702. Illustratively, inert ring 700 may have an inert ring thickness 730. In one or more embodiments, inert ring thickness 730 may be a distance in a range of 0.265 to 0.385 inches, e.g., inert ring thickness 730 may be a distance of 0.314 inches. Illustratively, inert ring thickness 730 may be a distance of less than 0.265 inches or greater than 0.385 inches. In one or more embodiments, inert ring 700 may comprise an inert ring inner bore 711. Illustratively, inert ring 700 may have an inert ring inner diameter 720. In one or more embodiments, inert ring 700 may have an inert ring outer diameter 725. Illustratively, inert ring inner diameter 720 may be a distance in a range of 0.175 to 0.375 inches, e.g., inert ring inner diameter 720 may be a distance of 0.276 inches. In one or more embodiments, inert ring inner diameter 720 may be a distance of less than 0.175 inches or greater than 0.375 inches. Illustratively, inert ring outer diameter 725 may be a distance in a range of 0.465 to 0.655 inches, e.g., inert ring outer diameter 725 may be a distance of 0.591 inches. In one or more embodiments, inert ring outer diameter 725 may be a distance of less than 0.465 inches or greater than 0.655 inches.

In one or more embodiments, inert ring 700 may be manufactured from any suitable material, e.g., polymers, metals, metal alloys, etc., or from any combination of suitable materials. Illustratively, inert ring 700 may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, etc. For example, inert ring 700 may be manufactured from a stainless steel, a brass, a bronze, a duralumin, a nitinol, etc. Illustratively, inert ring 700 may be manufactured from an underdamped material. In one or more embodiments, inert ring 700 may be manufactured from a material having a Q factor greater than 0.5. Illustratively, inert ring 700 may be manufactured from a metal alloy in an annealed condition, e.g., inert ring 700 may be manufactured from a titanium alloy in an annealed condition. In one or more embodiments, inert ring 700 may be manufactured from Ti-6Al-4V extra-low interstitials in an annealed condition. Illustratively, flange 200, amplifier 100, and inert ring 700 may be manufactured from a same material. In one or more embodiments, flange 200, amplifier 100, and inert ring 700 may be manufactured from different materials, e.g., flange 200 may be manufactured from a first material, amplifier 100 may be manufactured from a second material, and inert ring 700 may be manufactured from a third material.

FIGS. 8A, 8B, 8C, 8D, 8E, 8F, 8G, and 8H are schematic diagrams illustrating a connector block 800. FIG. 8A illustrates a first side view of a connector block 800. FIG. 8B illustrates a cross-sectional view in a sagittal plane of a connector block 800. FIG. 8C illustrates a top view of a connector block 800. FIG. 8D illustrates a cross-sectional view in a transverse plane of a connector block 800. FIG. 8E illustrates a rear view of a connector block 800. FIG. 8F illustrates a second side view of a connector block 800. FIG. 8G illustrates an isometric view from a distal perspective of a connector block 800. FIG. 8H illustrates an isometric view from a proximal perspective of a connector block 800. In one or more embodiments, a connector block 800 may comprise a connector block distal end 801 and a connector block proximal end 802. Illustratively, connector block 800 may comprise an offset face interface 803. In one or more embodiments, connector block 800 may comprise an offset face 804. Illustratively, connector block 800 may comprise a conduit 805. In one or more embodiments, connector block 800 may comprise a first connector block tool interface 806 and a second connector block tool interface 807. Illustratively, connector block 800 may comprise a second seal housing 810. In one or more embodiments, connector block 800 may comprise a second seal housing distal lip 811 and a second seal housing proximal lip 813. Illustratively, second seal housing 810 may be disposed between second seal housing distal lip 811 and second seal housing proximal lip 813. In one or more embodiments, connector block 800 may comprise a third seal housing 815. Illustratively, connector block 800 may comprise a third seal housing distal lip 816. In one or more embodiments, connector block 800 may comprise a fixation mechanism base 817. Illustratively, third seal housing 815 may be disposed between third seal housing distal lip 816 and fixation mechanism base 817.

In one or more embodiments, connector block 800 may comprise a collar mount 820. Illustratively, fixation mechanism base 817 may be disposed between third seal housing 815 and collar mount 820. In one or more embodiments, conduit 805 may be disposed between second seal housing proximal lip 812 and third seal housing distal lip 816. Illustratively, connector block 800 may comprise a transducer sleeve interface 818. In one or more embodiments, transducer sleeve interface 818 may be disposed between second seal housing proximal lip 812 and conduit 805.

Illustratively, connector block 800 may comprise a first fixation mechanism housing 821, e.g., fixation mechanism base 817 may comprise a first fixation mechanism housing 822. In one or more embodiments, connector block 800 may comprise a second fixation mechanism housing 822, e.g., fixation mechanism base 817 may comprise a second fixation mechanism housing 822. Illustratively, connector block 800 may comprise a third fixation mechanism housing 823, e.g., fixation mechanism base 817 may comprise a third fixation mechanism housing 823. In one or more embodiments, connector block 800 may comprise a connector block inner bore 830. Illustratively, connector block 800 may comprise a connector block distal thread 831. In one or more embodiments, connector block 800 may comprise a connector block distal undercut 832. Illustratively, connector block 800 may comprise an amplifier housing 833. In one or more embodiments, connector block 800 may comprise an amplifier housing taper 834. Illustratively, connector block distal thread 831 may be disposed between connector block distal undercut 832 and amplifier housing taper 834.

In one or more embodiments, connector block 800 may comprise a first connector block proximal thread 835. Illustratively, connector block 800 may comprise a first connector block proximal undercut 836. In one or more embodiments, connector block 800 may comprise an aspiration barb housing 837. Illustratively, connector block 800 may comprise an aspiration barb housing taper 838. In one or more embodiments, first connector block proximal thread 835 may be disposed between aspiration barb housing taper 838 and first connector block proximal undercut 836. Illustratively, connector block 800 may comprise a recess 840. In one or more embodiments, connector block 800 may comprise a recess lateral fillet 841. Illustratively, connector block 800 may comprise a second connector block proximal thread 845. In one or more embodiments, connector block 800 may comprise a retention mechanism housing 846. Illustratively, connector block 800 may comprise a retention mechanism housing taper 847. In one or more embodiments, connector block 800 may comprise a third connector block proximal thread 850. Illustratively, connector block 800 may comprise an irrigation barb housing 851.

In one or more embodiments, connector block 800 may be manufactured from any suitable material, e.g., polymers, metals, metal alloys, etc., or from any combination of suitable materials. Illustratively, connector block 800 may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, etc. For example, connector block 800 may be manufactured from a stainless steel, a brass, a bronze, a duralumin, a nitinol, etc. Illustratively, connector block 800 may be manufactured from an underdamped material. In one or more embodiments, connector block 800 may be manufactured from a material having a Q factor greater than 0.5. Illustratively, connector block 800 may be manufactured from a metal alloy in an annealed condition, e.g., connector block 800 may be manufactured from a titanium alloy in an annealed condition. In one or more embodiments, connector block 800 may be manufactured from Ti-6Al-4V extra-low interstitials in an annealed condition. Illustratively, flange 200, amplifier 100, inert ring 700, and connector block 800 may be manufactured from a same material. In one or more embodiments, flange 200, amplifier 100, inert ring 700, and connector block 800 may be manufactured from different materials, e.g., flange 200 may be manufactured from a first material, amplifier 100 may be manufactured from a second material, inert ring 700 may be manufactured from a third material, and connector block 800 may be manufactured from a fourth material.

Figure 9A:
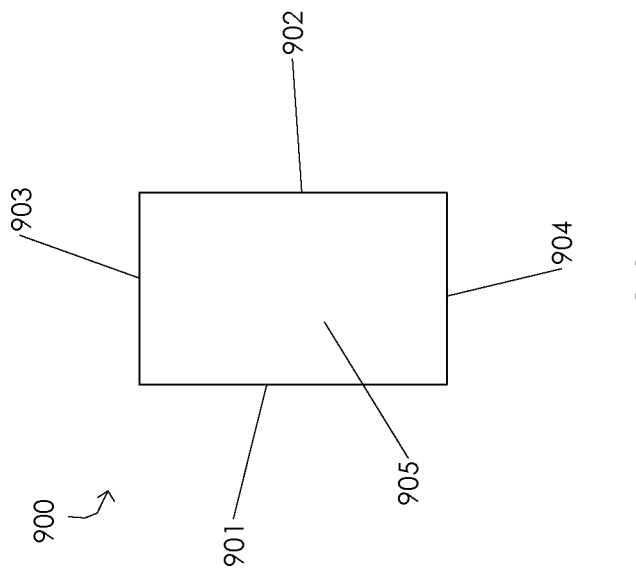
FIGS. 9A and 9B are schematic diagrams illustrating an electrical insulator.
Figure 9B:
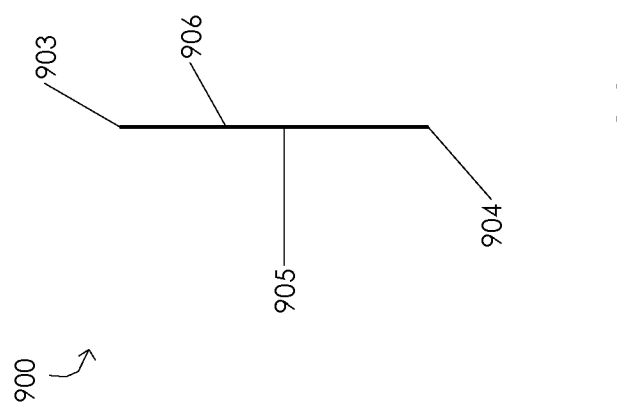

FIGS. 9A and 9B are schematic diagrams illustrating an electrical insulator 900. FIG. 9A illustrates a top view of an electrical insulator 900. FIG. 9B illustrates a side view of an electrical insulator 900. In one or more embodiments, an electrical insulator 900 may comprise an electrical insulator distal end 901 and an electrical insulator proximal end 902. Illustratively, electrical insulator 900 may comprise an electrical insulator superior end 903 and an electrical insulator inferior end 904. In one or more embodiments, electrical insulator 900 may comprise an electrical insulator anterior end 905 and an electrical insulator posterior end 906.

In one or more embodiments, electrical insulator 900 may be manufactured from any suitable material, e.g., polymers, metals, metal alloys, etc., or from any combination of suitable materials. Illustratively, electrical insulator 900 may be manufactured from an electrical insulator material. In one or more embodiments, electrical insulator 900 may be manufactured from a thermoplastic polymer material, e.g., electrical insulator 900 may be manufactured from polyether ether ketone, polysulfone, poly(methyl methacrylate), acrylonitrile butadiene styrene, polylactide, polycarbonate, polybenzimidazole, polyetherether ketone, polyoxymethylene, polyether sulfone, polyetherimide, polyethylene, polyphenylene sulfide, polyphenylene oxide, polyvinyl chloride, polytetrafluoroethylene, polypropylene, polystyrene, etc.

Figure 10:
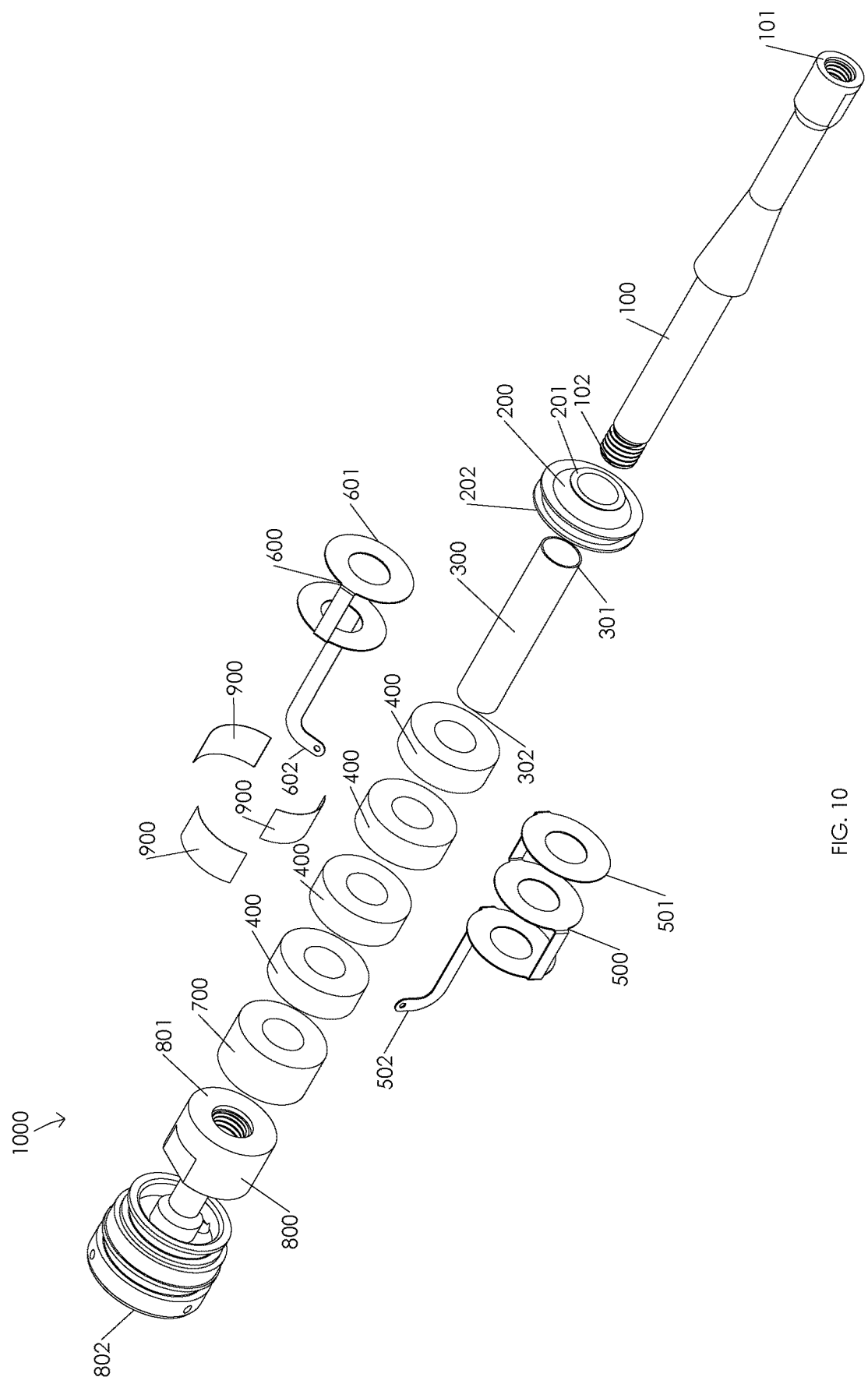
FIG. 10 is a schematic diagram illustrating an exploded view of a transducer assembly.

FIG. 10 is a schematic diagram illustrating an exploded view of a transducer assembly 1000. In one or more embodiments, a transducer assembly 1000 may comprise an amplifier 100, a flange 200, an amplifier sleeve 300, a first piezoelectric ring 400, a second piezoelectric ring 400, a third piezoelectric ring 400, a fourth piezoelectric ring 400, an outer electrode stack 500, an inner electrode stack 600, an inert ring 700, a connector block 800, a first electrical insulator 900, a second electrical insulator 900, and a third electrical insulator 900.

Illustratively, a geometry of outer electrode stack 500 may be configured for a transducer assembly 1000, e.g., by folding first medial electrical conductor 505 into a plane normal to first lateral electrical conductor 510. In one or more embodiments, a geometry of outer electrode stack 500 may be configured for a transducer assembly 1000, e.g., by folding third medial electrical conductor 515 into a plane normal to first lateral electrical conductor 510. Illustratively, a geometry of outer electrode stack 500 may be configured for a transducer assembly 1000, e.g., by folding third medial electrical conductor 515 into a plane parallel to first medial electrical conductor 505. In one or more embodiments, a geometry of outer electrode stack 500 may be configured for a transducer assembly 1000, e.g., by folding third lateral electrical conductor 520 into a plane normal to third medial electrical conductor 515. Illustratively, a geometry of outer electrode stack 500 may be configured for a transducer assembly 1000, e.g., by folding third lateral electrical conductor 520 into a plane normal to first medial electrical conductor 505. In one or more embodiments, a geometry of outer electrode stack 500 may be configured for a transducer assembly 1000, e.g., by folding third lateral electrical conductor 520 into a plane parallel to first lateral electrical conductor 510. Illustratively, a geometry of outer electrode stack 500 may be configured for a transducer assembly 1000, e.g., by folding fifth medial electrical conductor 525 into a plane normal to third lateral electrical conductor 520. In one or more embodiments, a geometry of outer electrode stack 500 may be configured for a transducer assembly 1000, e.g., by folding fifth medial electrical conductor 525 into a plane normal to first lateral electrical conductor 510. Illustratively, a geometry of outer electrode stack 500 may be configured for a transducer assembly 1000, e.g., by folding fifth medial electrical conductor 525 into a plane parallel to third medial electrical conductor 515. In one or more embodiments, a geometry of outer electrode stack 500 may be configured for a transducer assembly 1000, e.g., by folding fifth medial electrical conductor 525 into a plane parallel to first medial electrical conductor 505. Illustratively, a geometry of outer electrode stack 500 may be configured for a transducer assembly 1000, e.g., by folding first lead 530 into a plane normal to fifth medial electrical conductor 525. In one or more embodiments, a geometry of outer electrode stack 500 may be configured for a transducer assembly 1000, e.g., by folding first lead 530 into a plane normal to third medial electrical conductor 515. Illustratively, a geometry of outer electrode stack 500 may be configured for a transducer assembly 1000, e.g., by folding first lead 530 into a plane normal to first medial electrical conductor 505. In one or more embodiments, a geometry of outer electrode stack 500 may be configured for a transducer assembly 1000, e.g., by folding first lead 530 into a plane parallel to third lateral electrical conductor 520. Illustratively, a geometry of outer electrode stack 500 may be configured for a transducer assembly 1000, e.g., by folding first lead 530 into a plane parallel to first lateral electrical conductor 510. In one or more embodiments, a geometry of outer electrode stack 500 may be configured for a transducer assembly 1000, e.g., by folding first lead 530 into a plane coplanar with first lateral electrical conductor 510.

Illustratively, a geometry of inner electrode stack 600 may be configured for a transducer assembly 1000, e.g., by folding second medial electrical conductor 605 into a plane normal to second lateral electrical conductor 610. In one or more embodiments, a geometry of inner electrode stack 600 may be configured for a transducer assembly 1000, e.g., by folding fourth medical electrical conductor 615 into a plane normal to second lateral electrical conductor 610. Illustratively, a geometry of inner electrode stack 600 may be configured for a transducer assembly 1000, e.g., by folding fourth medical electrical conductor 615 into a plane parallel to second medial electrical conductor 605. In one or more embodiments, a geometry of inner electrode stack 600 may be configured for a transducer assembly 1000, e.g., by folding second lead 620 into a plane normal to fourth medial electrical conductor 610. Illustratively, a geometry of inner electrode stack 600 may be configured for a transducer assembly 1000, e.g., by folding second lead 620 into a plane normal to second medial electrical conductor 605. In one or more embodiments, a geometry of inner electrode stack 600 may be configured for a transducer assembly 1000, e.g., by folding second lead 620 into a plane parallel to second lateral electrical conductor 610.

FIGS. 11A, 11B, and 11C are schematic diagrams illustrating an assembled transducer 1100. FIG. 11A illustrates a top view of an assembled transducer 1100. FIG. 11B illustrates a side view of an assembled transducer 1100. FIG. 11C illustrates a crosssectional view in a sagittal plane of an assembled transducer 1100. In one or more embodiments, an assembled transducer 1100 may comprise an assembled transducer distal end 1101 and an assembled transducer proximal end 1102. Illustratively, assembled transducer 1100 may comprise a composite transducer, e.g., assembled transducer 1100 may comprise a mechanically prestressed composite transducer.

In one or more embodiments, amplifier sleeve 300 may be disposed over a portion of amplifier 100, e.g., amplifier sleeve 300 may be disposed over proximal base 105. Illustratively, amplifier sleeve 300 may be disposed over a portion of amplifier 100 wherein amplifier sleeve distal end 301 is adjacent to flange interface taper proximal end 112, e.g., amplifier sleeve 300 may be disposed over a portion of amplifier 100 wherein amplifier sleeve distal end 301 abuts flange interface taper proximal end 112. In one or more embodiments, amplifier sleeve 300 may be disposed over a portion of amplifier 100 wherein amplifier sleeve distal end 301 is adjacent to proximal base distal end 106, e.g., amplifier sleeve 300 may be disposed over a portion of amplifier 100 wherein amplifier sleeve distal end 301 abuts proximal base distal end 106. Illustratively, amplifier sleeve 300 may be disposed over a portion of amplifier 100 wherein amplifier sleeve distal end 301 is coplanar with proximal base distal end 106. In one or more embodiments, amplifier sleeve 300 may be disposed over a portion of amplifier 100 wherein amplifier sleeve proximal end 302 is disposed distally of proximal base proximal end 107, e.g., amplifier sleeve 300 may be disposed over a portion of amplifier 100 wherein amplifier sleeve proximal end 302 is disposed distally of amplifier proximal thread 103.

Illustratively, flange 200 may be disposed over a portion of amplifier 100, e.g., flange 200 may be disposed over proximal base 105. In one or more embodiments, flange 200 may be disposed over a portion of amplifier sleeve 300. Illustratively, flange 200 may be disposed over a portion of amplifier 100 and amplifier sleeve 300, e.g., flange 200 may be disposed over a portion of amplifier 100 and amplifier sleeve 300 wherein proximal base 105 and amplifier sleeve 300 are disposed in flange inner bore 230. In one or more embodiments, a portion of amplifier sleeve 300 may be disposed between a portion of amplifier 100 and flange 200, e.g., a portion of amplifier sleeve 300 may be disposed between proximal base 105 and flange 200. Illustratively, flange 200 may be disposed over a portion of amplifier 100 wherein flange distal end 201 is adjacent to flange interface taper proximal end 112, e.g., flange 200 may be disposed over a portion of amplifier 100 wherein flange distal end 201 abuts flange interface taper proximal end 112. In one or more embodiments, flange 200 may be disposed over a portion of amplifier 100 wherein flange distal end 201 is adjacent to proximal base distal end 106, e.g., flange 200 may be disposed over a portion of amplifier 100 wherein flange distal end 201 abuts proximal base distal end 106. Illustratively, flange 200 may be disposed over a portion of amplifier 100 wherein flange distal end 201 is coplanar with proximal base distal end 106. In one or more embodiments, flange 200 may be disposed over a portion of amplifier sleeve 300 wherein flange distal end 201 is adjacent to amplifier sleeve distal end 301, e.g., flange 200 may be disposed over a portion of amplifier sleeve 300 wherein flange distal end 201 abuts amplifier sleeve distal end 301. Illustratively, flange 200 may be disposed over a portion of amplifier sleeve 300 wherein flange distal end 201 is coplanar with amplifier sleeve distal end 301. In one or more embodiments, flange 200 may be disposed over a portion of amplifier 100 and amplifier sleeve 300 wherein flange distal end 201 is adjacent to proximal base distal end 106 and amplifier sleeve distal end 301, e.g., flange 200 may be disposed over a portion of amplifier 100 and amplifier sleeve 300 wherein flange distal end 201 abuts proximal base distal end 106 and amplifier sleeve distal end 301. Illustratively, flange 200 may be disposed over a portion of amplifier 100 and amplifier sleeve 300 wherein flange distal end 201 is coplanar with proximal base distal end 106 and amplifier sleeve distal end 301.

In one or more embodiments, a portion of outer electrode stack 500 may be disposed over a portion of amplifier 100, e.g., first medial electrical conductor 505 may be disposed over a portion of amplifier 100 wherein proximal base 105 is disposed in first medial aperture 506. Illustratively, a portion of outer electrode stack 500 may be disposed over a portion of amplifier sleeve 300, e.g., first medial electrical conductor 505 may be disposed over a portion of amplifier sleeve 300 wherein the portion of amplifier sleeve is disposed in first medial aperture 506. In one or more embodiments, a portion of outer electrode stack 500 may be disposed over a portion of amplifier sleeve 300 and a portion of amplifier 100 wherein the portion of amplifier sleeve 300 and the portion of amplifier 100 are disposed in first medial aperture 506, e.g., first medial electrical conductor 505 may be disposed over a portion of amplifier sleeve 300 and a portion of amplifier 100 wherein the portion of amplifier sleeve 300 is disposed between the portion of amplifier 100 and first medial electrical conductor 505. Illustratively, a portion of outer electrode stack 500 may be disposed over amplifier sleeve 300 and amplifier 100 wherein first medial electrical conductor 505 is adjacent to flange proximal end 202, e.g., a portion of outer electrode stack 500 may be disposed over amplifier sleeve 300 and amplifier 100 wherein first medial electrical conductor 505 abuts flange proximal end 202.

In one or more embodiments, first piezoelectric ring 400 may be disposed over a portion of amplifier 100, e.g., first piezoelectric ring 400 may be disposed over a portion of amplifier 100 wherein proximal base 105 is disposed in first piezoelectric ring inner bore 411. Illustratively, first piezoelectric ring 400 may be disposed over a portion of amplifier sleeve 300, e.g., first piezoelectric ring 400 may be disposed over a portion of amplifier sleeve 300 wherein the portion of amplifier sleeve 300 is disposed in first piezoelectric ring inner bore 411. In one or more embodiments, first piezoelectric ring 400 may be disposed over a portion of amplifier sleeve 300 and a portion of amplifier 100 wherein the portion of amplifier sleeve 300 and the portion of amplifier 100 are disposed in first piezoelectric ring inner bore 411, e.g., first piezoelectric ring 400 may be disposed over a portion of amplifier sleeve 300 and a portion of amplifier 100 wherein the portion of amplifier sleeve 300 is disposed between the portion of amplifier 100 and first piezoelectric ring 400. Illustratively, first piezoelectric ring 400 may be disposed over amplifier sleeve 300 and amplifier 100 wherein first piezoelectric ring distal end 401 is adjacent to first medial electrical conductor 505, e.g., first piezoelectric ring 400 may be disposed over amplifier sleeve 300 and amplifier 100 wherein first piezoelectric ring distal end 401 abuts first medial electrical conductor 505. In one or more embodiments, first piezoelectric ring 400 may be disposed over amplifier sleeve 300 and amplifier 100 wherein first medial electrical conductor 505 is disposed between first piezoelectric ring 400 and flange 200, e.g., first piezoelectric ring 400 may be disposed over amplifier sleeve 300 and amplifier 100 wherein first medial electrical conductor 505 is disposed between first piezoelectric ring distal end 401 and flange proximal end 202.

Illustratively, a portion of inner electrode stack 600 may be disposed over a portion of amplifier 100, e.g., second medial electrical conductor 605 may be disposed over a portion of amplifier 100 wherein proximal base 105 is disposed in second medial aperture 606. In one or more embodiments, a portion of inner electrode stack 600 may be disposed over a portion of amplifier sleeve 300, e.g., second medial electrical conductor 605 may be disposed over a portion of amplifier sleeve 300 wherein the portion of amplifier sleeve 300 is disposed in second medial aperture 606. Illustratively, a portion of inner electrode stack 600 may be disposed over a portion of amplifier sleeve 300 and a portion of amplifier 100 wherein the portion of amplifier sleeve 300 and the portion of amplifier 100 are disposed in second medial aperture 606, e.g., second medial electrical conductor 605 may be disposed over a portion of amplifier sleeve 300 and a portion of amplifier 100 wherein the portion of amplifier sleeve 300 is disposed between the portion of amplifier 100 and second medial electrical conductor 605. In one or more embodiments, a portion of inner electrode stack 600 may be disposed over amplifier sleeve 300 and amplifier 100 wherein second medial electrical conductor 605 is adjacent to first piezoelectric ring proximal end 402, e.g., a portion of inner electrode stack 600 may be disposed over amplifier sleeve 300 and amplifier 100 wherein second medial electrical conductor 605 abuts first piezoelectric ring proximal end 402. Illustratively, second medial electrical conductor 605 may be disposed over amplifier sleeve 300 and amplifier 100 wherein first piezoelectric ring 400 is disposed between second medial electrical conductor 605 and first medial electrical conductor 505, e.g., second medial electrical conductor 605 may be disposed over amplifier sleeve 300 and amplifier 100 wherein first piezoelectric ring distal end 401 abuts first medial electrical conductor 505 and wherein first piezoelectric ring proximal end 402 abuts second medial electrical conductor 605.

In one or more embodiments, second piezoelectric ring 400 may be disposed over a portion of amplifier 100, e.g., second piezoelectric ring 400 may be disposed over a portion of amplifier 100 wherein proximal base 105 is disposed in second piezoelectric ring inner bore 411. Illustratively, second piezoelectric ring 400 may be disposed over a portion of amplifier sleeve 300, e.g., second piezoelectric ring 400 may be disposed over a portion of amplifier sleeve 300 wherein the portion of amplifier sleeve 300 is disposed in second piezoelectric ring inner bore 411. In one or more embodiments, second piezoelectric ring 400 may be disposed over a portion of amplifier sleeve 300 and a portion of amplifier 100 wherein the portion of amplifier sleeve 300 and the portion of amplifier 100 are disposed in second piezoelectric ring inner bore 411, e.g., second piezoelectric ring 400 may be disposed over a portion of amplifier sleeve 300 and a portion of amplifier 100 wherein the portion of amplifier sleeve 300 is disposed between the portion of amplifier 100 and second piezoelectric ring 400. Illustratively, second piezoelectric ring 400 may be disposed over amplifier sleeve 300 and amplifier 100 wherein second piezoelectric ring proximal end 402 is adjacent to second medial electrical conductor 605, e.g., second piezoelectric ring 400 may be disposed over amplifier sleeve 300 and amplifier 100 wherein second piezoelectric ring proximal end 402 abuts second medial electrical conductor 605. In one or more embodiments, second piezoelectric ring 400 may be disposed over amplifier sleeve 300 and amplifier 100 wherein second medial electrical conductor 605 is disposed between first piezoelectric ring 400 and second piezoelectric ring 400, e.g., second piezoelectric ring 400 may be disposed over amplifier sleeve 300 and amplifier 100 wherein second medial electrical conductor 605 is disposed between first piezoelectric ring proximal end 402 and second piezoelectric ring proximal end 402.

Illustratively, a portion of outer electrode stack 500 may be disposed over a portion of amplifier 100, e.g., third medial electrical conductor 515 may be disposed over a portion of amplifier 100 wherein proximal base 105 is disposed in third medial aperture 516. In one or more embodiments, a portion of outer electrode stack 500 may be disposed over a portion of amplifier sleeve 300, e.g., third medial electrical conductor 515 may be disposed over a portion of amplifier sleeve 300 wherein the portion of amplifier sleeve 300 is disposed in third medial aperture 516. Illustratively, a portion of outer electrode stack 500 may be disposed over a portion of amplifier sleeve 300 and a portion of amplifier 100 wherein the portion of amplifier sleeve 300 and the portion of amplifier 100 are disposed in third medial aperture 516, e.g., third medial electrical conductor 515 may be disposed over a portion of amplifier sleeve 300 and a portion of amplifier 100 wherein the portion of amplifier sleeve 300 is disposed between the portion of amplifier 100 and third medial electrical conductor 515. In one or more embodiments, a portion of outer electrode stack 500 may be disposed over amplifier sleeve 300 and amplifier 100 wherein third medial electrical conductor 515 is adjacent to second piezoelectric ring distal end 401, e.g., a portion of outer electrode stack 500 may be disposed over amplifier sleeve 300 and amplifier 100 wherein third medial electrical conductor 515 abuts second piezoelectric ring distal end 401. Illustratively, third medial electrical conductor 515 may be disposed over amplifier sleeve 300 and amplifier 100 wherein second piezoelectric ring 400 is disposed between second medial electrical conductor 605 and third medial electrical conductor 515, e.g., third medial electrical conductor 515 may be disposed over amplifier sleeve 300 and amplifier 100 wherein second piezoelectric ring distal end 401 abuts third medial electrical conductor 515 and wherein second piezoelectric ring proximal end 402 abuts second medial electrical conductor 605.

In one or more embodiments, third piezoelectric ring 400 may be disposed over a portion of amplifier 100, e.g., third piezoelectric ring 400 may be disposed over a portion of amplifier 100 wherein proximal base 105 is disposed in third piezoelectric ring inner bore 411. Illustratively, third piezoelectric ring 400 may be disposed over a portion of amplifier sleeve 300, e.g., third piezoelectric ring 400 may be disposed over a portion of amplifier sleeve 300 wherein the portion of amplifier sleeve 300 is disposed in third piezoelectric ring inner bore 411. In one or more embodiments, third piezoelectric ring 400 may be disposed over a portion of amplifier sleeve 300 and a portion of amplifier 100 wherein the portion of amplifier sleeve 300 and the portion of amplifier 100 are disposed in third piezoelectric ring inner bore 411, e.g., third piezoelectric ring 400 may be disposed over a portion of amplifier sleeve 300 and a portion of amplifier 100 wherein the portion of amplifier sleeve 300 is disposed between the portion of amplifier 100 and third piezoelectric ring 400. Illustratively, third piezoelectric ring 400 may be disposed over amplifier sleeve 300 and amplifier 100 wherein third piezoelectric ring distal end 401 is adjacent to third medial electrical conductor 515, e.g., third piezoelectric ring 400 may be disposed over amplifier sleeve 300 and amplifier 100 wherein third piezoelectric ring distal end 401 abuts third medial electrical conductor 515. In one or more embodiments, third piezoelectric ring 400 may be disposed over amplifier sleeve 300 and amplifier 100 wherein third medial electrical conductor 515 is disposed between second piezoelectric ring 400 and third piezoelectric ring 400, e.g., third piezoelectric ring 400 may be disposed over amplifier sleeve 300 and amplifier 100 wherein third medial electrical conductor 515 is disposed between second piezoelectric ring distal end 401 and third piezoelectric ring distal end 401.

Illustratively, a portion of inner electrode stack 600 may be disposed over a portion of amplifier 100, e.g., fourth medial electrical conductor 615 may be disposed over a portion of amplifier 100 wherein proximal base 105 is disposed in fourth medial aperture 616. In one or more embodiments, a portion of inner electrode stack 600 may be disposed over a portion of amplifier sleeve 300, e.g., fourth medial electrical conductor 615 may be disposed over a portion of amplifier sleeve 300 wherein the portion of amplifier sleeve 300 is disposed in fourth medial aperture 616. Illustratively, a portion of inner electrode stack 600 may be disposed over a portion of amplifier sleeve 300 and a portion of amplifier 100 wherein the portion of amplifier sleeve 300 and the portion of amplifier 100 are disposed in fourth medial aperture 616, e.g., fourth medial electrical conductor 615 may be disposed over a portion of amplifier sleeve 300 and a portion of amplifier 100 wherein the portion of amplifier sleeve 300 is disposed between the portion of amplifier 100 and fourth medial electrical conductor 615. In one or more embodiments, a portion of inner electrode stack 600 may be disposed over amplifier sleeve 300 and amplifier 100 wherein fourth medial electrical conductor 615 is adjacent to third piezoelectric ring proximal end 402, e.g., a portion of inner electrode stack 600 may be disposed over amplifier sleeve 300 and amplifier 100 wherein fourth medial electrical conductor 615 abuts third piezoelectric ring proximal end 402. Illustratively, fourth medial electrical conductor 615 may be disposed over amplifier sleeve 300 and amplifier 100 wherein third piezoelectric ring 400 is disposed between fourth medial electrical conductor 615 and third medial electrical conductor 515, e.g., fourth medial electrical conductor 615 may be disposed over amplifier sleeve 300 and amplifier 100 wherein third piezoelectric ring distal end 401 abuts third medial electrical conductor 515 and wherein third piezoelectric ring proximal end 402 abuts fourth medial electrical conductor 615.

In one or more embodiments, fourth piezoelectric ring 400 may be disposed over a portion of amplifier 100, e.g., fourth piezoelectric ring 400 may be disposed over a portion of amplifier 100 wherein proximal base 105 is disposed in fourth piezoelectric ring inner bore 411. Illustratively, fourth piezoelectric ring 400 may be disposed over a portion of amplifier sleeve 300, e.g., fourth piezoelectric ring 400 may be disposed over a portion of amplifier sleeve 300 wherein the portion of amplifier sleeve 300 is disposed in fourth piezoelectric ring inner bore 411. In one or more embodiments, fourth piezoelectric ring 400 may be disposed over a portion of amplifier sleeve 300 and a portion of amplifier 100 wherein the portion of amplifier sleeve 300 and the portion of amplifier 100 are disposed in fourth piezoelectric ring inner bore 411, e.g., fourth piezoelectric ring 400 may be disposed over a portion of amplifier sleeve 300 and a portion of amplifier 100 wherein the portion of amplifier sleeve 300 is disposed between the portion of amplifier 100 and fourth piezoelectric ring 400. Illustratively, fourth piezoelectric ring 400 may be disposed over amplifier sleeve 300 and amplifier 100 wherein fourth piezoelectric ring proximal end 402 is adjacent to fourth medial electrical conductor 615, e.g., fourth piezoelectric ring 400 may be disposed over amplifier sleeve 300 and amplifier 100 wherein fourth piezoelectric ring proximal end 402 abuts fourth medial electrical conductor 615. In one or more embodiments, fourth piezoelectric ring 400 may be disposed over amplifier sleeve 300 and amplifier 100 wherein fourth medial electrical conductor 615 is disposed between fourth piezoelectric ring 400 and third piezoelectric ring 400, e.g., fourth piezoelectric ring 400 may be disposed over amplifier sleeve 300 and amplifier 100 wherein fourth medial electrical conductor 615 is disposed between third piezoelectric ring proximal end 402 and fourth piezoelectric ring proximal end 402.

Illustratively, a portion of outer electrode stack 500 may be disposed over a portion of amplifier 100, e.g., fifth medial electrical conductor 525 may be disposed over a portion of amplifier 100 wherein proximal base 105 is disposed in fifth medial aperture 526. In one or more embodiments, a portion of outer electrode stack 500 may be disposed over a portion of amplifier sleeve 300, e.g., fifth medial electrical conductor 525 may be disposed over a portion of amplifier sleeve 300 wherein the portion of amplifier sleeve 300 is disposed in fifth medial aperture 526. Illustratively, a portion of outer electrode stack 500 may be disposed over a portion of amplifier sleeve 300 and a portion of amplifier 100 wherein the portion of amplifier sleeve 300 and the portion of amplifier 100 are disposed in fifth medial aperture 526, e.g., fifth medial electrical conductor 525 may be disposed over a portion of amplifier sleeve 300 and a portion of amplifier 100 wherein the portion of amplifier sleeve 300 is disposed between the portion of amplifier 100 and fifth medial electrical conductor 525. In one or more embodiments, a portion of outer electrode stack 500 may be disposed over amplifier sleeve 300 and amplifier 100 wherein fifth medial electrical conductor 525 is adjacent to fourth piezoelectric ring distal end 401, e.g., a portion of outer electrode stack 500 may be disposed over amplifier sleeve 300 and amplifier 100 wherein fifth medial electrical conductor 525 abuts fourth piezoelectric ring distal end 401. Illustratively, fifth medial electrical conductor 525 may be disposed over amplifier sleeve 300 and amplifier 100 wherein fourth piezoelectric ring 400 is disposed between fourth medial electrical conductor 615 and fifth medial electrical conductor 525, e.g., fifth medial electrical conductor 525 may be disposed over amplifier sleeve 300 and amplifier 100 wherein fourth piezoelectric ring distal end 401 abuts fifth medial electrical conductor 525 and wherein fourth piezoelectric ring proximal end 402 abuts fourth medial electrical conductor 615.

In one or more embodiments, inert ring 700 may be disposed over a portion of amplifier 100, e.g., inert ring 700 may be disposed over a portion of amplifier 100 wherein proximal base 105 is disposed in inert ring inner bore 711. Illustratively, inert ring 700 may be disposed over a portion of amplifier sleeve 300, e.g., inert ring 700 may be disposed over a portion of amplifier sleeve 300 wherein the portion of amplifier sleeve 300 is disposed in inert ring inner bore 711. In one or more embodiments, inert ring 700 may be disposed over a portion of amplifier sleeve 300 and a portion of amplifier 100 wherein the portion of amplifier sleeve 300 and the portion of amplifier 100 are disposed in inert ring inner bore 711, e.g., inert ring 700 may be disposed over a portion of amplifier sleeve 300 and a portion of amplifier 100 wherein the portion of amplifier sleeve 300 is disposed between the portion of amplifier 100 and inert ring 700. Illustratively, inert ring 700 may be disposed over amplifier sleeve 300 and amplifier 100 wherein amplifier sleeve proximal end 302 is disposed in inert ring inner bore 711, e.g., inert ring 700 may be disposed over amplifier sleeve 300 and amplifier 100 wherein proximal base proximal end 107 is disposed in inert ring inner bore 711. In one or more embodiments, inert ring 700 may be disposed over amplifier sleeve 300 and amplifier 100 wherein a portion of amplifier proximal undercut 104 is disposed in inert ring inner bore 711. Illustratively, inert ring 700 may be disposed over amplifier sleeve 300 and amplifier 100 wherein inert ring distal end 701 is adjacent to fifth medial electrical conductor 525, e.g., inert ring 700 may be disposed over amplifier sleeve 300 and amplifier 100 wherein inert ring distal end 701 abuts fifth medial electrical conductor 525. In one or more embodiments, inert ring 700 may be disposed over amplifier sleeve 300 and amplifier 100 wherein fifth medial electrical conductor 525 is disposed between fourth piezoelectric ring 400 and inert ring 700, e.g., inert ring 700 may be disposed over amplifier sleeve 300 and amplifier 100 wherein fifth medial electrical conductor 525 is disposed between fourth piezoelectric ring distal end 401 and inert ring distal end 701.

Illustratively, first electrical insulator 900 may be disposed between first lateral electrical conductor 510 and first piezoelectric ring 400, e.g., first electrical insulator 900 may be configured to electrically isolate first lateral electrical conductor 510 and first piezoelectric ring 400. In one or more embodiments, first electrical insulator 900 may be disposed between first lateral electrical conductor 510 and second medial electrical conductor 605, e.g., first electrical insulator 900 may be configured to electrically isolate first lateral electrical conductor 510 and second medial electrical conductor 605. Illustratively, first electrical insulator 900 may be disposed between first lateral electrical conductor 510 and second piezoelectric ring 400, e.g., first electrical insulator 900 may be configured to electrically isolate first lateral electrical conductor 510 and second piezoelectric ring 400.

In one or more embodiments, second electrical insulator 900 may be disposed between second lateral electrical conductor 610 and second piezoelectric ring 400, e.g., second electrical insulator 900 may be configured to electrically isolate second lateral electrical conductor 610 and second piezoelectric ring 400. Illustratively, second electrical insulator 900 may be disposed between second lateral electrical conductor 610 third medial electrical conductor 515, e.g., second electrical insulator 900 may be configured to electrically isolate second lateral electrical conductor 610 and third medial electrical conductor 515. In one or more embodiments, second electrical insulator 900 may be disposed between second lateral electrical conductor 610 and third piezoelectric ring 400, e.g., second electrical insulator 900 may be configured to electrically isolate second lateral electrical conductor 610 and third piezoelectric ring 400.

Illustratively, third electrical insulator 900 may be disposed between third lateral electrical conductor 520 and third piezoelectric ring 400, e.g., third electrical insulator 900 may be configured to electrically isolate third lateral electrical conductor 520 and third piezoelectric ring 400. In one or more embodiments, third electrical insulator 900 may be disposed between third lateral electrical conductor 520 and fourth medial electrical conductor 615, e.g., third electrical insulator 900 may be configured to electrically isolate third lateral electrical conductor 520 and fourth medial electrical conductor 615. Illustratively, third electrical insulator 900 may be disposed between third lateral electrical conductor 520 and fourth piezoelectric ring 400, e.g., third electrical insulator 900 may be configured to electrically isolate third lateral electrical conductor 520 and fourth piezoelectric ring 400.

In one or more embodiments, a portion of connector block 800 may be disposed over a portion of amplifier 100, e.g., a portion of connector block 800 may be disposed over amplifier proximal end 102. Illustratively, a portion of connector block 800 may be disposed over a portion of amplifier 100 wherein a portion of connector block distal undercut 832 may be disposed over a portion of amplifier proximal undercut 104. In one or more embodiments, a portion of connector block 800 may be disposed over a portion of amplifier 100 wherein amplifier proximal end 102 may be disposed in amplifier housing 833, e.g., a portion of connector block 800 may be disposed over a portion of amplifier 100 wherein amplifier proximal end 102 may be disposed in amplifier housing taper 834. Illustratively, a portion of connector block 800 may be disposed over amplifier proximal thread 103, e.g., connector block distal thread 831 may be disposed over amplifier proximal thread 103. In one or more embodiments, amplifier proximal thread 103 may comprise an external thread and connector block distal thread 831 may comprise an internal thread, e.g., connector block distal thread 831 and amplifier proximal thread 103 may be configured to convert a torque into a linear force. Illustratively, amplifier proximal thread 103 may comprise an internal thread and connector block distal thread 831 may comprise an external thread, e.g., amplifier proximal thread 103 and connector block distal thread 831 may be configured to convert a torque into a linear force. In one or more embodiments, a portion of amplifier 100 may be disposed in a portion of connector block 800 wherein a portion of connector block 800 is adjacent to a portion of inert ring 700, e.g., a portion of amplifier 100 may be disposed in a portion of connector block 800 wherein a portion of connector block 800 abuts a portion of inert ring 700. Illustratively, a portion of amplifier 100 may be disposed in a portion of connector block 800 wherein connector block distal end 801 is adjacent to inert ring proximal end 702, e.g., a portion of amplifier 100 may be disposed in a portion of connector block 800 wherein connector block distal end 801 abuts inert ring proximal end 702. In one or more embodiments, a portion of amplifier 100 may be disposed in a portion of connector block 800 wherein the portion of amplifier 100 is fixed in the portion of connector block 800, e.g., the portion of amplifier 100 may be fixed in the portion of connector block 800 by a force of friction. Illustratively, a portion of amplifier proximal thread 103 may be disposed in a portion of connector block distal thread 831 wherein the portion of amplifier proximal thread 103 is fixed in the portion of connector block distal thread 831, e.g., the portion of amplifier proximal thread 103 may be fixed in the portion of connector block distal thread 831 by a force of friction. In one or more embodiments, a portion of amplifier 100 may be fixed in a portion of connector block 800 by any suitable fixation means, e.g., a portion of amplifier 100 may be fixed in a portion of connector block 800 by an interference fit, a weld, an adhesive, and epoxy, a crimp, a tie, a pin, etc.

Illustratively, disposing amplifier proximal end 102 beyond a particular distance in connector block 800 may be configured to compress a portion of assembled transducer 1100, e.g., disposing amplifier proximal end 102 beyond a particular distance in connector block 800 may be configured to compress a portion of assembled transducer 1100 disposed between connector block distal end 801 and flange interface taper proximal end 112. In one or more embodiments, disposing amplifier proximal end 102 beyond a particular distance in connector block 800 may be configured to apply a force vector to inert ring proximal end 702, e.g., disposing amplifier proximal end 102 beyond a particular distance in connector block 800 may be configured to apply a force vector to inert ring proximal end 702 wherein the force vector is directed towards assembled transducer distal end 1101 and away from assembled transducer proximal end 1102. Illustratively, disposing amplifier proximal end 102 beyond a particular distance in connector block 800 may be configured to apply a force vector to flange distal end 201, e.g., disposing amplifier proximal end 102 beyond a particular distance in connector block 800 may be configured to apply a force vector to flange distal end 201 wherein the force vector is directed towards assembled transducer proximal end 1102 and away from assembled transducer distal end 1101.

In one or more embodiments, disposing amplifier proximal end 102 a first distance beyond a particular distance in connector block 800 may be configured to apply a first force vector to inert ring proximal end 702 wherein the first force vector has a first magnitude. Illustratively, disposing amplifier proximal end 102 a second distance beyond the particular distance in connector block 800 may be configured to apply a second force vector to inert ring proximal end 702 wherein the second force vector has a second magnitude. In one or more embodiments, the second distance beyond the particular distance in connector block 800 may be greater than the first distance beyond the particular distance in connector block 800 and the second magnitude may be greater than the first magnitude.

Illustratively, compressing a portion of assembled transducer 1100 disposed between connector block distal end 801 and flange interface taper proximal end 112 may be configured to increase a contact area between a first surface and a second surface of assembled transducer 1100. In one or more embodiments, compressing a portion of assembled transducer 1100 disposed between connector block distal end 801 and flange interface taper proximal end 112 may be configured to increase a contact area between connector block distal end 801 and inert ring proximal end 702. Illustratively, compressing a portion of assembled transducer 1100 disposed between connector block distal end 801 and flange interface taper proximal end 112 may be configured to increase a contact area between inert ring distal end 701 and fifth medial electrical conductor 525. In one or more embodiments, compressing a portion of assembled transducer 1100 disposed between connector block distal end 801 and flange interface taper proximal end 112 may be configured to increase a contact area between fifth medial electrical conductor 525 and fourth piezoelectric ring distal end 401. Illustratively, compressing a portion of assembled transducer 1100 disposed between connector block distal end 801 and flange interface taper proximal end 112 may be configured to increase a contact area between fourth piezoelectric ring proximal end 402 and fourth medial electrical conductor 615. In one or more embodiments, compressing a portion of assembled transducer 1100 disposed between connector block distal end 801 and flange interface taper proximal end 112 may be configured to increase a contact area between fourth medial electrical conductor 615 and third piezoelectric ring proximal end 402. Illustratively, compressing a portion of assembled transducer 1100 disposed between connector block distal end 801 and flange interface taper proximal end 112 may be configured to increase a contact area between third piezoelectric ring distal end 401 and third medial electrical conductor 515. In one or more embodiments, compressing a portion of assembled transducer 1100 disposed between connector block distal end 801 and flange interface taper proximal end 112 may be configured to increase a contact area between third medial electrical conductor 515 and second piezoelectric ring distal end 401. Illustratively, compressing a portion of assembled transducer 1100 disposed between connector block distal end 801 and flange interface taper proximal end 112 may be configured to increase a contact area between second piezoelectric ring proximal end 402 and second medial electrical conductor 605. In one or more embodiments, compressing a portion of assembled transducer 1100 disposed between connector block distal end 801 and flange interface taper proximal end 112 may be configured to increase a contact area between second medial electrical conductor 605 and first piezoelectric ring proximal end 402. Illustratively, compressing a portion of assembled transducer 1100 disposed between connector block distal end 801 and flange interface taper proximal end 112 may be configured to increase a contact area between first piezoelectric ring distal end 401 and first medial electrical conductor 505. In one or more embodiments, compressing a portion of assembled transducer 1100 disposed between connector block distal end 801 and flange interface taper proximal end 112 may be configured to increase a contact area between first medial electrical conductor 505 and flange proximal end 202. Illustratively, compressing a portion of assembled transducer 1100 disposed between connector block distal end 801 and flange interface taper proximal end 112 may be configured to increase a contact area between flange distal end 201 and flange interface taper proximal end 112.

In one or more embodiments, assembled transducer 1100 may be assembled by disposing amplifier proximal end 102 a first distance in connector block 800, applying a compressive force to a portion of assembled transducer 1100 disposed between connector block distal end 801 and flange interface taper proximal end 112, and disposing amplifier proximal end 102 a second distance in connector block 800 wherein the second distance is greater than the first distance, e.g., a force of friction between amplifier proximal thread 103 and connector block distal thread 831 may be configured to prevent a compressed assembled transducer 1100 from decompressing when amplifier proximal end 102 is disposed the second distance in connector block 800. Illustratively, assembled transducer 1100 may be assembled by applying a compressive force in a range of 550 to 2550 pounds to a portion of assembled transducer 1100 disposed between connector block distal end 801 and flange interface taper proximal end 112, e.g., assembled transducer 1100 may be assembled by applying a compressive force of 2000 pounds to a portion of assembled transducer 1100 disposed between connector block distal end 801 and flange interface taper proximal end 112. In one or more embodiments, assembled transducer 1100 may be assembled by applying a compressive force of less than 550 pounds or greater than 2550 pounds to a portion of assembled transducer 1100 disposed between connector block distal end 801 and flange interface taper proximal end 112. Illustratively, assembled transducer 1100 may be assembled by applying a compressive force of at least 500 pounds to a portion of assembled transducer 1100 disposed between connector block distal end 801 and flange interface taper proximal end 112. In one or more embodiments, assembled transducer 1100 may be assembled by applying a compressive force of at least 750 pounds to a portion of assembled transducer 1100 disposed between connector block distal end 801 and flange interface taper proximal end 112. Illustratively, assembled transducer 1100 may be assembled by applying a compressive force of at least 1000 pounds to a portion of assembled transducer 1100 disposed between connector block distal end 801 and flange interface taper proximal end 112. In one or more embodiments, assembled transducer 1100 may be assembled by applying a compressive force of at least 1250 pounds to a portion of assembled transducer 1100 disposed between connector block distal end 801 and flange interface taper proximal end 112. Illustratively, assembled transducer 1100 may be assembled by applying a compressive force of at least 1500 pounds to a portion of assembled transducer 1100 disposed between connector block distal end 801 and flange interface taper proximal end 112. In one or more embodiments, assembled transducer 1100 may be assembled by applying a compressive force of at least 1750 pounds to a portion of assembled transducer 1100 disposed between connector block distal end 801 and flange interface taper proximal end 112. Illustratively, assembled transducer 1100 may be assembled by applying a compressive force of at least 2000 pounds to a portion of assembled transducer 1100 disposed between connector block distal end 801 and flange interface taper proximal end 112.

Figure 12A:
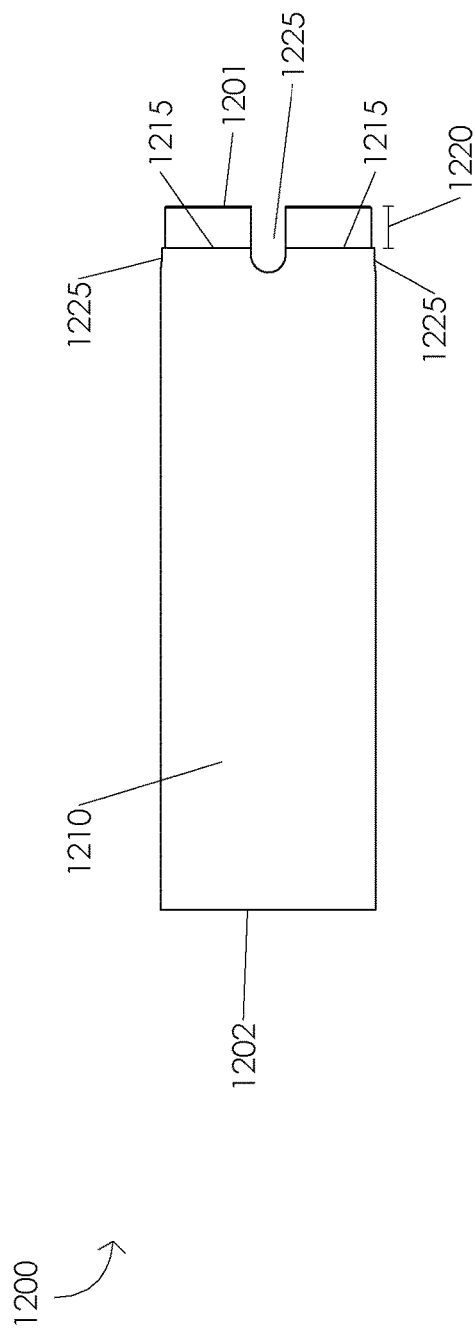
FIGS. 12A and 12B are schematic diagrams illustrating a transducer sleeve.
Figure 12B:
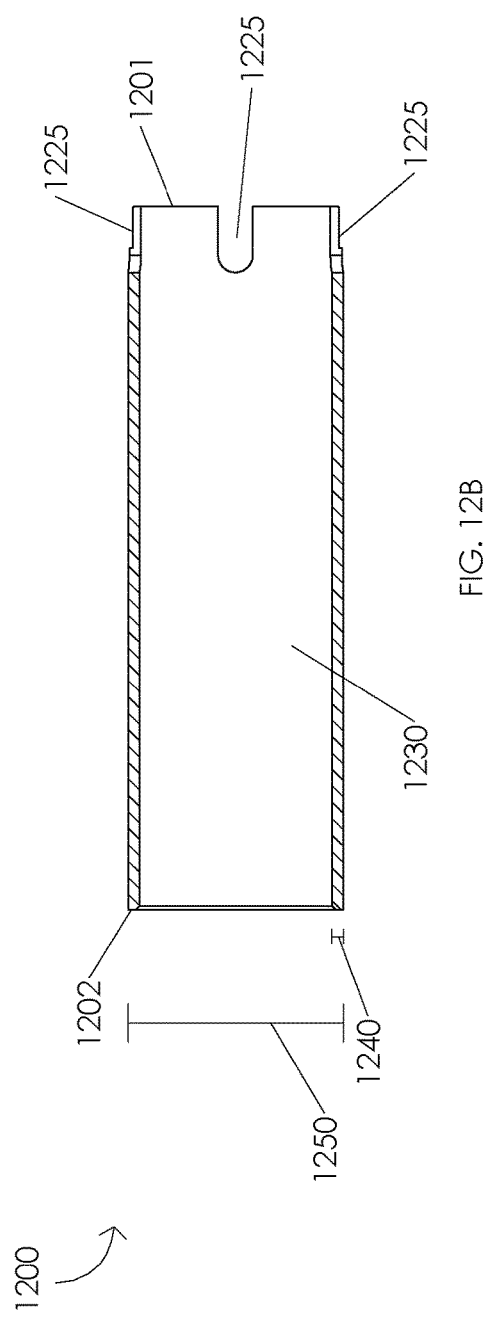

FIGS. 12A and 12B are schematic diagrams illustrating a transducer sleeve 1200. FIG. 12A illustrates a side view of a transducer sleeve 1200. FIG. 12B illustrates a crosssectional view in a sagittal plane of a transducer sleeve 1200. In one or more embodiments, a transducer sleeve 1200 may comprise a transducer sleeve distal end 1201 and a transducer sleeve proximal end 1202. Illustratively, transducer sleeve 1200 may comprise a transducer sleeve base 1210. In one or more embodiments, transducer sleeve 1200 may comprise a nosecone interface 1215. Illustratively, transducer sleeve 1200 may comprise a nosecone mount 1220. In one or more embodiments, transducer sleeve 1200 may comprise a distal aperture 1225, e.g., transducer sleeve 1200 may comprise a plurality of distal apertures 1225. Illustratively, transducer sleeve 1200 may comprise a transducer sleeve inner bore 1230. In one or more embodiments, transducer sleeve 1200 may have a transducer sleeve wall thickness 1240. Illustratively, transducer sleeve wall thickness 1240 may be a distance in a range of 0.0215 to 0.0765 inches, e.g., transducer sleeve wall thickness 1200 may be a distance of 0.0585 inches. In one or more embodiments, transducer wall thickness 1200 may be a distance of less than 0.0215 inches or greater than 0.0765 inches. Illustratively, transducer sleeve 1200 may have a transducer sleeve inner diameter 1250. In one or more embodiments, transducer sleeve inner diameter 1250 may be a distance in a range of 0.4215 to 0.7875 inches, e.g., transducer sleeve inner diameter 1250 may be a distance of 0.6875 inches. Illustratively, transducer sleeve inner diameter 1250 may be a distance of less than 0.4215 inches or greater than 0.7875 inches. In one or more embodiments, transducer sleeve 1200 may be manufactured from any suitable material, e.g., polymers, metals, metal alloys, etc., or from any combination of suitable materials. Illustratively, transducer sleeve 1200 may be manufactured from an electrical insulator material. In one or more embodiments, transducer sleeve 1200 may be manufactured from a thermoplastic polymer material, e.g., transducer sleeve 1200 may be manufactured from polyether ether ketone, polysulfone, poly(methyl methacrylate), acrylonitrile butadiene styrene, polylactide, polycarbonate, polybenzimidazole, polyetherether ketone, polyoxymethylene, polyether sulfone, polyetherimide, polyethylene, polyphenylene sulfide, polyphenylene oxide, polyvinyl chloride, polytetrafluoroethylene, polypropylene, polystyrene, etc.

Figure 13A:
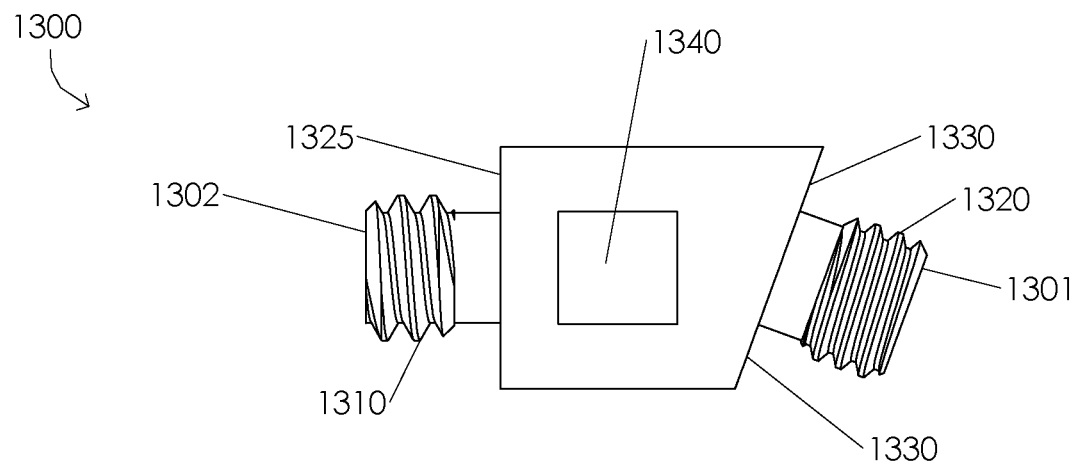
FIGS. 13A and 13B are schematic diagrams illustrating an angled adaptor.
Figure 13B:
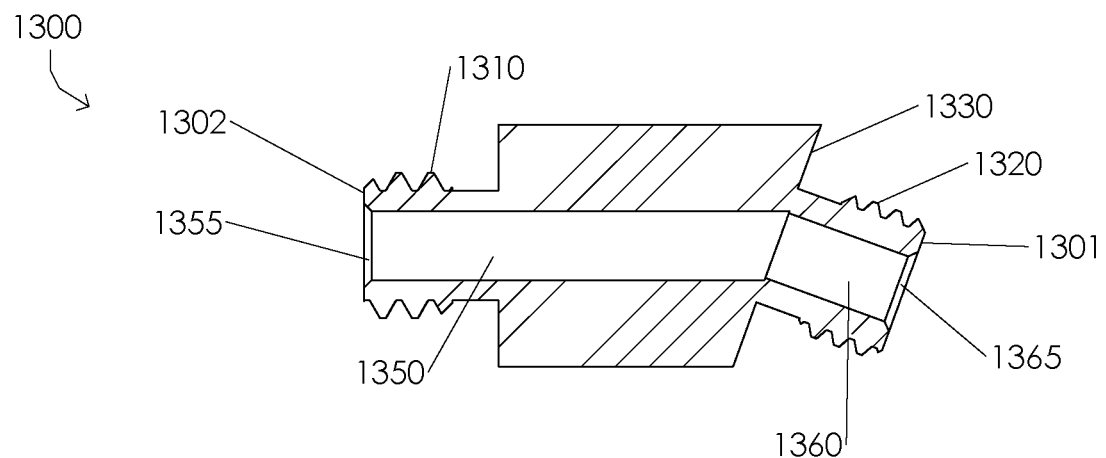

FIGS. 13A and 13B are schematic diagrams illustrating an angled adaptor 1300. FIG. 13A illustrates a side view of an angled adaptor 1300. FIG. 13B illustrates a crosssectional view in a sagittal plane of an angled adaptor 1300. In one or more embodiments, an angled adaptor 1300 may comprise an angled adaptor distal end 1301 and an angled adaptor proximal end 1302. Illustratively, angled adaptor 1300 may comprise an angled adaptor proximal thread 1310. In one or more embodiments, angled adaptor 1300 may comprise an angled adaptor distal thread 1320. Illustratively, angled adaptor 1300 may comprise an amplifier interface 1325. In one or more embodiments, angled adaptor 1300 may comprise an angled tip interface 1330. Illustratively, angled adaptor 1300 may comprise an angled adaptor tool interface 1340. In one or more embodiments, angled adaptor 1300 may comprise a medial inner bore 1350. Illustratively, angled adaptor 1300 may comprise a medial inner bore proximal bevel 1355. In one or more embodiments, angled adaptor 1300 may comprise an angled inner bore 1360. Illustratively, angled adaptor 1300 may comprise an angled inner bore distal bevel 1365.

In one or more embodiments, angled adaptor tool interface 1340 may be disposed between amplifier interface 1325 and angled tip interface 1300. Illustratively, angled adaptor tool interface 1340 may be disposed between angled adaptor proximal thread 1310 and angled adaptor distal thread 1320. In one or more embodiments, angled adaptor distal thread 1320 may be disposed between angled tip interface 1330 and angled adaptor distal end 1301. Illustratively, angled adaptor proximal thread 1310 may be disposed between amplifier interface 1325 and angled adaptor proximal end 1302.

In one or more embodiments, angled adaptor 1300 may be manufactured from any suitable material, e.g., polymers, metals, metal alloys, etc., or from any combination of suitable materials. Illustratively, angled adaptor 1300 may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, etc. For example, angled adaptor 1300 may be manufactured from a stainless steel, a brass, a bronze, a duralumin, a nitinol, etc. Illustratively, angled adaptor 1300 may be manufactured from an underdamped material. In one or more embodiments, angled adaptor 1300 may be manufactured from a material having a Q factor greater than 0.5. Illustratively, angled adaptor 1300 may be manufactured from a metal alloy in an annealed condition, e.g., angled adaptor 1300 may be manufactured from a titanium alloy in an annealed condition. In one or more embodiments, angled adaptor 1300 may be manufactured from Ti-6Al-4V extra-low interstitials in an annealed condition. Illustratively, flange 200, amplifier 100, inert ring 700, connector block 800, and angled adaptor 1300 may be manufactured from a same material. In one or more embodiments, flange 200, amplifier 100, inert ring 700, connector block 800, and angled adaptor 1300 may be manufactured from different materials, e.g., flange 200 may be manufactured from a first material, amplifier 100 may be manufactured from a second material, inert ring 700 may be manufactured from a third material, connector block 800 may be manufactured from a fourth material, and angled adaptor 1300 may be manufactured from a fifth material.

Figure 14B:
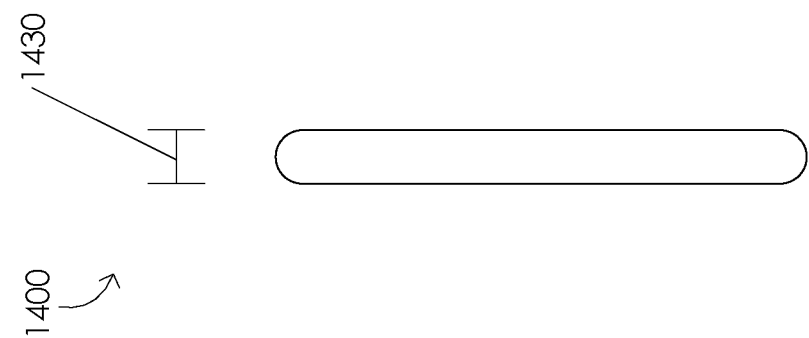
FIGS. 14A and 14B are schematic diagrams illustrating a first fluid seal.
Figure 14A:
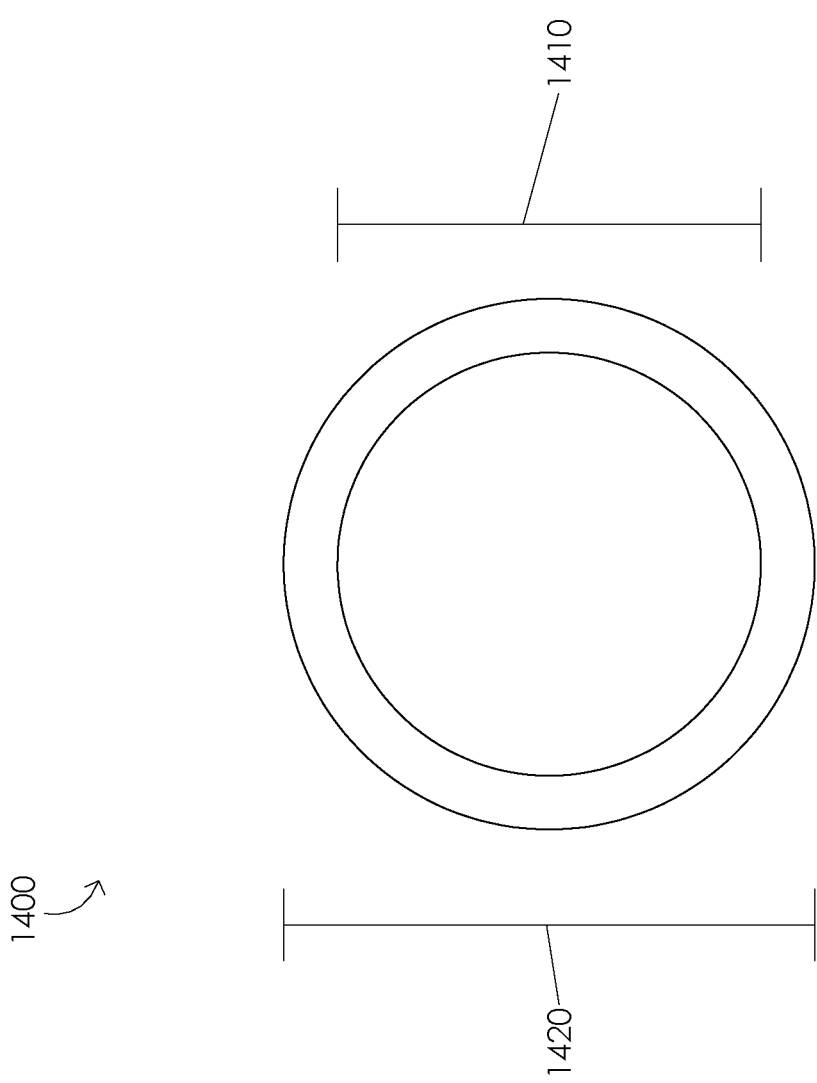

FIGS. 14A and 14B are schematic diagrams illustrating a first fluid seal 1400. FIG. 14A illustrates a top view of a first fluid seal 1400. FIG. 14B illustrates a side view of a first fluid seal 1400. In one or more embodiments, a first fluid seal 1400 may comprise a first fluid seal inner diameter 1410. Illustratively, first fluid seal 1400 may comprise a first fluid seal outer diameter 1420. In one or more embodiments, first fluid seal 1400 may comprise a first fluid seal thickness 1430. Illustratively, first fluid seal 1400 may be manufactured from any suitable material, e.g., polymers, metals, metal alloys, etc., or from any combination of suitable materials. In one or more embodiments, first fluid seal 1400 may be manufactured from a material having a Shore A hardness in a range of 5 to 80, e.g., first fluid seal 1400 may be manufactured from a material having a Shore A hardness of 70. Illustratively, first fluid seal 1400 may be manufactured from a material having a Shore A hardness of less than 5 or greater than 80. In one or more embodiments, first fluid seal 1400 may be manufactured from a silicone. Illustratively, first fluid seal 1400 may be manufactured from a silicone having a Shore A hardness in a range of 5 to 80, e.g., first fluid seal 1400 may be manufactured from a silicone having a Shore A hardness of 70. In one or more embodiments, first fluid seal 1400 may be manufactured from a silicone having a Shore A hardness of less than 5 or greater than 80. Illustratively, first fluid seal 1400 may be manufactured from a butyl, a chloroprene, an epichlorohydrin, an ethylene/acrylic, a fluorocarbon, a fluorosilicone, a nitrile, an ethylenepropylene, a natural rubber, a perfluoroelastomer, a styrene butadiene, a tetrafluoroethylene/propylene, a polyurethane, a polytetrafluoroethyne, a polysulfide, a polyacrylate, etc.

FIGS. 15A and 15B are schematic diagrams illustrating a second fluid seal 1500. FIG. 15A illustrates a top view of a second fluid seal 1500. FIG. 15B illustrates a side view of a second fluid seal 1500. In one or more embodiments, a second fluid seal 1500 may comprise a second fluid seal inner diameter 1510. Illustratively, second fluid seal 1500 may comprise a second fluid seal outer diameter 1520. In one or more embodiments, second fluid seal 1500 may comprise a second fluid seal thickness 1530. Illustratively, second fluid seal 1500 may be manufactured from any suitable material, e.g., polymers, metals, metal alloys, etc., or from any combination of suitable materials. In one or more embodiments, second fluid seal 1500 may be manufactured from a material having a Shore A hardness in a range of 5 to 80, e.g., second fluid seal 1500 may be manufactured from a material having a Shore A hardness of 70. Illustratively, second fluid seal 1500 may be manufactured from a material having a Shore A hardness of less than 5 or greater than 80. In one or more embodiments, second fluid seal 1500 may be manufactured from a silicone. Illustratively, second fluid seal 1500 may be manufactured from a silicone having a Shore A hardness in a range of 5 to 80, e.g., second fluid seal 1500 may be manufactured from a silicone having a Shore A hardness of 70. In one or more embodiments, second fluid seal 1500 may be manufactured from a silicone having a Shore A hardness of less than 5 or greater than 80. Illustratively, second fluid seal 1500 may be manufactured from a butyl, a chloroprene, an epichlorohydrin, an ethylene/acrylic, a fluorocarbon, a fluorosilicone, a nitrile, an ethylenepropylene, a natural rubber, a perfluoroelastomer, a styrene butadiene, a tetrafluoroethylene/propylene, a polyurethane, a polytetrafluoroethyne, a polysulfide, a polyacrylate, etc.

Figure 16A:
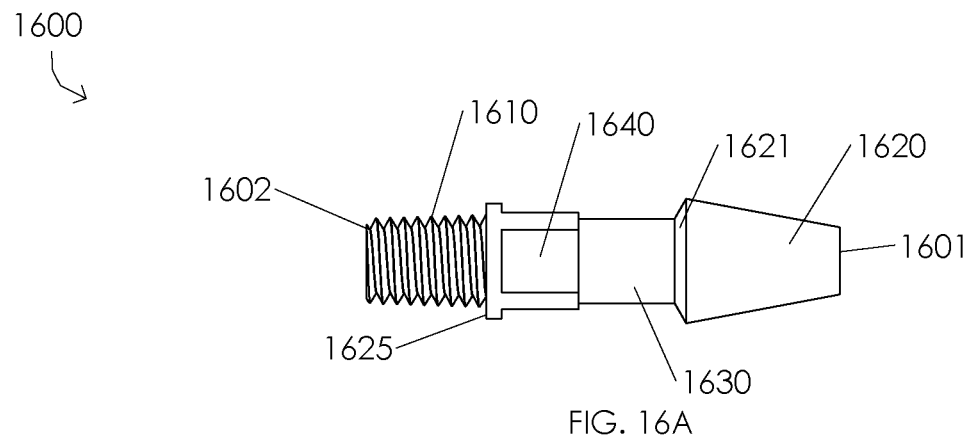
FIGS. 16A and 16B are schematic diagrams illustrating an irrigation barb.
Figure 16B:
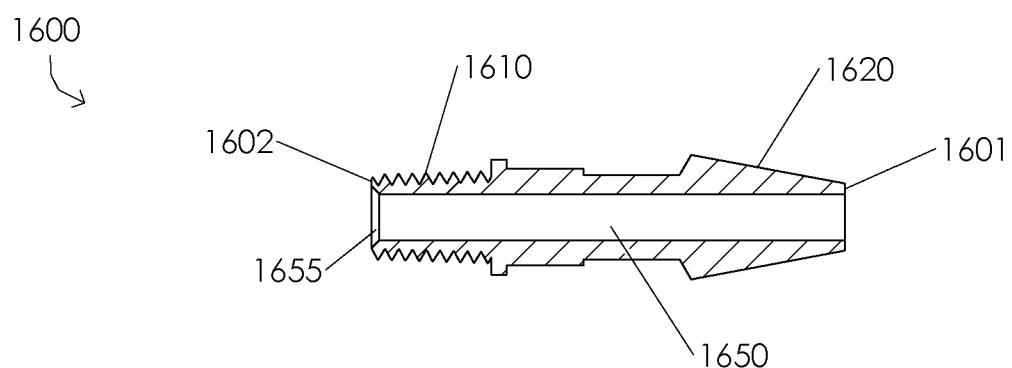

FIGS. 16A and 16B are schematic diagrams illustrating an irrigation barb 1600. FIG. 16A illustrates a top view of an irrigation barb 1600. FIG. 16B illustrates a crosssectional view in a transverse plane of an irrigation barb 1600. In one or more embodiments, an irrigation barb 1600 may comprise an irrigation barb distal end 1601 and an irrigation barb proximal end 1602. Illustratively, irrigation barb 1600 may comprise an irrigation barb thread 1610. In one or more embodiments, irrigation barb 1600 may comprise an irrigation barb head 1620. Illustratively, irrigation barb 1600 may comprise an irrigation barb chamfer 1621. In one or more embodiments, irrigation barb 1600 may comprise an irrigation barb stop 1625. Illustratively, irrigation barb 1600 may comprise an irrigation barb base 1630. In one or more embodiments, irrigation barb 1600 may comprise an irrigation barb tool interface 1640. Illustratively, irrigation barb 1600 may comprise an irrigation barb inner bore 1650. In one or more embodiments, irrigation barb 1600 may comprise an irrigation barb inner bore proximal bevel 1655.

In one or more embodiments, irrigation barb 1600 may be manufactured from any suitable material, e.g., polymers, metals, metal alloys, etc., or from any combination of suitable materials. Illustratively, irrigation barb 1600 may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, etc. For example, irrigation barb 1600 may be manufactured from a stainless steel, a brass, a bronze, a duralumin, a nitinol, etc. Illustratively, irrigation barb 1600 may be manufactured from an underdamped material. In one or more embodiments, irrigation barb 1600 may be manufactured from a material having a Q factor greater than 0.5. Illustratively, irrigation barb 1600 may be manufactured from a metal alloy in an annealed condition, e.g., irrigation barb 1600 may be manufactured from a titanium alloy in an annealed condition. In one or more embodiments, irrigation barb 1600 may be manufactured from Ti-6Al-4V extra-low interstitials in an annealed condition. Illustratively, flange 200, amplifier 100, inert ring 700, connector block 800, angled adaptor 1300, and irrigation barb 1600 may be manufactured from a same material. In one or more embodiments, flange 200, amplifier 100, inert ring 700, connector block 800, angled adaptor 1300, and irrigation barb 1600 may be manufactured from different materials, e.g., flange 200 may be manufactured from a first material, amplifier 100 may be manufactured from a second material, inert ring 700 may be manufactured from a third material, connector block 800 may be manufactured from a fourth material, angled adaptor 1300 may be manufactured from a fifth material, and irrigation barb 1600 may be manufactured from a sixth material.

Figure 17A:
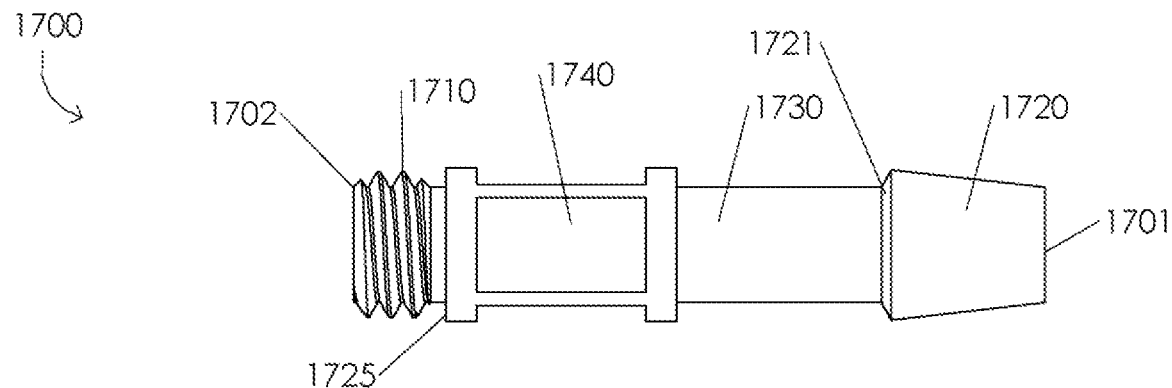
FIGS. 17A and 17B are schematic diagrams illustrating an aspiration barb.
Figure 17B:
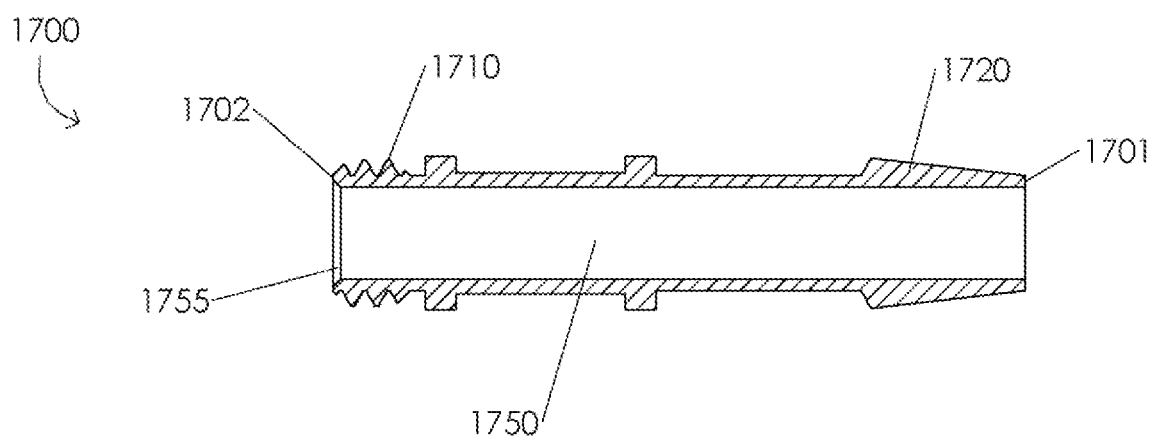

FIGS. 17A and 17B are schematic diagrams illustrating an aspiration barb 1700. FIG. 17A illustrates a side view of an aspiration barb 1700. FIG. 17B illustrates a crosssectional view in a sagittal plane of an aspiration barb 1700. In one or more embodiments, an aspiration barb 1700 may comprise an aspiration barb distal end 1701 and an aspiration barb proximal end 1702. Illustratively, aspiration barb 1700 may comprise an aspiration barb thread 1710. In one or more embodiments, aspiration barb 1700 may comprise an aspiration barb head 1720. Illustratively, aspiration barb 1700 may comprise an aspiration barb chamfer 1721. In one or more embodiments, aspiration barb 1700 may comprise a connector block proximal end interface 1725. Illustratively, aspiration barb 1700 may comprise an aspiration barb base 1730. In one or more embodiments, aspiration barb 1700 may comprise an aspiration barb tool interface 1740. Illustratively, aspiration barb 1700 may comprise an aspiration barb inner bore 1750. In one or more embodiments, aspiration barb 1700 may comprise an aspiration barb inner bore proximal bevel 1755.

In one or more embodiments, aspiration barb 1700 may be manufactured from any suitable material, e.g., polymers, metals, metal alloys, etc., or from any combination of suitable materials. Illustratively, aspiration barb 1700 may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, etc. For example, aspiration barb 1700 may be manufactured from a stainless steel, a brass, a bronze, a duralumin, a nitinol, etc. Illustratively, aspiration barb 1700 may be manufactured from an underdamped material. In one or more embodiments, aspiration barb 1700 may be manufactured from a material having a Q factor greater than 0.5. Illustratively, aspiration barb 1700 may be manufactured from a metal alloy in an annealed condition, e.g., aspiration barb 1700 may be manufactured from a titanium alloy in an annealed condition. In one or more embodiments, aspiration barb 1700 may be manufactured from Ti-6Al-4V extra-low interstitials in an annealed condition. Illustratively, flange 200, amplifier 100, inert ring 700, connector block 800, angled adaptor 1300, irrigation barb 1600, and aspiration barb 1700 may be manufactured from a same material. In one or more embodiments, flange 200, amplifier 100, inert ring 700, connector block 800, angled adaptor 1300, irrigation barb 1600, and aspiration barb 1700 may be manufactured from different materials, e.g., flange 200 may be manufactured from a first material, amplifier 100 may be manufactured from a second material, inert ring 700 may be manufactured from a third material, connector block 800 may be manufactured from a fourth material, angled adaptor 1300 may be manufactured from a fifth material, irrigation barb 1600 may be manufactured from a sixth material, and aspiration barb 1700 may be manufactured from a seventh material.

Figure 18C:
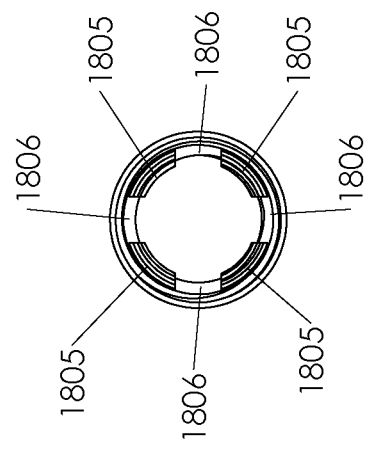
FIGS. 18A, 18B, and 18C are schematic diagrams illustrating a cable retention mechanism.
Figure 18A:
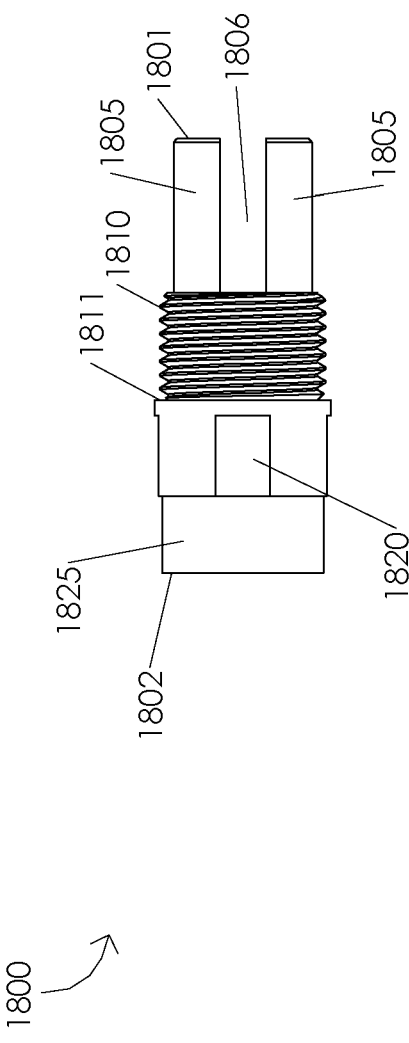
Figure 18B:
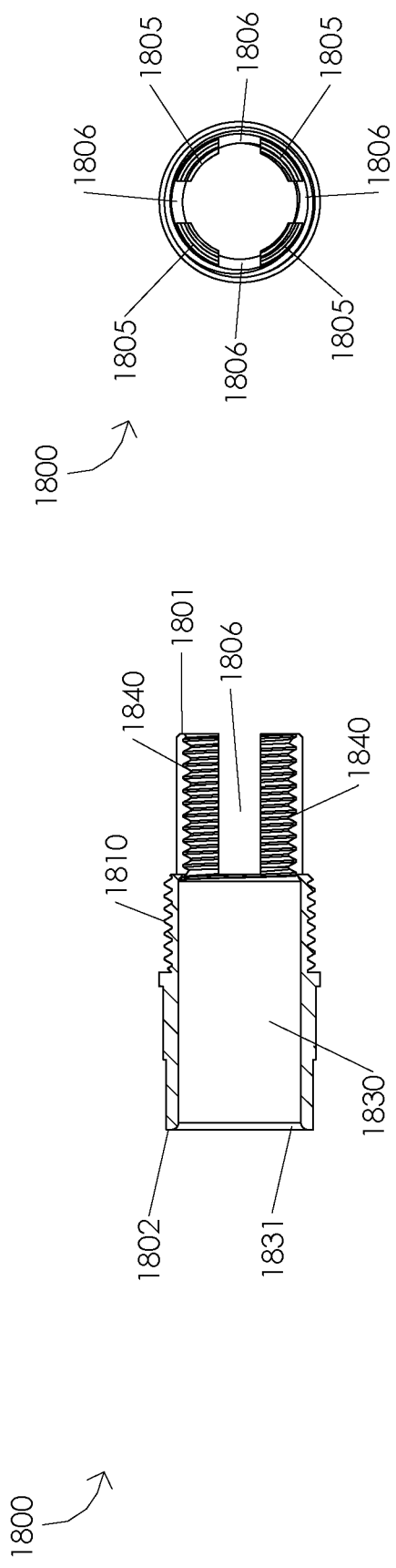

FIGS. 18A, 18B, and 18C are schematic diagrams illustrating a cable retention mechanism 1800. FIG. 18A illustrates a side view of a cable retention mechanism 1800. FIG. 18B illustrates a crosssectional view in a sagittal plane of a cable retention mechanism 1800. FIG. 18C illustrates a front view of a cable retention mechanism 1800. In one or more embodiments, a cable retention mechanism 1800 may comprise a cable retention mechanism distal end 1801 and a cable retention mechanism proximal end 1802. Illustratively, cable retention mechanism 1800 may comprise a retention lever 1805, e.g., cable retention mechanism 1800 may comprise a plurality of retention levers 1805. In one or more embodiments, cable retention mechanism 1800 may comprise a retention channel 1806, e.g., cable retention mechanism 1800 may comprise a plurality of retention channels 1806. Illustratively, cable retention mechanism 1800 may comprise a cable retention mechanism thread 1810. In one or more embodiments, cable retention mechanism 1800 may comprise a connector block offset face interface 1811. Illustratively, cable retention mechanism 1800 may comprise a cable retention mechanism tool interface 1820. In one or more embodiments, cable retention mechanism 1800 may comprise a first cable strain relief 1825. Illustratively, cable retention mechanism 1800 may comprise a cable housing 1830. In one or more embodiments, cable retention mechanism 1800 may comprise a cable housing proximal bevel 1831. Illustratively, cable retention mechanism 1800 may comprise a retention surface 1840.

In one or more embodiments, cable retention mechanism 1800 may be manufactured from an electrically conductive material, e.g., cable retention mechanism 1800 may be manufactured from aluminum, an aluminum alloy, silver, a silver alloy, copper, a copper alloy, gold, a gold alloy, platinum, a platinum alloy, tin, a tin alloy, palladium, a palladium alloy, nickel, a nickel alloy, beryllium, a beryllium alloy, tungsten, a tungsten alloy, a steel, chromium, a chromium alloy, titanium, a titanium alloy, etc. Illustratively, cable retention mechanism 1800 may be manufactured from a beryllium copper. In one or more embodiments, cable retention mechanism 1800 may be manufactured from a stainless steel, e.g., cable retention mechanism 1800 may be manufactured from a spring steel.

FIG. 19 is a schematic diagram illustrating a cable 1900. In one or more embodiments, a cable 1900 may comprise a cable jacket 1910. Illustratively, cable 1900 may comprise a first electrical conductor 1920, e.g., cable 1900 may comprise a first electrical conductor 1920 disposed in cable jacket 1910. In one or more embodiments, cable 1900 may comprise a second electrical conductor 1930, e.g., cable 1900 may comprise a second electrical conductor 1930 disposed in cable jacket 1910.

Figure 20B:
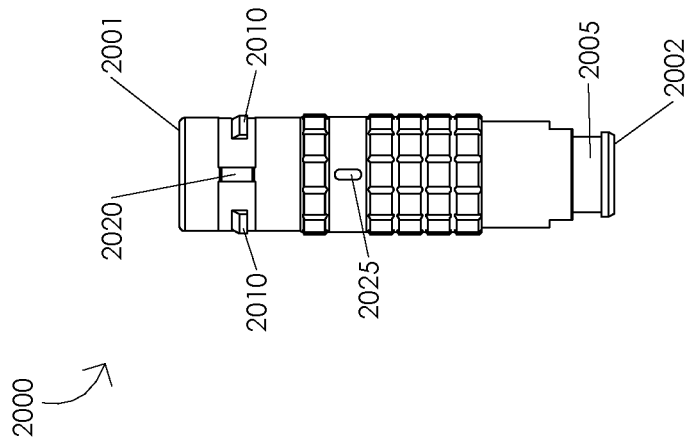
FIGS. 20A and 20B are schematic diagrams illustrating a connector.
Figure 20A:
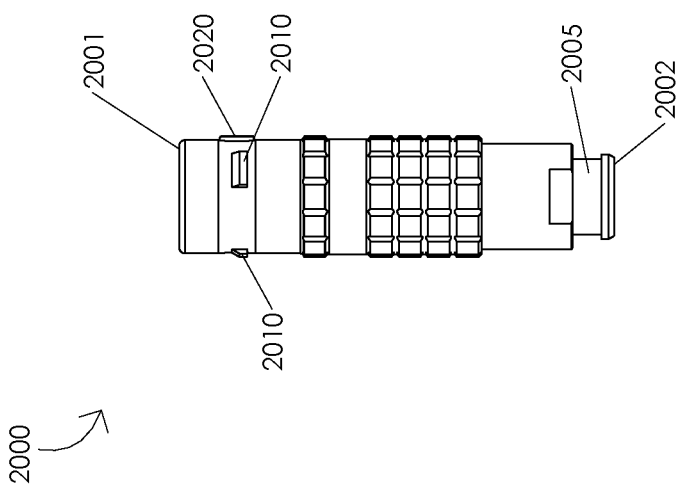

FIGS. 20A and 20B are schematic diagrams illustrating a connector 2000. FIG. 20A illustrates a side view of a connector 2000. FIG. 20B illustrates a top view of a connector 2000. In one or more embodiments, a connector 2000 may comprise a connector distal end 2001 and a connector proximal end 2002. Illustratively, connector 2000 may comprise a second cable strain relief mount 2005. In one or more embodiments, connector 2000 may comprise a connection guide mechanism 2010, e.g., connector 2000 may comprise a plurality of connection guide mechanisms 2010. Illustratively, connector 2000 may comprise a connection lock mechanism 2020, e.g., connector 2000 may comprise a plurality of connection lock mechanism 2020. In one or more embodiments, connector 2000 may comprise an alignment indicator 2025.

Figure 21A:
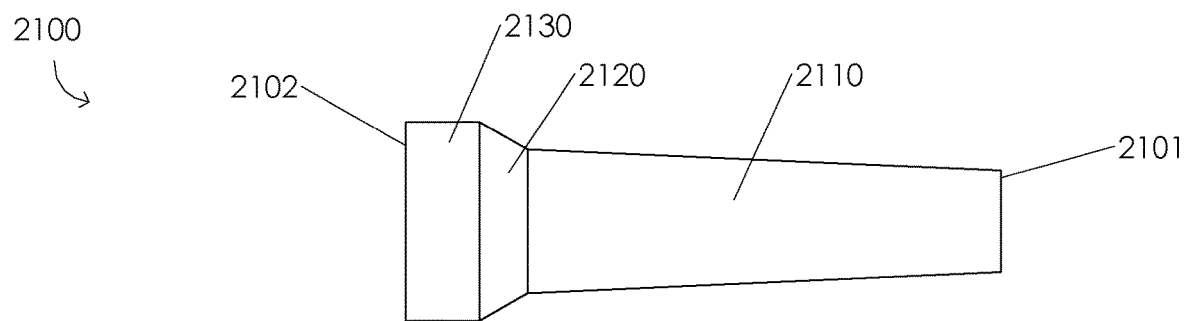
FIGS. 21A and 21B are schematic diagrams illustrating a second cable strain relief.
Figure 21B:
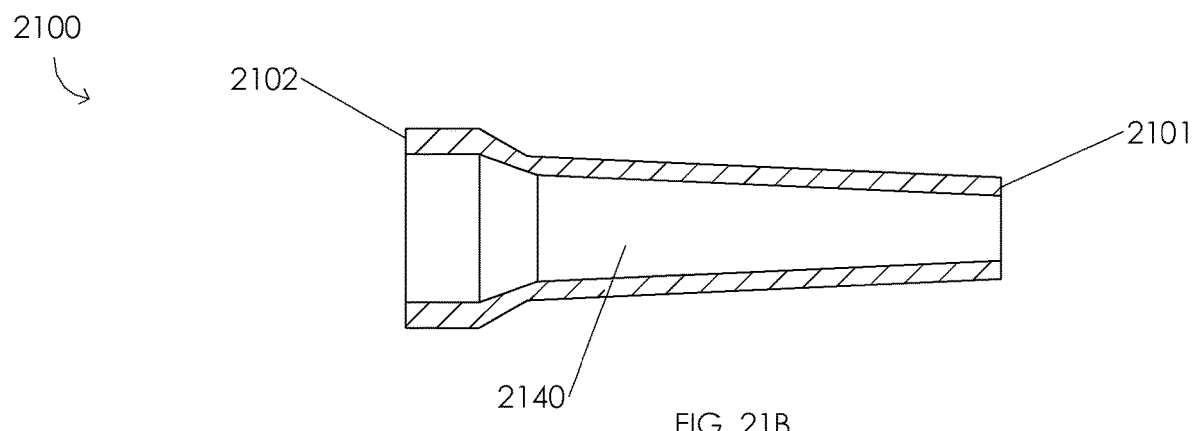

FIGS. 21A and 21B are schematic diagrams illustrating a second cable strain relief 2100. FIG. 21A illustrates a side view of a second cable strain relief 2100. FIG. 21B illustrates a crosssectional view in a sagittal plane of a second cable strain relief 2100. In one or more embodiments, a second cable strain relief 2100 may comprise a second cable strain relief distal end 2101 and a second cable strain relief proximal end 2102. Illustratively, second cable strain relief 2100 may comprise a connector sleeve 2110. In one or more embodiments, second cable strain relief 2100 may comprise a spring 2120. Illustratively, second cable strain relief 2100 may comprise a tapered cable sleeve 2130. In one or more embodiments, second cable strain relief 2100 may comprise a second cable strain relief inner bore 2140.

Figure 22:
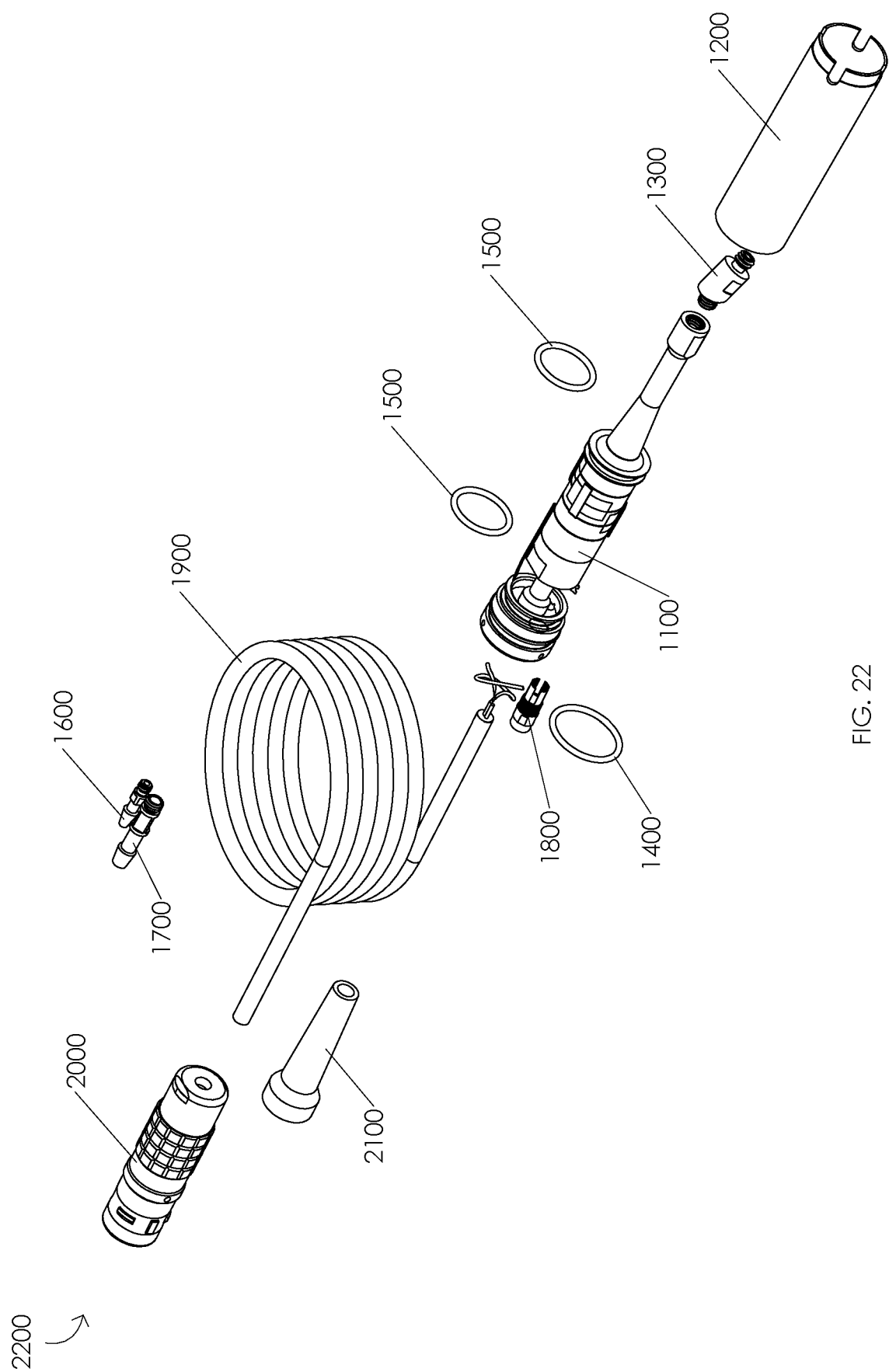
FIG. 22 is a schematic diagram illustrating an exploded view of a motor assembly.

FIG. 22 is a schematic diagram illustrating an exploded view of a motor assembly 2200. In one or more embodiments, a motor assembly 2200 may comprise an assembled transducer 1100, a transducer sleeve 1200, an angled adaptor, a first fluid seal 1400, a distal second fluid seal 1500, a proximal second fluid seal 1500, an irrigation barb 1600, an aspiration barb 1700, a cable retention mechanism 1800, a cable 1900, a connector 2000, and a second cable strain relief 2100.

FIGS. 23A and 23B are schematic diagrams illustrating an assembled motor 2300. FIG. 23A illustrates a side view of an assembled motor 2300. FIG. 23B illustrates a top view of an assembled motor 2300. In one or more embodiments, a portion of angled adaptor 1300 may be disposed in a portion of amplifier 100, e.g., angled adaptor proximal end 1302 may be disposed in amplifier interface 125. Illustratively, a portion of angled adaptor 1300 may be disposed in a portion of amplifier 100 wherein medial inner bore proximal bevel 1355 is disposed in amplifier distal undercut 135, e.g., a portion of angled adaptor 1300 may be disposed in a portion of amplifier 100 wherein medial inner bore proximal bevel 1355 is disposed in amplifier inner bore 130. In one or more embodiments, a portion of angled adaptor 1300 may be disposed in a portion of amplifier 100 wherein a portion of medial inner bore 1350 is disposed in amplifier distal undercut 135, e.g., a portion of angled adaptor 1300 may be disposed in a portion of amplifier 100 wherein angled adaptor proximal end 1302 is disposed in amplifier distal undercut 135. Illustratively, a portion of angled adaptor 1300 may be disposed in a portion of amplifier 100 wherein angled adaptor proximal end 1302 is adjacent to amplifier inner bore 130, e.g., a portion of angled adaptor 1300 may be disposed in a portion of amplifier 100 wherein angled adaptor proximal end 1302 abuts amplifier inner bore 130. In one or more embodiments, a portion of angled adaptor 1300 may be disposed in a portion of amplifier 100 wherein amplifier inner bore 130 is aligned with medial inner bore 1350, e.g., a portion of angled adaptor 1300 may be disposed in a portion of amplifier 100 wherein amplifier inner bore 130 is colinear with medial inner bore 1350. Illustratively, a portion of angled adaptor 1300 may be disposed in a portion of amplifier 100 wherein amplifier distal end 101 is adjacent to amplifier interface 1325, e.g., a portion of angled adaptor 1300 may be disposed in a portion of amplifier 100 wherein amplifier distal end 101 abuts amplifier interface 1325.

In one or more embodiments, a portion of angled adaptor 1300 may be disposed in amplifier distal thread 133, e.g., angled adaptor proximal thread 1310 may be disposed in amplifier distal thread 133. Illustratively, angled adaptor proximal thread 1310 may comprise an external thread and amplifier distal thread 133 may comprise an internal thread, e.g., angled adaptor proximal thread 1310 and amplifier distal thread 133 may be configured to convert a torque into a linear force. In one or more embodiments, amplifier distal thread 133 may comprise an external thread and angled adaptor proximal thread 1310 may comprise an internal thread, e.g., amplifier distal thread 133 and angled adaptor proximal thread 1310 may be configured to convert a torque into a linear force. Illustratively, a portion of angled adaptor 1300 may be disposed in a portion of amplifier 100 wherein the portion of angled adaptor 1300 is fixed in the portion of amplifier 100, e.g., the portion of angled adaptor 1300 may be fixed in the portion of amplifier 100 by a force of friction. In one or more embodiments, a portion of angled adaptor proximal thread 1310 may be disposed in a portion of amplifier distal thread 133 wherein the portion of angled adaptor proximal thread 1310 is fixed in the portion of amplifier distal thread 133, e.g., the portion of angled adaptor proximal thread 1310 may be fixed in the portion of amplifier distal thread 133 by a force of friction. Illustratively, a portion of angled adaptor 1300 may be fixed in a portion of amplifier 100 by any suitable fixation means, e.g., a portion of angled adaptor 1300 may be fixed in a portion of amplifier 100 by an interference fit, a weld, an adhesive, and epoxy, a crimp, a tie, a pin, etc. In one or more embodiments, angled adaptor proximal thread 1310 and amplifier distal thread 133 may be configured to align angled adaptor distal thread 1320 wherein a first portion of angled adaptor distal thread 1320 is disposed below a transverse plane of angled adaptor 1300 and a second portion of angled adaptor distal thread 1320 is disposed above the transverse plane of angled adaptor 1300 when angled adaptor proximal thread 1310 is fully disposed in amplifier distal thread 133. Illustratively, the first portion of angled adaptor distal thread 1320 may be greater than the second portion of angled adaptor distal thread 1320. In one or more embodiments, angled adaptor proximal thread 1310 and amplifier distal thread 133 may be configured to align angled adaptor distal thread 1320 wherein a first portion of angled adaptor distal thread 1320 is disposed below a transverse plane of angled adaptor 1300 and a second portion of angled adaptor distal thread 1320 is disposed above the transverse plane of angled adaptor 1300 when amplifier interface 1325 abuts amplifier distal end 101. Illustratively, the first portion of angled adaptor distal thread 1320 may be greater than the second portion of angled adaptor distal thread 1320.

In one or more embodiments, a portion of irrigation barb 1600 may be disposed in a portion of connector block 800, e.g., irrigation barb proximal end 1602 may be disposed in a portion of connector block 800. Illustratively, a portion of irrigation barb 1600 may be disposed in irrigation barb housing 851, e.g., irrigation barb proximal end 1602 may be disposed in irrigation barb housing 851. In one or more embodiments, irrigation barb 1600 may be disposed in connector block 800 wherein a portion of irrigation barb 1600 extends out from a portion of connector block 800, e.g., irrigation barb 1600 may be disposed in connector block 800 wherein irrigation barb distal end 1601 extends out from connector block proximal end 802. Illustratively, irrigation barb 1600 may be disposed in connector block 800 wherein irrigation barb stop 1625 is adjacent to connector block proximal end 802, e.g., irrigation barb 1600 may be disposed in connector block 800 wherein irrigation barb stop 1625 abuts connector block proximal end 802.

In one or more embodiments, a portion of irrigation barb 1600 may be disposed in a portion of third connector block proximal thread 850, e.g., a portion of irrigation barb thread 1610 may be disposed in a portion of third connector block proximal thread 850. Illustratively, irrigation barb thread 1610 may comprise an external thread and third connector block proximal thread 850 may comprise an internal thread, e.g., irrigation barb thread 1610 and third connector block proximal thread 850 may be configured to convert a torque into a linear force. In one or more embodiments, third connector block proximal thread 850 may comprise an external thread and irrigation barb thread 1610 may comprise an internal thread, e.g., third connector block proximal thread 850 and irrigation barb thread 1610 may be configured to convert a torque into a linear force. Illustratively, irrigation barb thread 1610 may comprise a tapered external thread and third connector block proximal thread 850 may comprise a tapered internal thread, e.g., irrigation barb thread 1610 and third connector block proximal thread 850 may be configured to form a hermetic seal. For example, irrigation barb thread 1610 and third connector block proximal thread 850 may be configured to form a watertight seal. In one or more embodiments, third connector block proximal thread 850 may comprise a tapered external thread and irrigation barb thread 1610 may comprise a tapered internal thread, e.g., third connector block proximal thread 850 and irrigation barb thread 1610 may be configured to form a hermetic seal. For example, irrigation barb thread 1610 and third connector block proximal thread 850 may be configured to form a watertight seal. Illustratively, a portion of irrigation barb 1600 may be disposed in a portion of connector block 800 wherein the portion of irrigation barb 1600 is fixed in the portion of connector block 800, e.g., the portion of irrigation barb 1600 may be fixed in the portion of connector block 800 by a force of friction. In one or more embodiments, a portion of irrigation barb thread 1610 may be disposed in a portion of third connector block proximal thread 850 wherein the portion of irrigation barb thread 1610 is fixed in the portion of third connector block proximal thread 850, e.g., the portion of irrigation barb thread 1610 may be fixed in the portion of third connector block proximal thread 850 by a force of friction. Illustratively, a portion of irrigation barb 1600 may be fixed in a portion of connector block 800 by any suitable fixation means, e.g., a portion of irrigation barb 1600 may be fixed in a portion of connector block 800 by an interference fit, a weld, an adhesive, and epoxy, a crimp, a tie, a pin, etc.

In one or more embodiments, a portion of aspiration barb 1700 may be disposed in a portion of connector block 800, e.g., aspiration barb proximal end 1702 may be disposed in a portion of connector block 800. Illustratively, a portion of aspiration barb 1700 may be disposed in aspiration barb housing taper 838, e.g., aspiration barb proximal end 1702 may be disposed in aspiration barb housing taper 830. In one or more embodiments, a portion of aspiration barb 1700 may be disposed in aspiration barb housing 837, e.g., aspiration barb proximal end 1702 may be disposed in aspiration barb housing 837. Illustratively, a portion of aspiration barb inner bore 1750 may be disposed in aspiration barb housing taper 838, e.g., aspiration barb inner bore proximal bevel 1755 may be disposed in aspiration barb housing taper 838. In one or more embodiments, a portion of aspiration barb inner bore 1750 may be disposed in aspiration barb housing 837, e.g., aspiration barb inner bore proximal bevel 1755 may be disposed in aspiration barb housing 837. Illustratively, a portion of aspiration barb inner bore 1750 may be disposed in connector block inner bore 830, e.g., aspiration barb inner bore proximal bevel 1755 may be disposed in connector block inner bore 830. In one or more embodiments, aspiration barb 1700 may be disposed in connector block 800 wherein aspiration barb inner bore 1750 is aligned with connector block inner bore 830, e.g., aspiration barb 1700 may be disposed in connector block 800 wherein aspiration barb inner bore 1750 is colinear with connector block inner bore 830. Illustratively, aspiration barb 1700 may be disposed in connector block 800 wherein a portion of aspiration barb 1700 extends out from connector block 800, e.g., aspiration barb 1700 may be disposed in connector block 800 wherein aspiration barb distal end 1701 extends out from connector block proximal end 802. In one or more embodiments, a portion of aspiration barb 1700 may be disposed in a portion of connector block 800 wherein connector block proximal end interface 1725 is adjacent to connector block proximal end 802, e.g., a portion of aspiration barb 1700 may be disposed in a portion of connector block 800 wherein connector block proximal end interface 1725 abuts connector block proximal end 802.

Illustratively, a portion of aspiration barb 1700 may be disposed in a portion of first connector block proximal thread 835, e.g., a portion of aspiration barb thread 1710 may be disposed in a portion of first connector block proximal thread 835. In one or more embodiments, aspiration barb thread 1710 may comprise an external thread and first connector block proximal thread 835 may comprise an internal thread, e.g., aspiration barb thread 1710 and first connector block proximal thread 835 may be configured to convert a torque into a linear force. Illustratively, first connector block proximal thread 835 may comprise an external thread and aspiration barb thread 1710 may comprise an internal thread, e.g., first connector block proximal thread 835 and aspiration barb thread 1710 may be configured to convert a torque into a linear force. In one or more embodiments, aspiration barb thread 1710 may comprise a tapered external thread and first connector block proximal thread 835 may comprise a tapered internal thread, e.g., aspiration barb thread 1710 and first connector block proximal thread 835 may be configured to form a hermetic seal. For example, aspiration barb thread 1710 and first connector block proximal thread 835 may be configured to form a watertight seal. Illustratively, first connector block proximal thread 835 may comprise a tapered external thread and aspiration barb thread 1710 may comprise a tapered internal thread, e.g., first connector block proximal thread 835 and aspiration barb thread 1710 may be configured to form a hermetic seal. For example, first connector block proximal thread 835 and aspiration barb thread 1710 may be configured to form a watertight seal. In one or more embodiments, a portion of aspiration barb 1700 may be disposed in a portion of connector block 800 wherein the portion of aspiration barb 1700 is fixed in the portion of connector block 800, e.g., the portion of aspiration barb 1700 may be fixed in the portion of connector block 800 by a force of friction. Illustratively, a portion of aspiration barb thread 1710 may be disposed in a portion of first connector block proximal thread 835 wherein the portion of aspiration barb thread 1710 is fixed in the portion of first connector block proximal thread 835, e.g., the portion of aspiration barb thread 1710 may be fixed in the portion of first connector block proximal thread 835 by a force of friction. In one or more embodiments, a portion of aspiration barb 1700 may be fixed in a portion of connector block 800 by any suitable fixation means, e.g., a portion of aspiration barb 1700 may be fixed in a portion of connector block 800 by an interference fit, a weld, an adhesive, and epoxy, a crimp, a tie, a pin, etc.

Illustratively, a portion of cable 1900 may be disposed in a portion of second cable strain relief 2100, e.g., cable jacket 1910 may be disposed in second cable strain relief inner bore 2140. In one or more embodiments, a portion of cable 1900 may be disposed in connector sleeve 2130, spring 2120, and tapered cable sleeve 2110. Illustratively, a first portion of cable 1900 may be disposed in second cable strain relief 2100 wherein a second portion of cable 1900 extends out from second cable strain relief distal end 2101. In one or more embodiments, a portion of first electrical connector 1920 may be disposed in second cable strain relief inner bore 2140, e.g., the portion of first electrical conductor 1920 may be disposed in cable jacket 1910. Illustratively, a portion of second electrical connector 1930 may be disposed in second cable strain relief inner bore 2140, e.g., the portion of second electrical conductor 1930 may be disposed in cable jacket 1910. In one or more embodiments, a portion of first electrical conductor 1920 may be disposed in a portion of connector 2000, e.g., the portion of first electrical conductor 1920 may be disposed in connector proximal end 2002. Illustratively, a portion of first electrical conductor 1920 may be disposed in connector 2000 wherein the portion of first electrical conductor 1920 is electrically connected to a portion of connector 2000, e.g., a portion of first electrical conductor 1920 may be disposed in connector 2000 wherein the portion of first electrical conductor 1920 is electrically connected to a first inner portion of connector 2000. In one or more embodiments, a portion of first electrical conductor 1920 may be disposed in a portion of connector 2000 wherein the portion of first electrical conductor 1920 is fixed in the portion of connector 2000, e.g., the portion of first electrical conductor 1920 may be fixed in the portion of connector 2000 by a solder joint, an interference fit, a weld, an adhesive, and epoxy, a crimp, a tie, a pin, etc. Illustratively, a portion of second electrical conductor 1930 may be disposed in a portion of connector 2000, e.g., the portion of second electrical conductor 1930 may be disposed in connector proximal end 2002. In one or more embodiments, a portion of second electrical conductor 1930 may be disposed in connector 2000 wherein the portion of second electrical conductor 1930 is electrically connected to a portion of connector 2000, e.g., a portion of second electrical conductor 1930 may be disposed in connector 2000 wherein the portion of second electrical conductor 1930 is electrically connected to a second inner portion of connector 2000. Illustratively, a portion of second electrical conductor 1930 may be disposed in a portion of connector 2000 wherein the portion of second electrical conductor 1930 is fixed in the portion of connector 2000, e.g., the portion of second electrical conductor 1930 may be fixed in the portion of connector 2000 by a solder joint, an interference fit, a weld, an adhesive, and epoxy, a crimp, a tie, a pin, etc. In one or more embodiments, a portion of connector 2000 may be disposed in a portion of second cable strain relief 2100, e.g., connector proximal end 2002 may be disposed in a portion of second cable strain relief 2100. Illustratively, second cable strain relief mount 2005 may be disposed in a portion of second cable strain relief inner bore 2140, e.g., second cable strain relief mount 2005 may be disposed in connector sleeve 2130. In one or more embodiments, a portion of connector 2000 may be fixed in a portion of second cable strain relief 2100, e.g., a portion of connector 2000 may be fixed in a portion of second cable strain relief 2100 by an interference fit, a weld, an adhesive, and epoxy, a crimp, a tie, a pin, etc.

In one or more embodiments, a portion of cable 1900 may be disposed in cable retention mechanism 1800, e.g., a portion of cable 1900 may be disposed in cable housing 1830. Illustratively, cable jacket 1910 may be disposed in cable housing 1830 wherein a portion of cable jacket 1910 extends out from cable retention mechanism proximal end 1802. In one or more embodiments, a portion of cable 1900 may be disposed in a portion of connector block 800, e.g., cable jacket 1910 may be disposed in a portion of connector block 800. Illustratively, a portion of first electrical conductor 1920 may be disposed in a portion of connector block 800, e.g., a portion of first electrical conductor 1920 may be disposed in second connector block proximal thread 845. In one or more embodiments, a portion of first electrical conductor 1920 may be disposed in retention mechanism housing 846, e.g., a portion of first electrical conductor 1920 may be disposed in retention mechanism housing taper 847. Illustratively, a portion of first electrical conductor 1920 may be disposed in recess 840, e.g., a portion of first electrical conductor 1920 may be disposed over recess lateral fillet 841. In one or more embodiments, first electrical conductor 1920 may be disposed in connector block 800 wherein a portion of first electrical conductor 1920 extends out from recess 840, e.g., first electrical conductor 1920 may be disposed in connector block 800 wherein a portion of first electrical conductor 1920 extends out from recess 840 and wherein the portion of first electrical conductor 1920 contacts a portion of outer electrode stack 500. Illustratively, first electrical conductor 1920 may be disposed in a connector block 800 wherein a portion of first electrical conductor 1920 is electrically connected to a portion of outer electrode stack 500, e.g., first electrical conductor 1920 may be disposed in a connector block 800 wherein a portion of first electrical conductor 1920 is electrically connected to first lead 530. In one or more embodiments, first electrical conductor 1920 may be disposed in connector block 800 wherein a portion of first electrical conductor 1920 is electrically connected to first lead projection 545, e.g., first electrical conductor 1920 may be disposed in connector block 800 wherein a portion of first electrical conductor 1920 is disposed in first lead guide 546. Illustratively, first electrical conductor 1920 may be disposed in connector block 800 wherein a portion of first electrical conductor 1920 is fixed to a portion of outer electrode stack 500, e.g., first electrical conductor 1920 may be disposed in connector block 800 wherein a portion of first electrical conductor 1920 is fixed to a portion of outer electrode stack 500 by a solder joint, an interference fit, a weld, an adhesive, and epoxy, a crimp, a tie, a pin, etc. In one or more embodiments, first electrical conductor 1920 may be configured to electrically connect outer electrode stack 500 and a portion of connector 2000, e.g., first electrical conductor 1920 may be configured to electrically connect outer electrode stack 500 and a first inner portion of connector 2000.

Illustratively, a portion of second electrical conductor 1930 may be disposed in a portion of connector block 800, e.g., a portion of second electrical conductor 1930 may be disposed in second connector block proximal thread 845. In one or more embodiments, a portion of second electrical conductor 1930 may be disposed in retention mechanism housing 846, e.g., a portion of second electrical conductor 1930 may be disposed in retention mechanism housing taper 847. Illustratively, a portion of second electrical conductor 1930 may be disposed in recess 840, e.g., a portion of second electrical conductor 1930 may be disposed over recess lateral fillet 841. In one or more embodiments, second electrical conductor 1930 may be disposed in connector block 800 wherein a portion of second electrical conductor 1930 extends out from recess 840, e.g., second electrical conductor 1930 may be disposed in connector block 800 wherein a portion of second electrical conductor 1930 extends out from recess 840 and wherein the portion of second electrical conductor 1930 contacts a portion of inner electrode stack 600. Illustratively, second electrical conductor 1930 may be disposed in a connector block 800 wherein a portion of second electrical conductor 1930 is electrically connected to a portion of inner electrode stack 600, e.g., second electrical conductor 1930 may be disposed in a connector block 800 wherein a portion of second electrical conductor 1930 is electrically connected to second lead 620. In one or more embodiments, second electrical conductor 1930 may be disposed in connector block 800 wherein a portion of second electrical conductor 1930 is electrically connected to second lead projection 645, e.g., second electrical conductor 1930 may be disposed in connector block 800 wherein a portion of second electrical conductor 1930 is disposed in second lead guide 646. Illustratively, second electrical conductor 1930 may be disposed in connector block 800 wherein a portion of second electrical conductor 1930 is fixed to a portion of inner electrode stack 600, e.g., second electrical conductor 1930 may be disposed in connector block 800 wherein a portion of second electrical conductor 1930 is fixed to a portion of inner electrode stack 600 by a solder joint, an interference fit, a weld, an adhesive, and epoxy, a crimp, a tie, a pin, etc. In one or more embodiments, second electrical conductor 1930 may be configured to electrically connect inner electrode stack 600 and a portion of connector 2000, e.g., second electrical conductor 1930 may be configured to electrically connect inner electrode stack 600 and a second inner portion of connector 2000.

In one or more embodiments, a portion of cable retention mechanism 1800 may be disposed in a portion of connector block 800, e.g., cable retention mechanism distal end 1801 may be disposed in a portion of connector block 800. Illustratively, cable retention mechanism 1800 may be configured to prevent a portion of cable 1900 from being unintentionally removed from connector block 800, e.g., cable retention mechanism 1800 may be configured to prevent an unintentional electrical disconnection of first electrical conductor 1920 from outer electrode stack 500. In one or more embodiments, cable retention mechanism 1800 may be configured to prevent an unintentional electrical disconnection of second electrical conductor 1930 from inner electrode stack 600. Illustratively, cable retention mechanism 1800 may be disposed in connector block 800 wherein a portion of cable retention mechanism 1800 extends out from connector block 800, e.g., cable retention mechanism 1800 may be disposed in connector block 800 wherein cable retention proximal end 1802 extends out from connector block proximal end 802. In one or more embodiments, cable retention mechanism 1800 may be disposed in connector block 800 wherein a portion of cable retention mechanism 1800 extends out from offset face 804, e.g., cable retention mechanism 1800 may be disposed in connector block 800 wherein cable retention mechanism proximal end 1802 extends out from offset face 804. Illustratively, cable retention mechanism 1800 may be disposed in connector block 800 wherein first cable strain relief 1825 extends out from connector block proximal end 802, e.g., cable retention mechanism 1800 may be disposed in connector block 800 wherein first cable strain relief 1825 extends out from offset face 804. In one or more embodiments, cable retention mechanism 1800 may be disposed in connector block 800 wherein a portion of cable housing 1830 extends out from connector block proximal end 802, e.g., cable retention mechanism 1800 may be disposed in connector block 800 wherein a portion of cable housing 1830 extends out from offset face 804. Illustratively, cable retention mechanism 1800 may be disposed in connector block 800 wherein cable housing proximal bevel 1831 extends out from connector block proximal end 802, e.g., cable retention mechanism 1800 may be disposed in connector block 800 wherein cable housing proximal bevel 1831 extends out from offset face 804. In one or more embodiments, a retention lever 1805 may be disposed in a portion of connector block 800, e.g., a plurality of retention levers 1805 may be disposed in a portion of connector block 800. Illustratively, a retention channel 1806 may be disposed in a portion of connector block 800, e.g., a plurality of retention channels 1806 may be disposed in a portion of connector block 800. In one or more embodiments, a portion of cable retention mechanism 1800 may be disposed in retention mechanism housing taper 847, e.g., cable retention mechanism distal end 1801 may be disposed in retention mechanism housing taper 847. Illustratively, a portion of cable retention mechanism 1800 may be disposed in connector block 800 wherein connector block offset face interface 1811 is adjacent to offset face 804, e.g., a portion of cable retention mechanism 1800 may be disposed in connector block 800 wherein connector block offset face interface 1811 abuts offset face 804.

In one or more embodiments, a portion of cable retention mechanism 1800 may be disposed in a portion of second connector block proximal thread 845, e.g., a portion of cable retention mechanism thread 1810 may be disposed in a portion of second connector block proximal thread 845. Illustratively, cable retention mechanism thread 1810 may comprise an external thread and second connector block proximal thread 845 may comprise an internal thread, e.g., cable retention mechanism thread 1810 and second connector block proximal thread 845 may be configured to convert a torque into a linear force. In one or more embodiments, second connector block proximal thread 845 may comprise an external thread and cable retention mechanism thread 1810 may comprise an internal thread, e.g., second connector block proximal thread 845 and cable retention mechanism thread 1810 may be configured to convert a torque into a linear force. Illustratively, cable retention mechanism thread 1810 may comprise a tapered external thread and second connector block proximal thread 845 may comprise a tapered internal thread, e.g., cable retention mechanism thread 1810 and second connector block proximal thread 845 may be configured to form a hermetic seal. For example, cable retention mechanism thread 1810 and second connector block proximal thread 845 may be configured to form a watertight seal. In one or more embodiments, second connector block proximal thread 845 may comprise a tapered external thread and cable retention mechanism thread 1810 may comprise a tapered internal thread, e.g., second connector block proximal thread 845 and cable retention mechanism thread 1810 may be configured to form a hermetic seal. For example, second connector block proximal thread 845 and cable retention mechanism thread 1810 may be configured to form a watertight seal. Illustratively, a portion of cable retention mechanism 1800 may be disposed in a portion of connector block 800 wherein the portion of cable retention mechanism 1800 is fixed in the portion of connector block 800, e.g., the portion of cable retention mechanism 1800 may be fixed in the portion of connector block 800 by a force of friction. In one or more embodiments, a portion of cable retention mechanism thread 1810 may be disposed in a portion of second connector block proximal thread 845 wherein the portion of cable retention mechanism thread 1810 is fixed in the portion of second connector block proximal thread 845, e.g., the portion of cable retention mechanism thread 1810 may be fixed in the portion of second connector block proximal thread 845 by a force of friction. Illustratively, a portion of cable retention mechanism 1800 may be fixed in a portion of connector block 800 by any suitable fixation means, e.g., a portion of cable retention mechanism 1800 may be fixed in a portion of connector block 800 by an interference fit, a weld, an adhesive, and epoxy, a crimp, a tie, a pin, etc.

In one or more embodiments, disposing cable retention mechanism 1800 in connector block 800 may be configured to dispose a retention lever 1805 in retention mechanism housing 846, e.g., disposing cable retention mechanism 1800 in connector block 800 may be configured to dispose a plurality of retention levers 1805 in retention mechanism housing 846. Illustratively, disposing a retention lever 1805 in retention mechanism housing 846 may be configured to dispose a retention lever 1805 in retention mechanism housing taper 847, e.g., disposing a plurality of retention levers 1805 in retention mechanism housing 846 may be configured to dispose a plurality of retention levers 1805 in retention mechanism housing taper 847. In one or more embodiments, disposing one or more retention levers 1805 in retention mechanism housing taper 847 may be configured to compress one or more retention levers 1805, e.g., as cable retention mechanism 1800 advances into connector block 800 cable retention mechanism distal end 1801 may contact an outer portion of retention mechanism housing taper 847. Illustratively, advancing cable retention mechanism 1800 into connector block 800 after cable retention mechanism distal end 1801 contacts an outer portion of retention mechanism housing taper 847 may be configured to compress one or more retention levers 1805, e.g., advancing cable retention mechanism 1800 into connector block 800 after cable retention mechanism distal end 1801 contacts an outer portion of retention mechanism housing taper 847 may be configured to actuate one or more retention levers 1805 towards a medial axis of cable retention mechanism 1800. In one or more embodiments, advancing cable retention mechanism 1800 into connector block 800 after cable retention mechanism distal end 1801 contacts an outer portion of retention mechanism housing taper 847 may be configured to actuate one or more retention levers 1805 towards a portion of cable 1900, e.g., advancing cable retention mechanism 1800 into connector block 800 after cable retention mechanism distal end 1801 contacts an outer portion of retention mechanism housing taper 847 may be configured to actuate one or more retention surfaces 1840 towards a portion of cable 1900. Illustratively, advancing cable retention mechanism 1800 into connector block 800 after cable retention mechanism distal end 1801 contacts an outer portion of retention mechanism housing taper 847 may be configured to contact one or more retention surfaces 1840 with a portion of cable 1900, e.g., advancing cable retention mechanism 1800 into connector block 800 after cable retention mechanism distal end 1801 contacts an outer portion of retention mechanism housing taper 847 may be configured to contact one or more retention surfaces 1840 with cable jacket 1910.

In one or more embodiments, one or more retention surfaces 1840 may be configured to fix a portion of cable 1900 in cable housing 1830, e.g., one or more retention surfaces 1840 may be configured to fix a portion of cable 1900 in cable housing 1830 by a force of friction. Illustratively, one or more retention surfaces 1840 may comprise an external thread configured to apply a force of friction to a portion of cable 1900, e.g., one or more retention surfaces 1840 may comprise an external thread configured to apply a force of friction to a portion of cable jacket 1910. In one or more embodiments, one or more retention surfaces 1840 may comprise an internal thread configured to apply a force of friction to a portion of cable 1900, e.g., one or more retention surfaces 1840 may comprise an internal thread configured to apply a force of friction to a portion of cable jacket 1910. Illustratively, one or more retention surfaces 1840 may comprise a tapered external thread configured to apply a force of friction to a portion of cable 1900, e.g., one or more retention surfaces 1840 may comprise a tapered external thread configured to form a hermetic seal with a portion of cable 1900. For example, one or more retention surfaces 1840 may comprise a tapered external thread configured to form a watertight seal with a portion of cable 1900. In one or more embodiments, one or more retention surfaces 1840 may comprise a tapered internal thread configured to apply a force of friction to a portion of cable 1900, e.g., one or more retention surfaces 1840 may comprise a tapered internal thread configured to form a hermetic seal with a portion of cable 1900. For example, one or more retention surfaces 1840 may comprise a tapered internal thread configured to form a watertight seal with a portion of cable 1900. Illustratively, cable retention mechanism 1800 may be configured to fix cable 1900 in connector block 800 by any suitable fixation means, e.g., cable retention mechanism 1800 may be configured to fix cable 1900 in connector block 800 by an interference fit, a weld, an adhesive, and epoxy, a crimp, a tie, a pin, etc.

In one or more embodiments, first fluid seal 1400 may be disposed over a portion of connector block 800, e.g., first fluid seal 1400 may be disposed over third seal housing 815. Illustratively, first fluid seal 1400 may be disposed in third seal housing 815 wherein first fluid seal 1400 is disposed between third seal housing distal lip 816 and fixation mechanism base 817, e.g., first fluid seal 1400 may be configured to form a static radial seal. In one or more embodiments, first fluid seal inner diameter 1410 may be disposed in third seal housing 815, e.g., first fluid seal inner diameter 1410 may be disposed in third seal housing 815 wherein first fluid seal inner diameter 1410 is fixed in third seal housing 815. Illustratively, first fluid seal thickness 1430 may be less than a distance between third seal housing distal lip 816 and fixation mechanism base 817, e.g., first fluid seal 1400 may be configured to expand in third seal housing 815. In one or more embodiments, first fluid seal outer diameter 1420 may extend out from third seal housing 815, e.g., first fluid seal 1400 may be configured to expand in third seal housing 815. Illustratively, first fluid seal 1400 may be fixed in third seal housing 815 by any suitable fixation means, e.g., first fluid seal 1400 may be fixed in third seal housing 815 by an interference fit, a weld, an adhesive, and epoxy, a crimp, a tie, a pin, etc.

In one or more embodiments, proximal second fluid seal 1500 may be disposed over a portion of connector block 800, e.g., proximal second fluid seal 1500 may be disposed over second seal housing 810. Illustratively, proximal second fluid seal 1500 may be disposed in second seal housing 810 wherein proximal second fluid seal 1500 is disposed between second seal housing distal lip 811 and second seal housing proximal lip 812, e.g., proximal second fluid seal 1500 may be configured to form a static radial seal. In one or more embodiments, proximal second fluid seal inner diameter 1510 may be disposed in second seal housing 810, e.g., proximal second fluid seal inner diameter 1510 may be disposed in second seal housing 810 wherein proximal second fluid seal inner diameter 1510 is fixed in second seal housing 810. Illustratively, proximal second fluid seal thickness 1530 may be less than a distance between second seal housing distal lip 811 and second seal housing proximal lip 812, e.g., proximal second fluid seal 1500 may be configured to expand in second seal housing 810. In one or more embodiments, proximal second fluid seal outer diameter 1520 may extend out from second seal housing 810, e.g., proximal second fluid seal 1500 may be configured to expand in second seal housing 810. Illustratively, proximal second fluid seal 1500 may be fixed in second seal housing 810 by any suitable fixation means, e.g., proximal second fluid seal 1500 may be fixed in second seal housing 810 by an interference fit, a weld, an adhesive, and epoxy, a crimp, a tie, a pin, etc.

In one or more embodiments, distal second fluid seal 1500 may be disposed over a portion of flange 200, e.g., distal second fluid seal 1500 may be disposed over first seal housing 205. Illustratively, distal second fluid seal 1500 may be disposed in first seal housing 205 wherein distal second fluid seal 1500 is disposed between flange proximal lip 210 and flange distal lip 215, e.g., distal second fluid seal 1500 may be configured to form a static radial seal. In one or more embodiments, distal second fluid seal inner diameter 1510 may be disposed in first seal housing 205, e.g., distal second fluid seal inner diameter 1510 may be disposed in first seal housing 205 wherein distal second fluid seal inner diameter 1510 is fixed in first seal housing 205. Illustratively, distal second fluid seal thickness 1530 may be less than a distance between flange proximal lip 210 and flange distal lip 215, e.g., distal second fluid seal 1500 may be configured to expand in first seal housing 205. In one or more embodiments, distal second fluid seal outer diameter 1520 may extend out from first seal housing 205, e.g., distal second fluid seal 1500 may be configured to expand in first seal housing 205. Illustratively, distal second fluid seal 1500 may be fixed in first seal housing 205 by any suitable fixation means, e.g., distal second fluid seal 1500 may be fixed in first seal housing 205 by an interference fit, a weld, an adhesive, and epoxy, a crimp, a tie, a pin, etc.

In one or more embodiments, transducer sleeve 1200 may be disposed over a portion of connector block 800, inert ring 700, outer electrode stack 600, fourth piezoelectric ring 400, inner electrode stack 600, third piezoelectric ring 400, second piezoelectric ring 400, first piezoelectric ring 400, flange 200, and a portion of amplifier 100, e.g., a portion of connector block 800, inert ring 700, outer electrode stack 600, fourth piezoelectric ring 400, inner electrode stack 600, third piezoelectric ring 400, second piezoelectric ring 400, first piezoelectric ring 400, flange 200, and a portion of amplifier 100 may be disposed in transducer sleeve inner bore 1230. Illustratively, transducer sleeve 1200 may be disposed over a portion of connector block 800 wherein transducer sleeve proximal end 1202 is adjacent to transducer sleeve interface 818, e.g., transducer sleeve 1200 may be disposed over a portion of connector block 800 wherein transducer sleeve proximal end 1202 abuts transducer sleeve interface 818. In one or more embodiments, transducer sleeve 1200 may be disposed over second seal housing proximal lip 812, second seal housing 810, second seal housing distal lip 811, first connector block tool interface 806, second connector block tool interface 807, and connector block distal end 801, e.g., second seal housing proximal lip 812, second seal housing 810, second seal housing distal lip 811, first connector block tool interface 806, second connector block tool interface 807, and connector block distal end 801 may be disposed in transducer sleeve inner bore 1230. For example, transducer sleeve 1200 may be disposed over proximal second fluid seal 1500 and distal second fluid seal 1500. Illustratively, transducer sleeve 1200 may be disposed over proximal second fluid seal 1500, e.g., proximal second fluid seal 1500 may be disposed in transducer sleeve inner bore 1230. In one or more embodiments, transducer sleeve 1200 may be disposed over proximal second fluid seal 1500 wherein proximal second fluid seal 1500 forms a hermetic seal between transducer sleeve 1200 and connector block 800, e.g., transducer sleeve 1200 may be disposed over proximal second fluid seal 1500 wherein proximal second fluid seal 1500 forms a watertight seal between transducer sleeve 1200 and connector block 800. Illustratively, transducer sleeve 1200 may be disposed over proximal second fluid seal 1500 wherein proximal second fluid seal 1500 is disposed between transducer sleeve proximal end 1202 and transducer sleeve distal end 1201, e.g., transducer sleeve 1200 may be disposed over proximal second fluid seal 1500 wherein proximal second fluid seal 1500 is disposed between transducer sleeve proximal end 1202 and connector block distal end 801.

In one or more embodiments, transducer sleeve 1200 may be disposed over inert ring 700 wherein transducer sleeve 1200 is disposed over inert ring distal end 701 and inert ring proximal end 702, e.g., inert ring 700 may be disposed in transducer sleeve inner bore 1230 wherein inert ring distal end 701 and inert ring proximal end 702 are disposed in transducer sleeve inner bore 1230. Illustratively, transducer sleeve 1200 may be disposed over outer electrode stack 500 wherein transducer sleeve 1200 is disposed over outer electrode stack distal end 501 and outer electrode stack proximal end 502, e.g., outer electrode stack 500 may be disposed in transducer sleeve inner bore 1230 wherein outer electrode stack distal end 501 and outer electrode stack proximal end 502 are disposed in transducer sleeve inner bore 1230. In one or more embodiments, transducer sleeve 1200 may be disposed over fourth piezoelectric ring 400 wherein transducer sleeve 1200 is disposed over fourth piezoelectric ring distal end 401 and fourth piezoelectric ring proximal end 402, e.g., fourth piezoelectric ring 400 may be disposed in transducer sleeve inner bore 1230 wherein fourth piezoelectric ring distal end 401 and fourth piezoelectric ring proximal end 402 are disposed in transducer sleeve inner bore 1230. Illustratively, transducer sleeve 1200 may be disposed over inner electrode stack 600 wherein transducer sleeve 1200 is disposed over inner electrode stack distal end 601 and inner electrode stack proximal end 602, e.g., inner electrode stack 600 may be disposed in transducer sleeve inner bore 1230 wherein inner electrode stack distal end 601 and inner electrode stack proximal end 602 are disposed in transducer sleeve inner bore 1230. In one or more embodiments, transducer sleeve 1200 may be disposed over third piezoelectric ring 400 wherein transducer sleeve 1200 is disposed over third piezoelectric ring distal end 401 and third piezoelectric ring proximal end 402, e.g., third piezoelectric ring 400 may be disposed in transducer sleeve inner bore 1230 wherein third piezoelectric ring distal end 401 and third piezoelectric ring proximal end 402 are disposed in transducer sleeve inner bore 1230. Illustratively, transducer sleeve 1200 may be disposed over second piezoelectric ring 400 wherein transducer sleeve 1200 is disposed over second piezoelectric ring distal end 401 and second piezoelectric ring proximal end 402, e.g., second piezoelectric ring 400 may be disposed in transducer sleeve inner bore 1230 wherein second piezoelectric ring distal end 401 and second piezoelectric ring proximal end 402 are disposed in transducer sleeve inner bore 1230. In one or more embodiments, transducer sleeve 1200 may be disposed over first piezoelectric ring 400 wherein transducer sleeve 1200 is disposed over first piezoelectric ring distal end 401 and first piezoelectric ring proximal end 402, e.g., first piezoelectric ring 400 may be disposed in transducer sleeve inner bore 1230 wherein first piezoelectric ring distal end 401 and first piezoelectric ring proximal end 402 are disposed in transducer sleeve inner bore 1230. Illustratively, transducer sleeve 1200 may be disposed over flange 200 wherein transducer sleeve 1200 is disposed over flange distal end 201 and flange proximal end 202, e.g., flange 200 may be disposed in transducer sleeve inner bore 1230 wherein flange distal end 201 and flange proximal end 202 may be disposed in transducer sleeve inner bore 1230. Illustratively, transducer sleeve 1200 may be disposed over distal second fluid seal 1500, e.g., distal second fluid seal 1500 may be disposed in transducer sleeve inner bore 1230. In one or more embodiments, transducer sleeve 1200 may be disposed over distal second fluid seal 1500 wherein distal second fluid seal 1500 forms a hermetic seal between transducer sleeve 1200 and flange 200, e.g., transducer sleeve 1200 may be disposed over distal second fluid seal 1500 wherein distal second fluid seal 1500 forms a watertight seal between transducer sleeve 1200 and flange 200. Illustratively, transducer sleeve 1200 may be disposed over distal second fluid seal 1500 wherein distal second fluid seal 1500 is disposed between transducer sleeve proximal end 1202 and transducer sleeve distal end 1201, e.g., transducer sleeve 1200 may be disposed over distal second fluid seal 1500 wherein distal second fluid seal 1500 is disposed between transducer sleeve distal end 1201 and flange proximal lip 210. In one or more embodiments, transducer sleeve 1200 may be disposed over distal second fluid seal 1500 wherein a distal aperture 1225 is disposed between distal second fluid seal 1500 and transducer sleeve distal end 1201, e.g., transducer sleeve 1200 may be disposed over distal second fluid seal 1500 wherein a plurality of distal apertures 1225 are disposed between distal second fluid seal 1500 and transducer sleeve distal end 1201. Illustratively, transducer sleeve 1200 may be disposed over proximal second fluid seal 1500 and distal second fluid seal 1500 wherein transducer sleeve 1200 is fixed over proximal second fluid seal 1500 and distal second fluid seal 1500, e.g., transducer sleeve 1200 may be fixed over proximal second fluid seal 1500 and distal second fluid seal 1500 by a force of friction, an interference fit, a weld, an adhesive, and epoxy, a crimp, a tie, a pin, etc.

In one or more embodiments, assembled motor 2300 may be configured to convert an electrical energy into a mechanical energy, e.g., assembled motor 2300 may be configured to convert a voltage into a mechanical displacement. Illustratively, a generator may apply a voltage having an ultrasonic frequency between first piezoelectric ring distal end 401 and first piezoelectric ring proximal end 402, e.g., when a polarity of the applied voltage is the same as a first piezoelectric ring 400 poling voltage polarity, then first piezoelectric ring thickness 430 may increase, and when the polarity of the applied voltage is the opposite of the first piezoelectric ring 400 poling voltage polarity, then first piezoelectric ring thickness 430 may decrease. In one or more embodiments, a generator may apply a voltage having an ultrasonic frequency between second piezoelectric ring distal end 401 and second piezoelectric ring proximal end 402, e.g., when a polarity of the applied voltage is the same as a second piezoelectric ring 400 poling voltage polarity, then second piezoelectric ring thickness 430 may increase, and when the polarity of the applied voltage is the opposite of the second piezoelectric ring 400 poling voltage polarity, then second piezoelectric ring thickness 430 may decrease. Illustratively, a generator may apply a voltage having an ultrasonic frequency between third piezoelectric ring distal end 401 and third piezoelectric ring proximal end 402, e.g., when a polarity of the applied voltage is the same as a third piezoelectric ring 400 poling voltage polarity, then third piezoelectric ring thickness 430 may increase, and when the polarity of the applied voltage is the opposite of the third piezoelectric ring 400 poling voltage polarity, then third piezoelectric ring thickness 430 may decrease. In one or more embodiments, a generator may apply a voltage having an ultrasonic frequency between fourth piezoelectric ring distal end 401 and fourth piezoelectric ring proximal end 402, e.g., when a polarity of the applied voltage is the same as a fourth piezoelectric ring 400 poling voltage polarity, then fourth piezoelectric ring thickness 430 may increase, and when the polarity of the applied voltage is the opposite of the fourth piezoelectric ring 400 poling voltage polarity, then fourth piezoelectric ring thickness 430 may decrease. Illustratively, simultaneously increasing first piezoelectric ring thickness 430, second piezoelectric ring thickness 430, third piezoelectric ring thickness 430, and fourth piezoelectric ring thickness 430 may be configured to extend amplifier distal end 101 relative to connector block proximal end 802, e.g., simultaneously increasing first piezoelectric ring thickness 430, second piezoelectric ring thickness 430, third piezoelectric ring thickness 430, and fourth piezoelectric ring thickness 430 may be configured to extend amplifier distal end 101 relative to connector block proximal end 802 by a distance in a range of 7.62 to 40.81 micrometers. For example, simultaneously increasing first piezoelectric ring thickness 430, second piezoelectric ring thickness 430, third piezoelectric ring thickness 430, and fourth piezoelectric ring thickness 430 may be configured to extend amplifier distal end 101 relative to connector block proximal end 802 by a distance of 25.4 micrometers. In one or more embodiments, simultaneously increasing first piezoelectric ring thickness 430, second piezoelectric ring thickness 430, third piezoelectric ring thickness 430, and fourth piezoelectric ring thickness 430 may be configured to extend amplifier distal end 101 relative to connector block proximal end 802 by a distance of less than 7.62 micrometers or greater than 40.81 micrometers. In one or more embodiments, simultaneously decreasing first piezoelectric ring thickness 430, second piezoelectric ring thickness 430, third piezoelectric ring thickness 430, and fourth piezoelectric ring thickness 430 may be configured to retract amplifier distal end 101 relative to connector block proximal end 802, e.g., simultaneously decreasing first piezoelectric ring thickness 430, second piezoelectric ring thickness 430, third piezoelectric ring thickness 430, and fourth piezoelectric ring thickness 430 may be configured to retract amplifier distal end 101 relative to connector block proximal end 802 by a distance in a range of 7.62 to 40.81 micrometers. For example, simultaneously decreasing first piezoelectric ring thickness 430, second piezoelectric ring thickness 430, third piezoelectric ring thickness 430, and fourth piezoelectric ring thickness 430 may be configured to retract amplifier distal end 101 relative to connector block proximal end 802 by a distance of 25.4 micrometers. Illustratively, simultaneously decreasing first piezoelectric ring thickness 430, second piezoelectric ring thickness 430, third piezoelectric ring thickness 430, and fourth piezoelectric ring thickness 430 may be configured to retract amplifier distal end 101 relative to connector block proximal end 802 by a distance of less than 7.62 micrometers or greater than 40.81 micrometers.

In one or more embodiments, simultaneously increasing first piezoelectric ring thickness 430, second piezoelectric ring thickness 430, third piezoelectric ring thickness 430, and fourth piezoelectric ring thickness 430 may be configured to generate a standing wave in assembled motor 2300, e.g., simultaneously decreasing first piezoelectric ring thickness 430, second piezoelectric ring thickness 430, third piezoelectric ring thickness 430, and fourth piezoelectric ring thickness 430 may be configured to generate a standing wave in assembled motor 2300. Illustratively, a first half of a standing wave in assembled motor 2300 may be configured to propagate towards connector block 800 and a second half of a standing wave in assembled motor 2300 may be configured to propagate towards angled adaptor 1300. In one or more embodiments, a portion of assembled motor 2300 may be configured to decrease an amplitude of the first half of the standing wave, e.g., connector block 800 may be configured to decrease an amplitude of the first half of the standing wave by increasing a crosssectional area of a portion of assembled motor 2300.

Illustratively, a reduction of an amplitude of the first half of the standing wave may be configured to reduce an amount of displacement of connector block proximal end 802 relative to amplifier distal end 101, e.g., a reduction of an amplitude of the first half of the standing wave may be configured to reduce a vibration of connector block 800. In one or more embodiments, a portion of assembled motor 2300 may be configured to increase an amplitude of the second half of the standing wave, e.g., amplifier 100 may be configured to increase an amplitude of the second half of the standing wave by decreasing a crosssectional area of a portion of assembled motor 2300. Illustratively, an increase of an amplitude of the second half of the standing wave may be configured to increase an amount of displacement of amplifier distal end 101 relative to connector block proximal end 802, e.g., an increase of an amplitude of the second half of the standing wave may be configured to increase a vibration of amplifier 100.

In one or more embodiments, antinode step 120 may be configured to increase a mechanical displacement of amplifier distal end 101 relative to connector block proximal end 802, e.g., antinode step 120 may be configured to increase a distance that amplifier distal end 101 may extend relative to connector block proximal end 802 and antinode step 120 may be configured to increase a distance that amplifier distal end 101 may retract relative to connector block proximal end 802. Illustratively, antinode step 120 may be disposed at an antinode of assembled motor 2300, e.g., antinode step 120 may be disposed near an antinode of assembled motor 2300. In one or more embodiments, antinode step 120 may be disposed at a point of maximum displacement of a standing wave, e.g., antinode step 120 may be disposed near a point of maximum displacement of a standing wave. Illustratively, antinode step 120 may be configured to increase a cross-sectional area of amplifier 100, e.g., antinode step 120 may be configured to facilitate an availability of an additional cross-sectional area of assembled motor 2300. For example, antinode step 120 may facilitate an availability of an additional cross-sectional area of assembled motor 2300 that may then be reduced, e.g., antinode step 120 may facilitate an availability of an additional cross-sectional area of assembled motor 2300 that may then be reduced to increase a displacement. In one or more embodiments, antinode step 120 may be configured to increase a cross-sectional area of assembled motor 2300 without decreasing an amplitude of the second half of the standing wave, e.g., antinode step 120 may be configured to increase a cross-sectional area of assembled motor 2300 without decreasing an amplitude of the second half of the standing wave by being disposed at or near an antinode of assembled motor 2300.

Figure 24A:
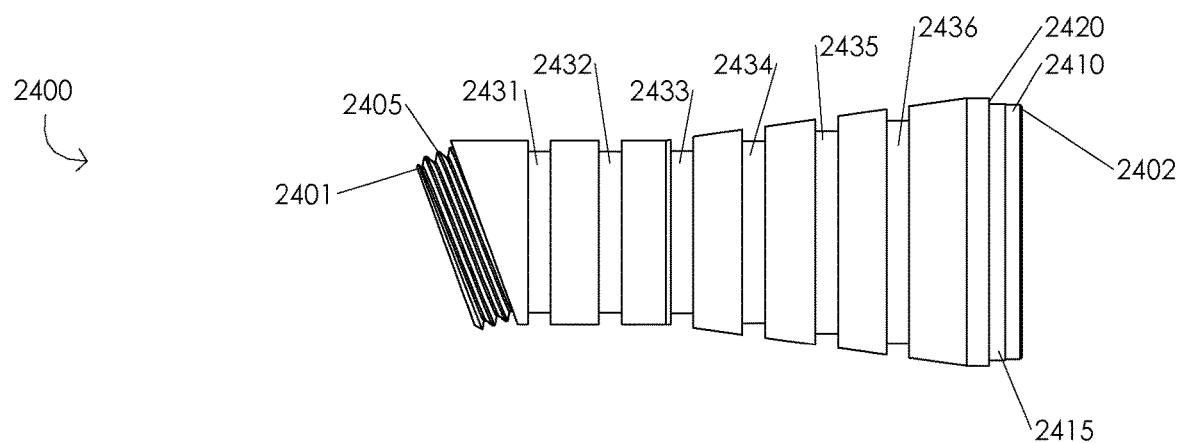
FIGS. 24A and 24B are schematic diagrams illustrating a nosecone.
Figure 24B:
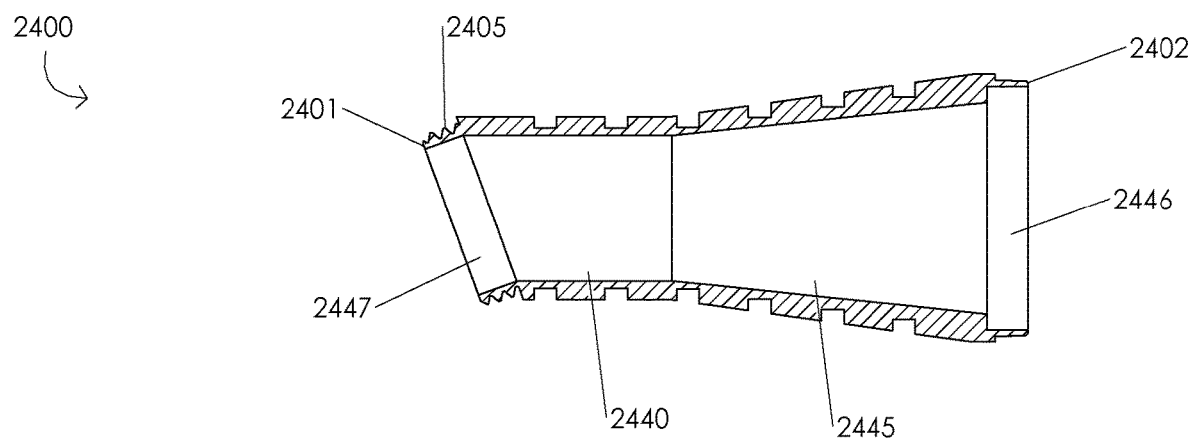

FIGS. 24A and 24B are schematic diagrams illustrating a nosecone 2400. FIG. 24A illustrates a side view of a nosecone 2400. FIG. 24B illustrates a cross-sectional view in a sagittal plane of a nosecone 2400. In one or more embodiments, a nosecone 2400 may comprise a nosecone distal end 2401 and a nosecone proximal end 2402. Illustratively, nosecone 2400 may comprise a nosecone thread 2405. In one or more embodiments, nosecone 2400 may comprise a nosecone proximal taper 2410. Illustratively, nosecone 2400 may comprise a nosecone mount sleeve 2415. In one or more embodiments, nosecone 2400 may comprise a housing sleeve interface 2420. Illustratively, nosecone 2400 may comprise a first nosecone channel 2431. In one or more embodiments, nosecone 2400 may comprise a second nosecone channel 2432. Illustratively, nosecone 2400 may comprise a third nosecone channel 2433. In one or more embodiments, nosecone 2400 may comprise a fourth nosecone channel 2434. Illustratively, nosecone 2400 may comprise a fifth nosecone channel 2435. In one or more embodiments, nosecone 2400 may comprise a sixth nosecone channel 2436. Illustratively, nosecone 2400 may comprise a nosecone distal inner bore 2440. In one or more embodiments, nosecone 2400 may comprise a nosecone proximal inner bore 2445. Illustratively, nosecone 2400 may comprise a transducer sleeve housing 2446. In one or more embodiments, nosecone 2400 may comprise an angled adaptor guide 2447.

In one or more embodiments, nosecone 2400 may be manufactured from any suitable material, e.g., polymers, metals, metal alloys, etc., or from any combination of suitable materials. Illustratively, nosecone 2400 may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, etc. For example, nosecone 2400 may be manufactured from a stainless steel, a brass, a bronze, a duralumin, a nitinol, etc. Illustratively, nosecone 2400 may be manufactured from an underdamped material. In one or more embodiments, nosecone 2400 may be manufactured from a material having a Q factor greater than 0.5. Illustratively, nosecone 2400 may be manufactured from a metal alloy in an annealed condition, e.g., nosecone 2400 may be manufactured from a titanium alloy in an annealed condition. In one or more embodiments, nosecone 2400 may be manufactured from Ti-6Al-4V extra-low interstitials in an annealed condition. Illustratively, flange 200, amplifier 100, inert ring 700, connector block 800, angled adaptor 1300, irrigation barb 1600, aspiration barb 1700, and nosecone 2400 may be manufactured from a same material. In one or more embodiments, flange 200, amplifier 100, inert ring 700, connector block 800, angled adaptor 1300, irrigation barb 1600, aspiration barb 1700, and nosecone 2400 may be manufactured from different materials, e.g., flange 200 may be manufactured from a first material, amplifier 100 may be manufactured from a second material, inert ring 700 may be manufactured from a third material, connector block 800 may be manufactured from a fourth material, angled adaptor 1300 may be manufactured from a fifth material, irrigation barb 1600 may be manufactured from a sixth material, aspiration barb 1700 may be manufactured from a seventh material, and nosecone 2400 may be manufactured from an eighth material.

Figure 25A:
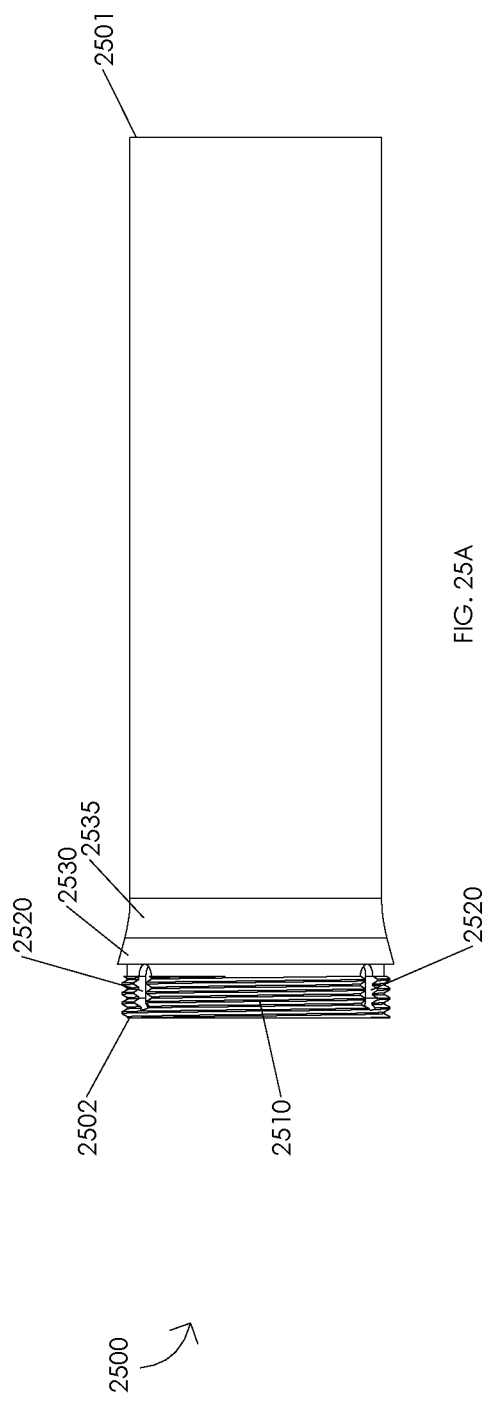
FIGS. 25A and 25B are schematic diagrams illustrating a housing sleeve.
Figure 25B:
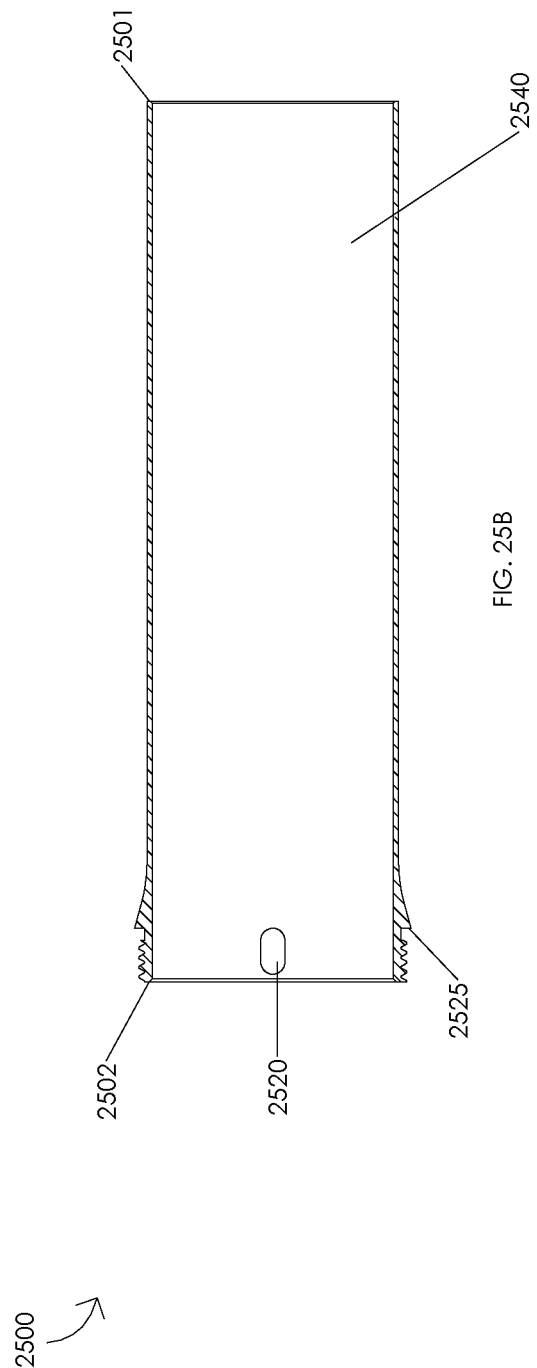

FIGS. 25A and 25B are schematic diagrams illustrating a housing sleeve 2500. FIG. 25A illustrates a side view of a housing sleeve 2500. FIG. 25B illustrates a cross-sectional view in a sagittal plane of a housing sleeve 2500. In one or more embodiments, a housing sleeve 2500 may comprise a housing sleeve distal end 2501 and a housing sleeve proximal end 2502. Illustratively, housing sleeve 2500 may comprise a housing sleeve thread 2510. In one or more embodiments, housing sleeve 2500 may comprise a fixation mechanism guide 2520, e.g., housing sleeve 2500 may comprise a plurality of fixation mechanism guides 2520. Illustratively, housing sleeve 2500 may comprise a collar interface 2525. In one or more embodiments, housing sleeve 2500 may comprise a housing sleeve proximal flange 2530. Illustratively, housing sleeve may comprise a housing sleeve distal flange 2535. In one or more embodiments, housing sleeve 2500 may comprise a housing sleeve inner bore 2540.

In one or more embodiments, housing sleeve 2500 may be manufactured from any suitable material, e.g., polymers, metals, metal alloys, etc., or from any combination of suitable materials. Illustratively, housing sleeve 2500 may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, etc. For example, housing sleeve 2500 may be manufactured from a stainless steel, a brass, a bronze, a duralumin, a nitinol, etc. Illustratively, housing sleeve 2500 may be manufactured from an underdamped material. In one or more embodiments, housing sleeve 2500 may be manufactured from a material having a Q factor greater than 0.5. Illustratively, housing sleeve 2500 may be manufactured from a metal alloy in an annealed condition, e.g., housing sleeve 2500 may be manufactured from a titanium alloy in an annealed condition. In one or more embodiments, housing sleeve 2500 may be manufactured from Ti-6Al-4V extra-low interstitials in an annealed condition. Illustratively, flange 200, amplifier 100, inert ring 700, connector block 800, angled adaptor 1300, irrigation barb 1600, aspiration barb 1700, nosecone 2400, and housing sleeve 2500 may be manufactured from a same material. In one or more embodiments, flange 200, amplifier 100, inert ring 700, connector block 800, angled adaptor 1300, irrigation barb 1600, aspiration barb 1700, nosecone 2400, and housing sleeve 2500 may be manufactured from different materials, e.g., flange 200 may be manufactured from a first material, amplifier 100 may be manufactured from a second material, inert ring 700 may be manufactured from a third material, connector block 800 may be manufactured from a fourth material, angled adaptor 1300 may be manufactured from a fifth material, irrigation barb 1600 may be manufactured from a sixth material, aspiration barb 1700 may be manufactured from a seventh material, nosecone 2400 may be manufactured from an eighth material, and housing sleeve 2500 may be manufactured from a ninth material.

Figure 26A:
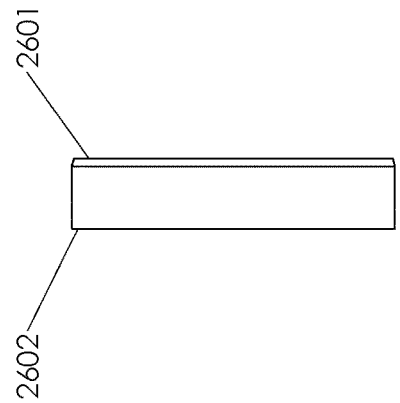
FIGS. 26A, 26B, and 26C are schematic diagrams illustrating a collar.
Figure 26B:
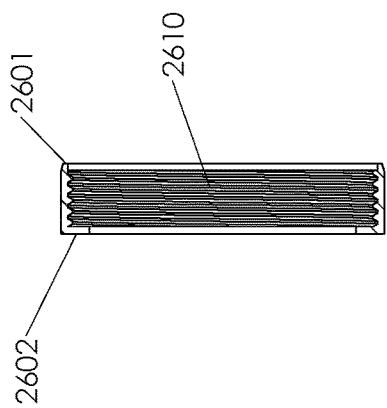
Figure 26C:
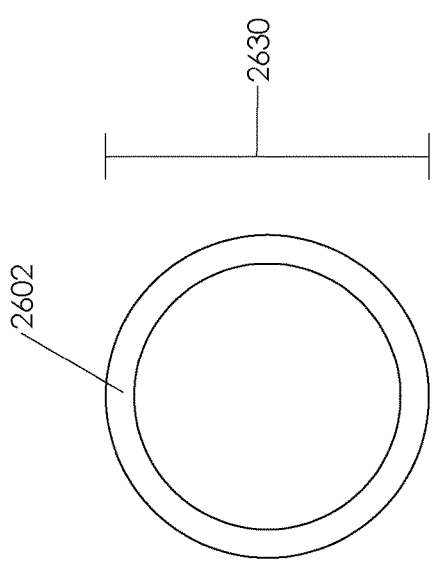

FIGS. 26A, 26B, and 26C are schematic diagrams illustrating a collar 2600. FIG. 26A illustrates a side view of a collar 2600. FIG. 26B illustrates a cross-sectional view in a sagittal plane of a collar 2600. FIG. 26C illustrates a rear view of a collar 2600. In one or more embodiments, a collar 2600 may comprise a collar distal end 2601 and a collar proximal end 2602. Illustratively, collar 2600 may comprise a collar thread 2610. In one or more embodiments, collar 2600 may comprise a collar inner diameter 2620. Illustratively, collar 2600 may comprise a collar outer diameter 2630.

In one or more embodiments, collar 2600 may be manufactured from any suitable material, e.g., polymers, metals, metal alloys, etc., or from any combination of suitable materials. Illustratively, collar 2600 may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, etc. For example, collar 2600 may be manufactured from a stainless steel, a brass, a bronze, a duralumin, a nitinol, etc. Illustratively, collar 2600 may be manufactured from an underdamped material. In one or more embodiments, collar 2600 may be manufactured from a material having a Q factor greater than 0.5. Illustratively, collar 2600 may be manufactured from a metal alloy in an annealed condition, e.g., collar 2600 may be manufactured from a titanium alloy in an annealed condition. In one or more embodiments, collar 2600 may be manufactured from Ti-6Al-4V extra-low interstitials in an annealed condition. Illustratively, flange 200, amplifier 100, inert ring 700, connector block 800, angled adaptor 1300, irrigation barb 1600, aspiration barb 1700, nosecone 2400, housing sleeve 2500, and collar 2600 may be manufactured from a same material. In one or more embodiments, flange 200, amplifier 100, inert ring 700, connector block 800, angled adaptor 1300, irrigation barb 1600, aspiration barb 1700, nosecone 2400, housing sleeve 2500, and collar 2600 may be manufactured from different materials, e.g., flange 200 may be manufactured from a first material, amplifier 100 may be manufactured from a second material, inert ring 700 may be manufactured from a third material, connector block 800 may be manufactured from a fourth material, angled adaptor 1300 may be manufactured from a fifth material, irrigation barb 1600 may be manufactured from a sixth material, aspiration barb 1700 may be manufactured from a seventh material, nosecone 2400 may be manufactured from an eighth material, housing sleeve 2500 may be manufactured from a ninth material, and collar 2600 may be manufactured from a tenth material.

Figure 27B:
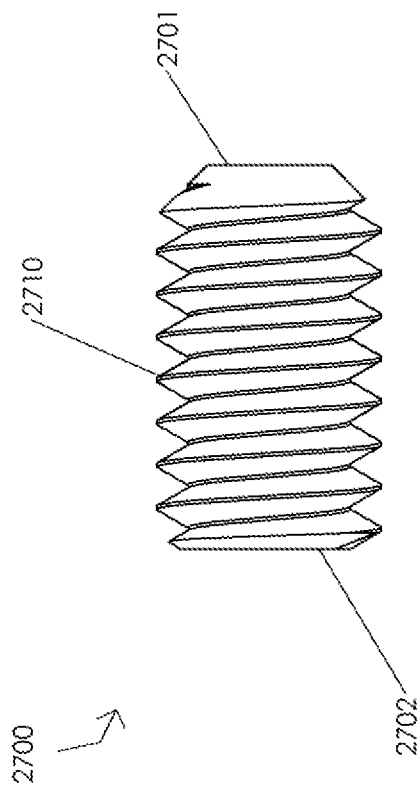
FIGS. 27A and 27B are schematic diagrams illustrating a fixation mechanism.
Figure 27A:
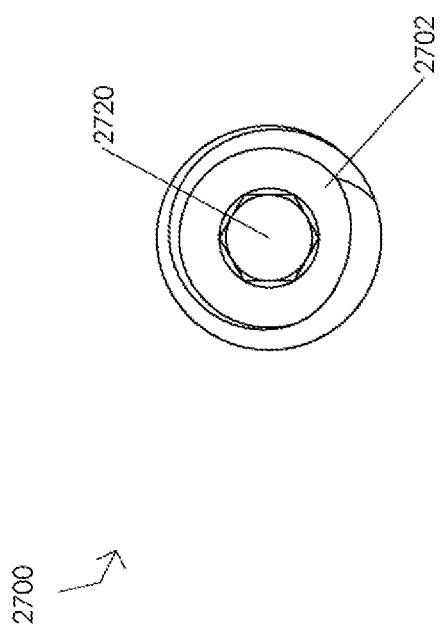

FIGS. 27A and 27B are schematic diagrams illustrating a fixation mechanism 2700. FIG. 27A illustrates a top view of a fixation mechanism 2700. FIG. 27B illustrates a side view of a fixation mechanism 2700. In one or more embodiments, a fixation mechanism 2700 may comprise a fixation mechanism distal end 2701 and a fixation mechanism proximal end 2702. Illustratively, fixation mechanism 2700 may comprise a fixation mechanism thread 2710. In one or more embodiments, fixation mechanism 2700 may comprise a fixation mechanism tool interface 2720.

Figure 28B:
FIGS. 28A and 28B are schematic diagrams illustrating a first nosecone grip.
Figure 28A:
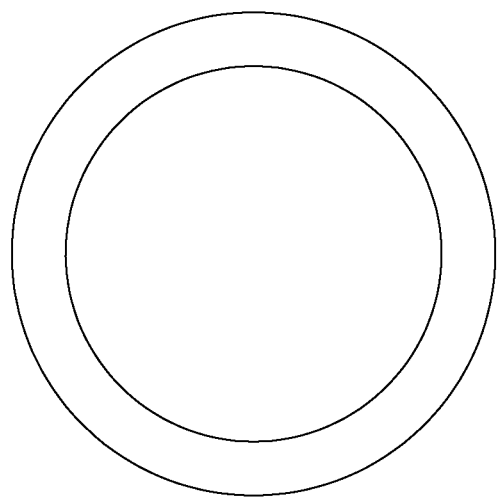

FIGS. 28A and 28B are schematic diagrams illustrating a first nosecone grip 2800. FIG. 28A illustrates a top view of a first nosecone grip 2800. FIG. 28B illustrates a side view of a first nosecone grip 2800. In one or more embodiments, a first nosecone grip 2800 may comprise a first nosecone grip inner diameter 2810. Illustratively, first nosecone grip 2800 may comprise a first nosecone grip outer diameter 2820. In one or more embodiments, first nosecone grip 2800 may comprise a first nosecone grip thickness 2830.

FIGS. 29A and 29B are schematic diagrams illustrating a second nosecone grip 2900. FIG. 29A illustrates a top view of a second nosecone grip 2900. FIG. 29B illustrates a side view of a second nosecone grip 2900. In one or more embodiments, a second nosecone grip 2900 may comprise a second nosecone grip inner diameter 2910. Illustratively, second nosecone grip 2900 may comprise a second nosecone grip outer diameter 2920. In one or more embodiments, second nosecone grip 2900 may comprise a second nosecone grip thickness 2930.

Figure 30:
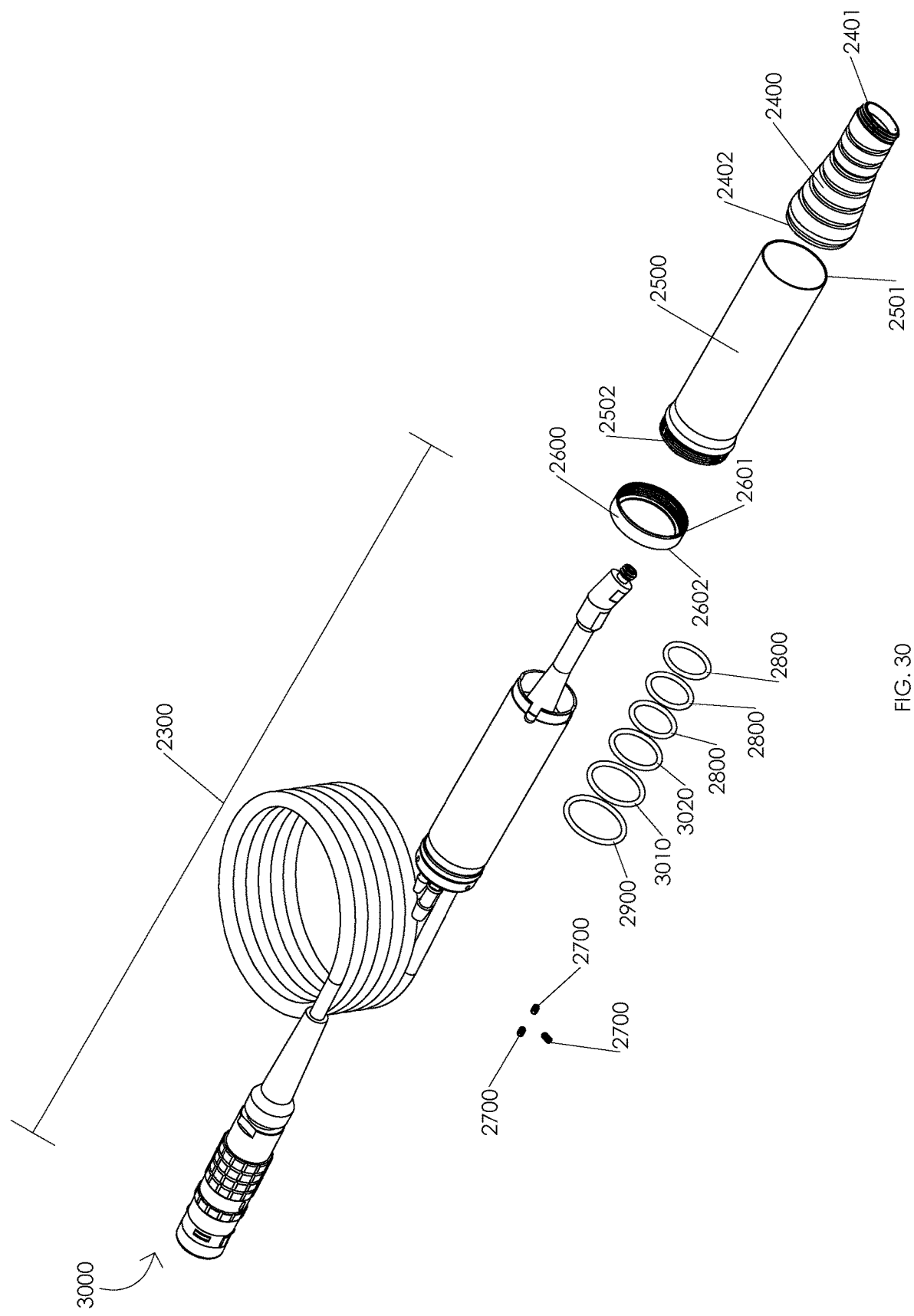
FIG. 30 is a schematic diagram illustrating an exploded view of a handpiece assembly.

FIG. 30 is a schematic diagram illustrating an exploded view of a handpiece assembly 3000. In one or more embodiments, a handpiece assembly 3000 may comprise an assembled motor 2300, a nosecone 2400, a housing sleeve 2500, a collar 2600, a first fixation mechanism 2700, a second fixation mechanism 2700, a third fixation mechanism 2700, a proximal first nosecone grip 2800, a medial first nosecone grip 2800, a distal first nosecone grip 2800, a second nosecone grip 2900, a third nosecone grip 3010, and a fourth nosecone grip 3020.

Figure 31A:
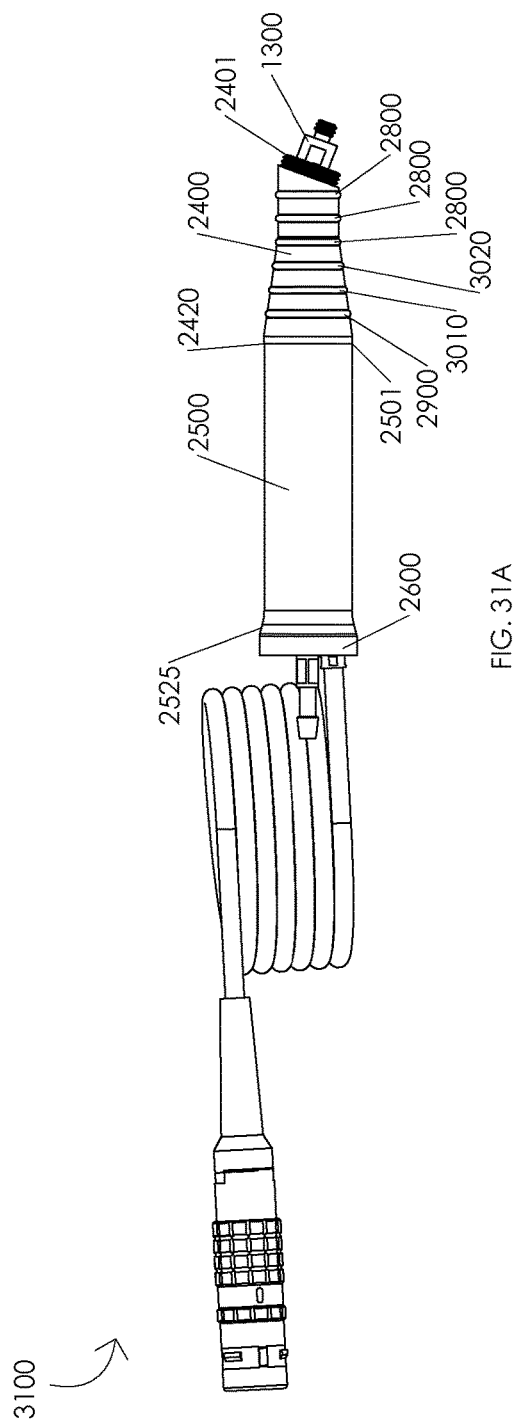
FIGS. 31A and 31B are schematic diagrams illustrating an assembled handpiece.
Figure 31B:
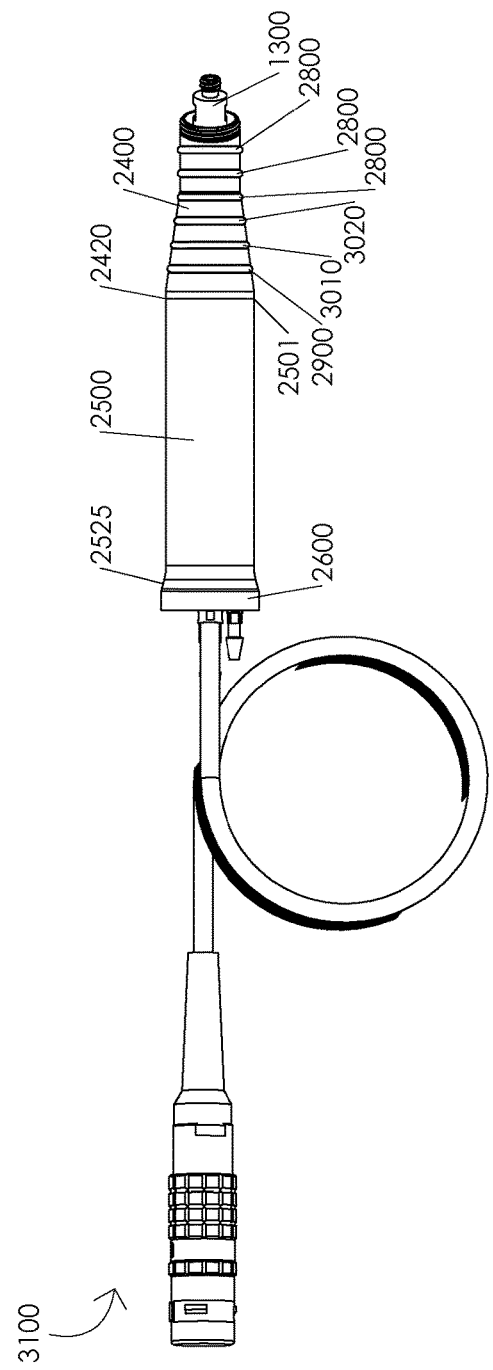

FIGS. 31A and 31B are schematic diagrams illustrating an assembled handpiece 3100. FIG. 31A illustrates a side view of an assembled handpiece 3100. FIG. 31B illustrates a bottom view of an assembled handpiece 3100. In one or more embodiments, a portion of housing sleeve 2500 may be disposed over a portion of transducer sleeve 1200 and a portion of connector block 800, e.g., a portion of transducer sleeve 1200 and a portion of connector block 800 may be disposed in housing sleeve inner bore 2540. Illustratively, housing sleeve 2500 may be disposed over a portion of connector block 800 wherein housing sleeve proximal end 2502 is disposed between connector block proximal end 802 and third seal housing 815, e.g., housing sleeve 2500 may be disposed over a portion of connector block 800 wherein housing sleeve proximal end is disposed over a portion of fixation mechanism base 817. In one or more embodiments, housing sleeve 2500 may be disposed over a portion of connector block 800 wherein housing sleeve proximal end 2502 is disposed between collar mount 820 and third seal housing 815, e.g., housing sleeve 2500 may be disposed over a portion of connector block 800 wherein housing sleeve proximal end 2502 is disposed between offset face 804 and first fixation mechanism housing 821. Illustratively, housing sleeve 2500 may be disposed over a portion of connector block 800 wherein housing sleeve 2500 is disposed over fixation mechanism base 817, first fixation mechanism housing 821, second fixation mechanism housing 822, third fixation mechanism housing 823, third seal housing 815, third seal housing distal lip 816, conduit 805, second seal housing proximal lip 812, second seal housing 810, second seal housing distal lip 811, first connector block tool interface 806, second connector block tool interface 807, and connector block distal end 801, e.g., housing sleeve 2500 may be disposed over a portion of connector block 800 wherein fixation mechanism base 817, first fixation mechanism housing 821, second fixation mechanism housing 822, third fixation mechanism housing 823, third seal housing 815, third seal housing distal lip 816, conduit 805, second seal housing proximal lip 812, second seal housing 810, second seal housing distal lip 811, first connector block tool interface 806, second connector block tool interface 807, and connector block distal end 801 are disposed in housing sleeve inner bore 2540. In one or more embodiments, housing sleeve 2500 may be disposed over a portion of connector block 800 wherein housing sleeve 2500 is disposed over first fluid seal 1400, e.g., first fluid seal 1400 may be disposed in housing sleeve inner bore 2540. Illustratively, first fluid seal 1400 may be disposed between housing sleeve 2500 and connector block 800, e.g., first fluid seal 1400 may be disposed between housing sleeve 2500 and third seal housing 815. In one or more embodiments, housing sleeve 2500 may be disposed over first fluid seal 1400 wherein first fluid seal 1400 forms a hermetic seal between housing sleeve 2500 and connector block 800, e.g., housing sleeve 2500 may be disposed over first fluid seal 1400 wherein first fluid seal 1400 forms a watertight seal between housing sleeve 2500 and connector block 800. Illustratively, housing sleeve 2500 may be disposed over first fluid seal 1400 wherein first fluid seal 1400 is disposed between housing sleeve proximal end 2502 and conduit 805, e.g., an irrigation fluid may egress conduit 805 and flow between transducer sleeve 1200 and housing sleeve 2500. In one or more embodiments, housing sleeve 2500 may be disposed over first fluid seal 1400 wherein housing sleeve 2500 is fixed over first fluid seal 1400, e.g., housing sleeve 2500 may be fixed over first fluid seal 1400 by a force of friction, an interference fit, a weld, an adhesive, and epoxy, a crimp, a tie, a pin, etc. Illustratively, housing sleeve 2500 may be disposed over a portion of connector block 800 wherein a fixation mechanism guide 2520 may be disposed over first fixation mechanism housing 821, e.g., housing sleeve 2500 may be disposed over a portion of connector block 800 wherein a fixation mechanism guide 2520 may be aligned with first fixation mechanism housing 821. In one or more embodiments, a first fixation mechanism guide 2520 may be disposed over first fixation mechanism housing 821, e.g., a first fixation mechanism guide 2520 may be aligned with first fixation mechanism housing 821. Illustratively, a second fixation mechanism guide 2520 may be disposed over second fixation mechanism housing 822, e.g., a second fixation mechanism guide 2520 may be aligned with second fixation mechanism housing 822. In one or more embodiments, a third fixation mechanism guide 2520 may be disposed over third fixation mechanism housing 823, e.g., a third fixation mechanism guide 2520 may be aligned with third fixation mechanism housing 823.

Illustratively, housing sleeve 2500 may be disposed over connector block 800 wherein housing sleeve 2500 is fixed to a portion of connector block 800, e.g., housing sleeve 2500 may be fixed to a portion of connector block 800 by any suitable fixation means. In one or more embodiments, housing sleeve 2500 may be fixed to a portion of connector block 800 by a force of friction, an interference fit, a weld, an adhesive, and epoxy, a crimp, a tie, a pin, etc. Illustratively, fixation mechanism 2700 may be configured to fix housing sleeve 2500 to a portion of connector block 800, e.g., fixation mechanism thread 2710 may be configured to fix housing sleeve 2500 to a portion of connector block 800. In one or more embodiments, a first fixation mechanism 2700 may be disposed in first fixation mechanism guide 2520 and first fixation mechanism housing 821, e.g., a first fixation mechanism 2700 may be configured to fix first fixation mechanism guide 2520 to a portion of connector block 800. Illustratively, a first fixation mechanism 2700 may be fixed in first fixation mechanism guide 2520 and first fixation mechanism housing 821, e.g., a first fixation mechanism 2700 may be fixed in first fixation mechanism guide 2520 and first fixation mechanism housing 821 by a force of friction, an interference fit, a weld, an adhesive, and epoxy, a crimp, a tie, a pin, etc. In one or more embodiments, first fixation mechanism housing 821 may comprise a thread, e.g., first fixation mechanism housing 821 and first fixation mechanism thread 2710 may be configured to convert a torque to a linear force. Illustratively, first fixation mechanism 2700 may comprise a setscrew configured to fix housing sleeve 2500 to a portion of connector block 800. In one or more embodiments, a second fixation mechanism 2700 may be disposed in second fixation mechanism guide 2520 and second fixation mechanism housing 822, e.g., a second fixation mechanism 2700 may be configured to fix second fixation mechanism guide 2520 to a portion of connector block 800. Illustratively, a second fixation mechanism 2700 may be fixed in second fixation mechanism guide 2520 and second fixation mechanism housing 822, e.g., a second fixation mechanism 2700 may be fixed in second fixation mechanism guide 2520 and second fixation mechanism housing 822 by a force of friction, an interference fit, a weld, an adhesive, and epoxy, a crimp, a tie, a pin, etc. In one or more embodiments, second fixation mechanism housing 822 may comprise a thread, e.g., second fixation mechanism housing 822 and second fixation mechanism thread 2710 may be configured to convert a torque to a linear force. Illustratively, second fixation mechanism 2700 may comprise a setscrew configured to fix housing sleeve 2500 to a portion of connector block 800. In one or more embodiments, a third fixation mechanism 2700 may be disposed in third fixation mechanism guide 2520 and third fixation mechanism housing 823, e.g., a third fixation mechanism 2700 may be configured to fix third fixation mechanism guide 2520 to a portion of connector block 800. Illustratively, a third fixation mechanism 2700 may be fixed in third fixation mechanism guide 2520 and third fixation mechanism housing 823, e.g., a third fixation mechanism 2700 may be fixed in third fixation mechanism guide 2520 and third fixation mechanism housing 823 by a force of friction, an interference fit, a weld, an adhesive, and epoxy, a crimp, a tie, a pin, etc. In one or more embodiments, third fixation mechanism housing 823 may comprise a thread, e.g., third fixation mechanism housing 823 and third fixation mechanism thread 2710 may be configured to convert a torque to a linear force. Illustratively, third fixation mechanism 2700 may comprise a setscrew configured to fix housing sleeve 2500 to a portion of connector block 800.

Illustratively, housing sleeve 2500 may be disposed over transducer sleeve 1200 wherein housing sleeve 2500 is disposed over transducer sleeve proximal end 1202, e.g., transducer sleeve 1200 may be disposed in housing sleeve 2500 wherein transducer sleeve proximal end 1202 is disposed in housing sleeve inner bore 2540. In one or more embodiments, housing sleeve 2500 may be disposed over transducer sleeve 1200 wherein transducer sleeve distal end 1201 extends out from housing sleeve distal end 2501, e.g., transducer sleeve 1200 may be disposed in housing sleeve 2500 wherein transducer sleeve distal end 1201 extends out from housing sleeve inner bore 2540. Illustratively, housing sleeve 2500 may be disposed over transducer sleeve 1200 wherein a portion of a distal aperture 1225 extends out from housing sleeve distal end 2501, e.g., transducer sleeve 1200 may be disposed in housing sleeve 2500 wherein a portion of a distal aperture 1225 extends out from housing sleeve inner bore 2540. In one or more embodiments, housing sleeve 2500 may be disposed over transducer sleeve 1200 wherein a portion of a plurality of distal apertures 1225 extend out from housing sleeve distal end 2501, e.g., transducer sleeve 1200 may be disposed in housing sleeve 2500 wherein a portion of a plurality of distal apertures 1225 extend out from housing sleeve inner bore 2540. Illustratively, housing sleeve 2500 may be disposed over transducer sleeve 1200 wherein a portion of nosecone mount 1220 extends out from housing sleeve distal end 2501, e.g., transducer sleeve 1200 may be disposed in housing sleeve 2500 wherein a portion of nosecone mount 1220 extends out from housing sleeve inner bore 2540. In one or more embodiments, housing sleeve 2500 may be disposed over transducer sleeve 1200 wherein a space between housing sleeve 2500 and transducer sleeve 1200 may be configured to guide an irrigation fluid, e.g., an irrigation fluid may ingress a space between housing sleeve 2500 and transducer sleeve 1200 via conduit 805 and the irrigation fluid may egress the space between housing sleeve 2500 and transducer sleeve 1200 via distal aperture 1225.

Illustratively, a portion of collar 2600 may be disposed over a portion of housing sleeve 2500, e.g., a portion of housing sleeve 2500 may be disposed in a portion of collar 2600. In one or more embodiments, a portion of collar 2600 may be disposed over a portion of connector block 800, e.g., a portion of connector block 800 may be disposed in a portion of collar 2600. Illustratively, a portion of collar 2600 may be disposed over collar mount 820, e.g., collar proximal end 2602 may be disposed over collar mount 820. In one or more embodiments, collar 2600 may be disposed over housing sleeve 2500 wherein collar distal end 2601 is adjacent to collar interface 2525, e.g., collar 2600 may be disposed over housing sleeve 2500 wherein collar distal end 2601 abuts collar interface 2525. Illustratively, collar 2600 may be disposed over a portion of connector block 800 and a portion of housing sleeve 2500 wherein collar 2600 is disposed over first fixation mechanism 2700, second fixation mechanism 2700, and third fixation mechanism 2700, e.g., first fixation mechanism 2700, second fixation mechanism 2700, and third fixation mechanism 2700 may be disposed in collar thread 2610. In one or more embodiments, collar 2600 may be disposed over a portion of connector block 800 and a portion of housing sleeve 2500 wherein collar 2600 is disposed over first fixation mechanism guide 2520, second fixation mechanism guide 2520, and third fixation mechanism guide 2520, e.g., first fixation mechanism guide 2520, second fixation mechanism guide 2520, and third fixation mechanism guide 2520 may be disposed in collar thread 2610. For example, collar 2600 may be disposed over a portion of connector block 800 and a portion of housing sleeve 2500 wherein collar 2600 is disposed over first fixation mechanism housing 821, second fixation mechanism housing 822, and third fixation mechanism housing 823, e.g., first fixation mechanism housing 821, second fixation mechanism housing 822, and third fixation mechanism housing 823 may be disposed in collar thread 2610. Illustratively, a portion of housing sleeve thread 2510 may be disposed in a portion of collar thread 2610 wherein the portion of housing sleeve thread 2510 is fixed in the portion of collar thread 2610 by a force of friction, e.g., a portion of collar thread 2610 may be disposed over a portion of housing sleeve thread 2510 wherein the portion of collar thread 2610 is fixed over the portion of housing sleeve thread 2510 by a force of friction. In one or more embodiments, housing sleeve thread 2510 may comprise an external thread and collar thread 2610 may comprise an internal thread, e.g., housing sleeve thread 2510 and collar thread 2610 may be configured to convert a torque to a linear force. Illustratively, collar thread 2610 may comprise an external thread and housing sleeve thread 2510 may comprise an internal thread, e.g., collar thread 2610 and housing sleeve thread 2510 may be configured to convert a torque to a linear force. In one or more embodiments, housing sleeve thread 2510 may comprise a tapered external thread and collar thread 2610 may comprise a tapered internal thread, e.g., housing sleeve thread 2510 and collar thread 2610 may be configured to form a hermetic seal. For example, housing sleeve thread 2510 and collar thread 2610 may be configured to form a watertight seal. Illustratively, collar thread 2610 may comprise a tapered external thread and housing sleeve thread 2510 may comprise a tapered internal thread, e.g., collar thread 2610 and housing sleeve thread 2510 may be configured to form a hermetic seal. For example, collar thread 2610 and housing sleeve thread 2510 may be configured to form a watertight seal. In one or more embodiments, housing sleeve 2500 may be fixed in collar 2600 by any suitable fixation means, e.g., housing sleeve 2500 may be fixed in collar 2600 by a force of friction, an interference fit, a weld, an adhesive, and epoxy, a crimp, a tie, a pin, etc.

Illustratively, second nosecone grip 2900 may be disposed over a portion of nosecone 2400, e.g., second nosecone grip 2900 may be disposed in sixth nosecone channel 2436. In one or more embodiments, second nosecone grip 2900 may be fixed in sixth nosecone channel 2436 by any suitable fixation means, e.g., second nosecone grip 2900 may be fixed in sixth nosecone channel 2436 by a force of friction, an interference fit, a weld, an adhesive, and epoxy, a crimp, a tie, a pin, etc. Illustratively, third nosecone grip 3010 may be disposed over a portion of nosecone 2400, e.g., third nosecone grip 3010 may be disposed in fifth nosecone channel 2435. In one or more embodiments, third nosecone grip 3010 may be fixed in fifth nosecone channel 2435 by any suitable fixation means, e.g., third nosecone grip 3010 may be fixed in fifth nosecone channel 2435 by a force of friction, an interference fit, a weld, an adhesive, and epoxy, a crimp, a tie, a pin, etc. Illustratively, fourth nosecone grip 3020 may be disposed over a portion of nosecone 2400, e.g., fourth nosecone grip 3020 may be disposed in fourth nosecone channel 2434. In one or more embodiments, fourth nosecone grip 3020 may be fixed in fourth nosecone channel 2434 by any suitable fixation means, e.g., fourth nosecone grip 3020 may be fixed in fourth nosecone channel 2434 by a force of friction, an interference fit, a weld, an adhesive, and epoxy, a crimp, a tie, a pin, etc. Illustratively, proximal first nosecone grip 2800 may be disposed over a portion of nosecone 2400, e.g., proximal first nosecone grip 2800 may be disposed in third nosecone channel 2433. In one or more embodiments, proximal first nosecone grip 2800 may be fixed in third nosecone channel 2433 by any suitable fixation means, e.g., proximal first nosecone grip 2800 may be fixed in third nosecone channel 2433 by a force of friction, an interference fit, a weld, an adhesive, and epoxy, a crimp, a tie, a pin, etc. Illustratively, medial first nosecone grip 2800 may be disposed over a portion of nosecone 2400, e.g., medial first nosecone grip 2800 may be disposed in second nosecone channel 2432. In one or more embodiments, medial first nosecone grip 2800 may be fixed in second nosecone channel 2432 by any suitable fixation means, e.g., medial first nosecone grip 2800 may be fixed in second nosecone channel 2432 by a force of friction, an interference fit, a weld, an adhesive, and epoxy, a crimp, a tie, a pin, etc. Illustratively, distal first nosecone grip 2800 may be disposed over a portion of nosecone 2400, e.g., distal first nosecone grip 2800 may be disposed in first nosecone channel 2431. In one or more embodiments, distal first nosecone grip 2800 may be fixed in first nosecone channel 2431 by any suitable fixation means, e.g., distal first nosecone grip 2800 may be fixed in first nosecone channel 2431 by a force of friction, an interference fit, a weld, an adhesive, and epoxy, a crimp, a tie, a pin, etc.

Illustratively, a portion of nosecone 2400 may be disposed in a portion of housing sleeve 2500, e.g., nosecone proximal end 2402 may be disposed in housing sleeve inner bore 2540. In one or more embodiments, a portion of housing sleeve 2500 may be disposed over a portion of nosecone 2400, e.g., housing sleeve distal end 2501 may be disposed over nosecone proximal end 2402. Illustratively, a portion of nosecone 2400 may be disposed in a portion of housing sleeve 2500 wherein housing sleeve distal end 2501 is adjacent to housing sleeve interface 2420, e.g., a portion of nosecone 2400 may be disposed in a portion of housing sleeve 2500 wherein housing sleeve distal end 2501 abuts housing sleeve interface 2420. In one or more embodiments, a portion of transducer sleeve housing 2446 may be disposed in housing sleeve inner bore 2540, e.g., a portion of housing sleeve 2500 may be disposed over a portion of transducer sleeve housing 2446. Illustratively, nosecone proximal taper 2410 may be disposed in a portion of housing sleeve 2500, e.g., nosecone proximal taper 2410 may be configured to guide an interference fit between a portion of nosecone 2400 and a portion of housing sleeve 2500. In one or more embodiments, nosecone proximal taper 2410 may be disposed in housing sleeve inner bore 2540, e.g., a portion of housing sleeve 2500 may be disposed over a portion of nosecone proximal taper 2410. Illustratively, nosecone mount sleeve 2415 may be disposed in a portion of housing sleeve 2500, e.g., nosecone mount sleeve 2415 may be configured to form an interference fit between a portion of nosecone 2400 and a portion of housing sleeve 2500. For example, a portion of nosecone 2400 may be disposed in a portion of housing sleeve 2500 wherein the portion of nosecone 2400 and the portion of housing sleeve form a hermetic seal, e.g., a portion of nosecone 2400 may be disposed in a portion of housing sleeve 2500 wherein the portion of nosecone 2400 and the portion of housing sleeve form a watertight seal. In one or more embodiments, nosecone mount sleeve 2415 may be disposed in housing sleeve inner bore 2540, e.g., a portion of housing sleeve 2500 may be disposed over a portion of nosecone mount sleeve 2415. Illustratively, a portion of nosecone 2400 may be disposed in a portion of housing sleeve 2500 wherein the portion of nosecone 2400 is fixed in the portion of housing sleeve 2500, e.g., the portion of nosecone 2400 may be fixed in the portion of housing sleeve 2500 by a force of friction, an interference fit, a weld, an adhesive, and epoxy, a crimp, a tie, a pin, etc.

In one or more embodiments, a portion of nosecone 2400 may be disposed over a portion of transducer sleeve 1200, e.g., nosecone proximal end 2402 may be disposed over transducer sleeve distal end 1201. Illustratively, nosecone 2400 may be disposed over transducer sleeve 1200 and nosecone may be disposed in housing sleeve 2500, e.g., a portion of nosecone 2400 may be disposed between transducer sleeve 1200 and housing sleeve 2500. In one or more embodiments, a portion of transducer sleeve 1200 may be disposed in a portion of nosecone 2400, e.g., transducer sleeve distal end 1201 may be disposed in transducer sleeve housing 2446. Illustratively, a portion of nosecone 2400 may be disposed over a portion of nosecone mount 1220, e.g., nosecone mount 1220 may be disposed in transducer sleeve housing 2446. In one or more embodiments, transducer sleeve 1200 may be disposed in nosecone 2400 wherein an interface between nosecone proximal inner bore 2445 and transducer sleeve housing 2446 is adjacent to nosecone interface 1215, e.g., transducer sleeve 1200 may be disposed in nosecone 2400 wherein an interface between nosecone proximal inner bore 2445 and transducer sleeve housing 2446 abuts nosecone interface 1215. Illustratively, a portion of transducer sleeve 1200 may be disposed in a portion of nosecone 2400 wherein a portion of a distal aperture 1225 is disposed in nosecone 2400, e.g., a portion of transducer sleeve 1200 may be disposed in a portion of nosecone 2400 wherein a portion of a distal aperture 1225 is disposed in transducer sleeve housing 2446. In one or more embodiments, a portion of transducer sleeve 1200 may be disposed in a portion of nosecone 2400 wherein a portion of a plurality of distal apertures 1225 are disposed in nosecone 2400, e.g., a portion of transducer sleeve 1200 may be disposed in a portion of nosecone 2400 wherein a portion of a plurality of distal apertures 1225 are disposed in transducer sleeve housing 2446. Illustratively, a portion of transducer sleeve 1200 may be disposed in a portion of nosecone 2400 wherein the portion of transducer sleeve 1200 and the portion of nosecone 2400 form a hermetic seal, e.g., a portion of transducer sleeve 1200 may be disposed in a portion of nosecone 2400 wherein the portion of transducer sleeve 1200 and the portion of nosecone 2400 form a hermetic seal. In one or more embodiments, a portion of transducer sleeve 1200 may be disposed in a portion of nosecone 2400 wherein the portion of transducer sleeve 1200 is fixed in the portion of nosecone 2400, e.g., the portion of transducer sleeve 1200 may be fixed in the portion of nosecone 2400 by a force of friction, an interference fit, a weld, an adhesive, and epoxy, a crimp, a tie, a pin, etc.

Illustratively, nosecone 2400 may be disposed over a portion of amplifier 100, e.g., amplifier 100 may be disposed in nosecone proximal inner bore 2445 and nosecone distal inner bore 2440. In one or more embodiments, nosecone 2400 may be disposed over flange interface taper 110, distal base 115, antinode step 120, and amplifier interface 125, e.g., flange interface taper 110, distal base 115, antinode step 120, and amplifier interface 125 may be disposed in nosecone 2400. Illustratively, nosecone 2400 may be disposed over amplifier distal end 101, e.g., amplifier distal end 101 may be disposed in nosecone 2400. In one or more embodiments, nosecone 2400 may be disposed over a portion of angled adaptor 1300, e.g., a portion of angled adaptor 1300 may be disposed in nosecone 2400. Illustratively, nosecone 2400 may be disposed over angled adaptor proximal end 1302, e.g., nosecone 2400 may be disposed over amplifier interface 1325. In one or more embodiments, angled adaptor 1300 may be disposed in nosecone 2400 wherein a portion of angled adaptor 1300 is disposed in angled adaptor guide 2447. Illustratively, angled adaptor 1300 may be disposed in nosecone 2400 wherein a portion of angled adaptor 1300 extends out from nosecone 2400, e.g., angled adaptor 1300 may be disposed in nosecone 2400 wherein angled adaptor distal end 1301 extends out from nosecone distal end 2401. In one or more embodiments, angled adaptor 1300 may be disposed in nosecone 2400 wherein angled adaptor distal thread 1320 extends out from nosecone distal end 2401, e.g., angled adaptor 1300 may be disposed in nosecone 2400 wherein angled tip interface 1330 extends out from nosecone distal end 2401. Illustratively, angled adaptor 1300 may be disposed in nosecone 2400 wherein angled inner bore 1360 extends out from nosecone distal end 2401, e.g., angled adaptor 1300 may be disposed in nosecone 2400 wherein angled inner bore distal bevel 1365 extends out from nosecone distal end 2401.

Illustratively, an irrigation fluid may be configured to ingress an assembled handpiece 3100, e.g., an irrigation fluid may be configured to ingress an assembled handpiece 3100 via irrigation barb 1600. In one or more embodiments, an irrigation fluid may be configured to ingress irrigation barb 1600 via irrigaiton barb distal end 1601, e.g., an irrigation fluid may be configured to ingress irrigation barb inner bore 1650. Illustratively, an irrigation fluid may be configured to egress irrigation barb inner bore 1650, e.g., an irrigation fluid may be configured to egress irrigation barb proximal end 1602. In one or more embodiments, an irrigation fluid may be configured to ingress third connector block proximal thread 850. Illustratively, an irrigation fluid may be configured to egress third connector block proximal thread 850, e.g., an irrigation fluid may be configured to ingress irrigation barb housing 851. In one or more embodiments, an irrigation fluid may be configured to egress irrigation barb housing 851, e.g., an irrigation fluid may be configured to ingress conduit 805. Illustratively, an irrigation fluid may be configured to egress conduit 805, e.g., an irrigation fluid may be configured to ingress a channel disposed between housing sleeve 2500 and transducer sleeve 1200. In one or more embodiments, an irrigation fluid may be configured to egress a channel disposed between housing sleeve 2500 and transducer sleeve 1200, e.g., an irrigation fluid may be configured to ingress a distal aperture 1225. Illustratively, an irrigation fluid may be configured to egress a distal aperture 1225, e.g., an irrigation fluid may be configured to ingress nosecone proximal inner bore 2445. In one or more embodiments, an irrigation fluid may be configured to egress nosecone proximal inner bore 2445, e.g., an irrigation fluid may be configured to ingress nosecone distal inner bore 2440. Illustratively, an irrigation fluid may be configured to egress nosecone distal inner bore 2440, e.g., an irrigation fluid may be configured to ingress angled adaptor guide 2447.

Figure 32:
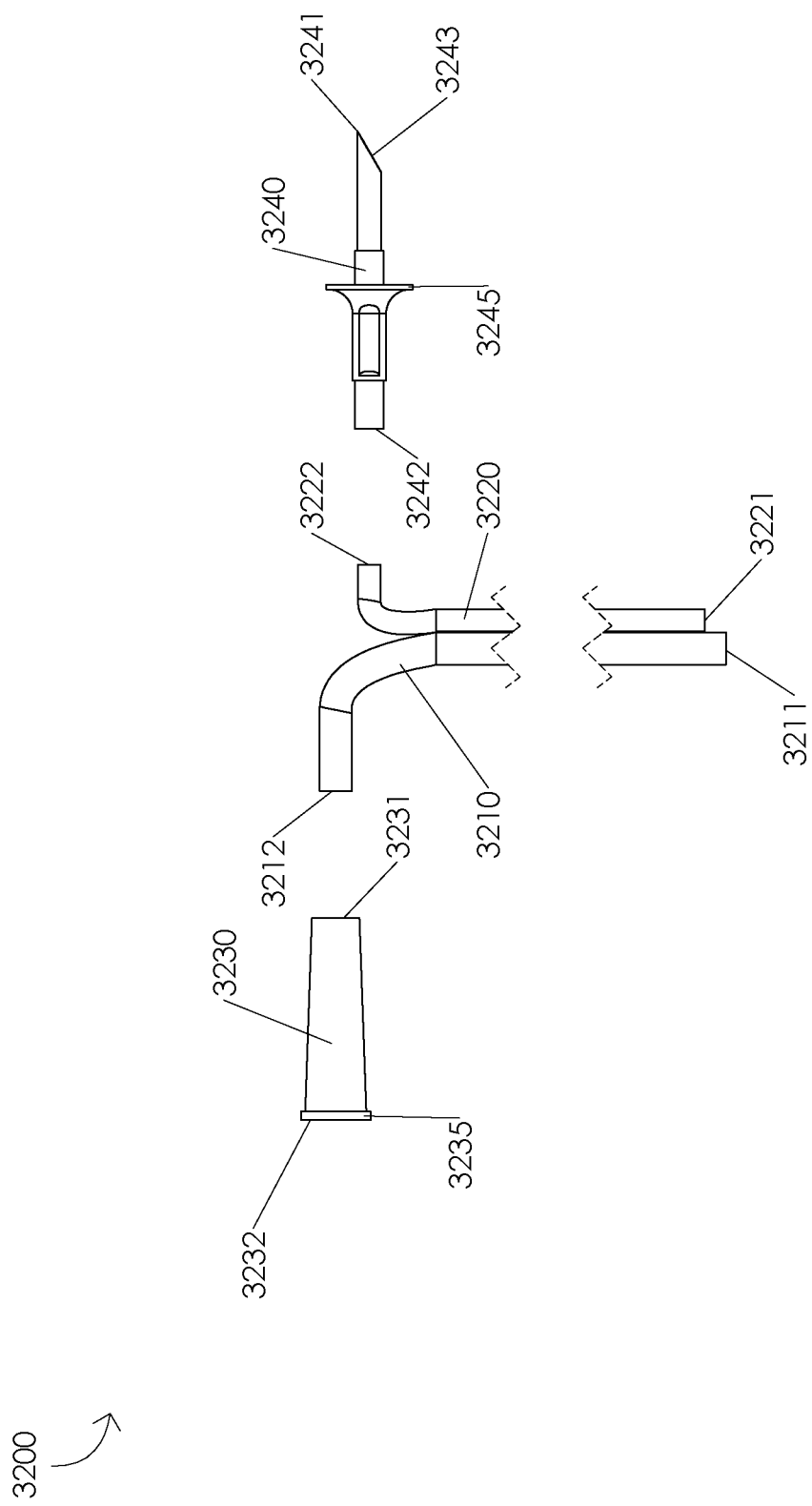
FIG. 32 is a schematic diagram illustrating an exploded view of a tubing set assembly.

FIG. 32 is a schematic diagram illustrating an exploded view of a tubing set assembly 3200. In one or more embodiments, a tubing set assembly may comprise an aspiration tube 3210, an irrigation tube 3220, a canister connector 3230, and an irrigation spike 3240. Illustratively, an aspiration tube 3210 may comprise an aspiration tube distal end 3211 and an aspiration tube proximal end 3212. In one or more embodiments, an irrigation tube 3220 may comprise an irrigation tube distal end 3221 and an irrigation tube proximal end 3222. Illustratively, a canister connector 3230 may comprise a canister connector distal end 3231 and a canister connector proximal end 3232. In one or more embodiments, canister connector 3230 may comprise a canister port interface 3235. Illustratively, an irrigation spike 3240 may comprise an irrigation spike distal end 3241 and an irrigation spike proximal end 3241. In one or more embodiments, irrigation spike 3240 may comprise an irrigation spike edge 3243. Illustratively, irrigation spike 3240 may comprise an irrigation fluid source interface 3245.

Figure 33:
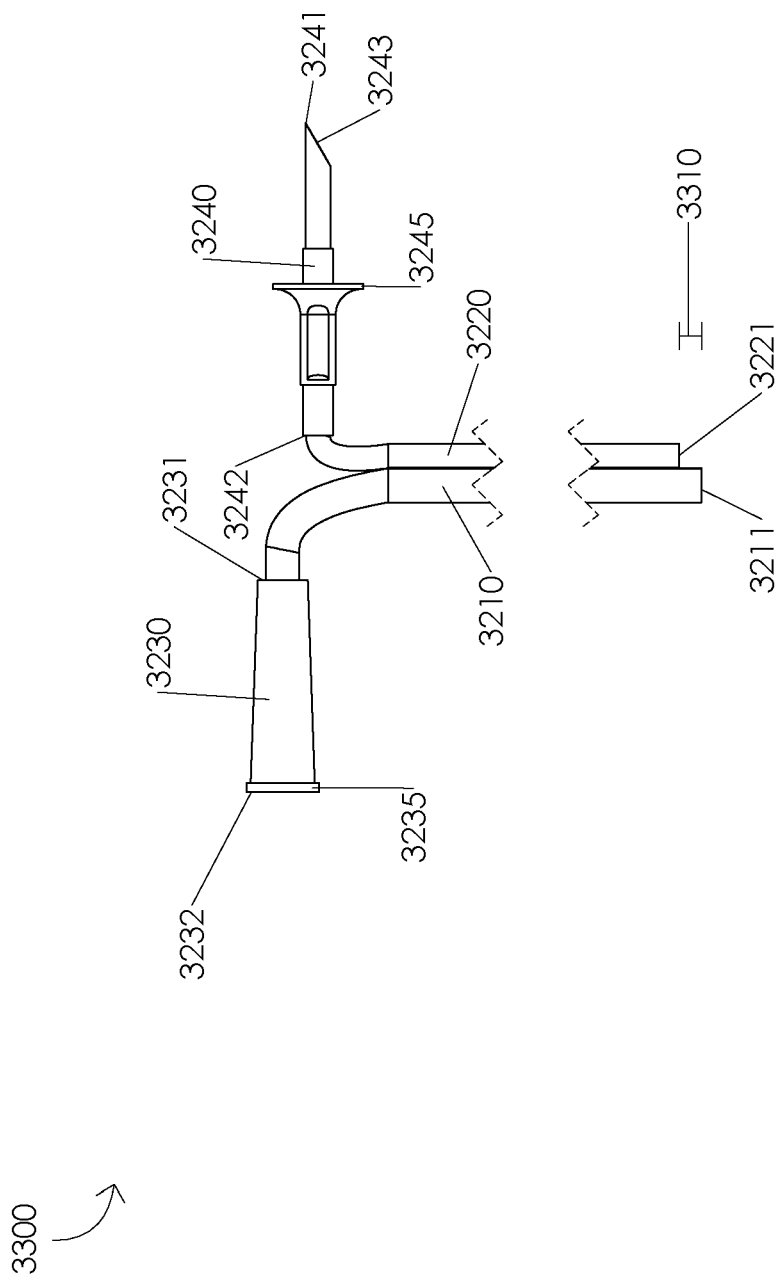
FIG. 33 is a schematic diagram illustrating an assembled tubing set.

FIG. 33 is a schematic diagram illustrating an assembled tubing set 3300. In one or more embodiments, an assembled tubing set 3300 may comprise a tube distal end offset distance 3310. Illustratively, a portion of aspiration tube 3210 may be disposed in a portion of cannister connector 3230, e.g., aspiration tube proximal end 3212 may be disposed in a portion of canister connector 3230. In one or more embodiments, a portion of aspiration tube 3210 may be disposed in a portion of cannister connector 3230 wherein the portion of aspiration tube 3210 is fixed in the portion of cannister connector 3230, e.g., the portion of aspiration tube 3210 may be fixed in the portion of cannister connector 3230 by a force of friction, an interference fit, a weld, an adhesive, and epoxy, a crimp, a tie, a pin, etc. Illustratively, a portion of irrigation tube 3220 may be disposed in a portion of irrigation spike 3240, e.g., irrigation tube proximal end 3222 may be disposed in a portion of irrigation spike 3240. In one or more embodiments, a portion of irrigation tube 3220 may be disposed in a portion of irrigation spike 3240 wherein the portion of irrigation tube 3220 is fixed in the portion of irrigation spike 3240, e.g., the portion of irrigation tube 3220 may be fixed in the portion of irrigation spike 3240 by a force of friction, an interference fit, a weld, an adhesive, and epoxy, a crimp, a tie, a pin, etc.

FIGS. 34A, 34B, and 34C are schematic diagrams illustrating a proximal irrigation sleeve 3400. FIG. 34A illustrates a side view of a proximal irrigation sleeve 3400. FIG. 34B illustrates a cross-sectional view in a sagittal plane of a proximal irrigation sleeve 3400. FIG. 34C illustrates a front view of a proximal irrigation sleeve 3400. In one or more embodiments, a proximal irrigation sleeve 3400 may comprise a proximal irrigation sleeve distal end 3401 and a proximal irrigation sleeve proximal end 3402. Illustratively, proximal irrigation sleeve 3400 may comprise a proximal irrigation sleeve distal thread 3405. In one or more embodiments, proximal irrigation sleeve 3400 may comprise a distal irrigation sleeve interface 3406. Illustratively, proximal irrigation sleeve distal thread 3405 may be disposed between distal irrigation sleeve interface 3406 and proximal irrigation sleeve distal end 3401. In one or more embodiments, proximal irrigation sleeve 3400 may comprise a proximal irrigation sleeve distal undercut 3407. Illustratively, proximal irrigation sleeve distal undercut 3407 may be disposed between distal irrigation sleeve interface 3406 and proximal irrigation sleeve distal thread 3405. In one or more embodiments, proximal irrigation sleeve 3400 may comprise a proximal irrigation sleeve distal base 3410. Illustratively, proximal irrigation sleeve 3400 may comprise a proximal irrigation sleeve distal fillet 3411. In one or more embodiments, proximal irrigation sleeve distal base 3410 may be disposed between proximal irrigation sleeve distal fillet 3411 and proximal irrigation sleeve distal thread 3405. Illustratively, proximal irrigation sleeve 3400 may comprise a proximal irrigation sleeve proximal fillet 3412. In one or more embodiments, proximal irrigation sleeve distal fillet 3411 may be disposed between proximal irrigation sleeve proximal fillet 3412 and proximal irrigation sleeve distal base 3410. Illustratively, proximal irrigation sleeve 3400 may comprise a proximal irrigation sleeve proximal base 3413. In one or more embodiments, proximal irrigation sleeve proximal fillet 3412 may be disposed between proximal irrigation sleeve proximal base 3413 and proximal irrigation sleeve distal fillet 3411.

Illustratively, proximal irrigation sleeve 3400 may comprise a proximal irrigation sleeve proximal thread 3420. In one or more embodiments, proximal irrigation sleeve 3400 may comprise a proximal irrigation sleeve proximal undercut 3421. Illustratively, proximal irrigation sleeve 3400 may comprise a proximal irrigation sleeve inner bore 3425. In one or more embodiments, proximal irrigation sleeve 3400 may comprise a proximal irrigation sleeve distal inner bore 3430. Illustratively, proximal irrigation sleeve 3400 may comprise an alignment mechanism 3440, e.g., proximal irrigation sleeve 3400 may comprise a plurality of alignment mechanisms 3440. In one or more embodiments, proximal irrigation sleeve 3400 may comprise an irrigation fluid guide 3450, e.g., proximal irrigation sleeve 3400 may comprise a plurality of irrigation fluid guides 3450.

In one or more embodiments, proximal irrigation sleeve 3400 may be manufactured from any suitable material, e.g., polymers, metals, metal alloys, etc., or from any combination of suitable materials. Illustratively, proximal irrigation sleeve 3400 may be manufactured from an electrical insulator material. In one or more embodiments, proximal irrigation sleeve 3400 may be manufactured from a thermoplastic polymer material, e.g., proximal irrigation sleeve 3400 may be manufactured from polyether ether ketone, polysulfone, poly(methyl methacrylate), acrylonitrile butadiene styrene, polylactide, polycarbonate, polybenzimidazole, polyetherether ketone, polyoxymethylene, polyether sulfone, polyetherimide, polyethylene, polyphenylene sulfide, polyphenylene oxide, polyvinyl chloride, polytetrafluoroethylene, polypropylene, polystyrene, etc.

Figure 35A:
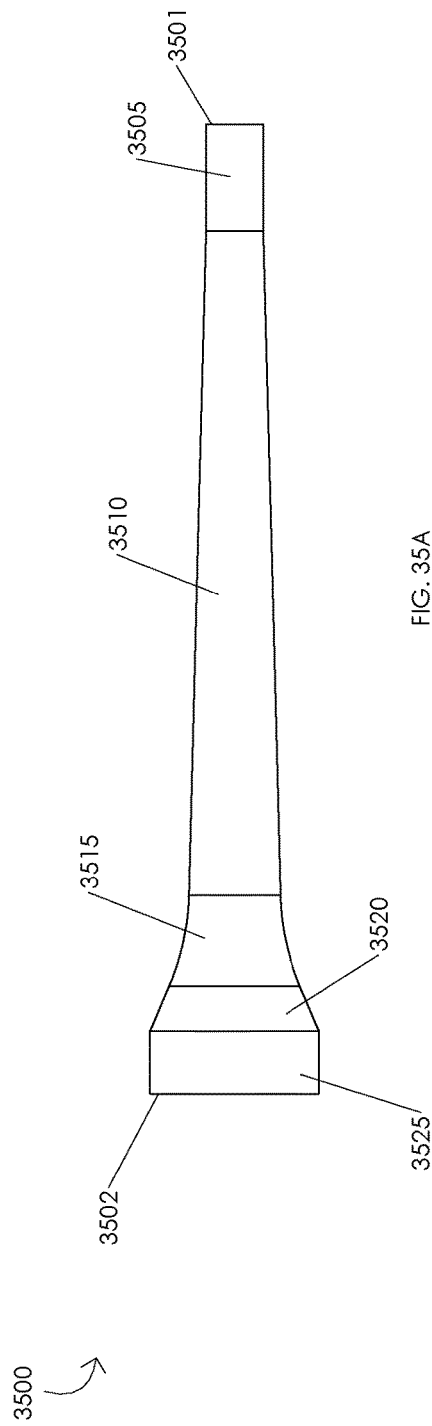
FIGS. 35A and 35B are schematic diagrams illustrating a distal irrigation sleeve.
Figure 35B:
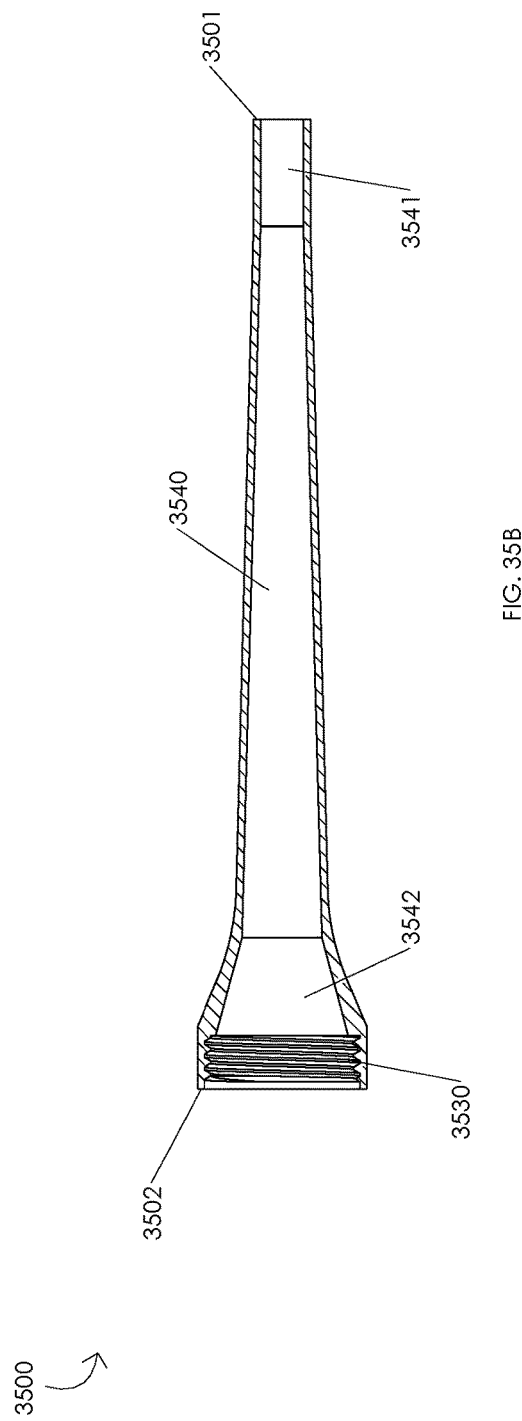

FIGS. 35A and 35B are schematic diagrams illustrating a distal irrigation sleeve 3500. FIG. 35A illustrates a side view of a distal irrigation sleeve 3500. FIG. 35B illustrates a cross-sectional view in a sagittal plane of a distal irrigation sleeve 3500. In one or more embodiments, a distal irrigation sleeve 3500 may comprise a distal irrigation sleeve distal end 3501 and a distal irrigation sleeve proximal end 3502. Illustratively, distal irrigation sleeve 3500 may comprise a distal irrigation sleeve distal base 3505. In one or more embodiments, distal irrigation sleeve 3500 may comprise a distal irrigation sleeve chamfer 3510. Illustratively, distal irrigation sleeve distal base 3505 may be disposed between distal irrigation sleeve chamfer 3510 and distal irrigation sleeve distal end 3501. In one or more embodiments, distal irrigation sleeve 3500 may comprise a distal irrigation sleeve distal fillet 3515. Illustratively, distal irrigation sleeve chamfer 3510 may be disposed between distal irrigation sleeve distal fillet 3515 and distal irrigation sleeve distal base 3505. In one or more embodiments, distal irrigation sleeve 3500 may comprise a distal irrigation sleeve proximal fillet 3520. Illustratively, distal irrigation sleeve distal fillet 3515 may be disposed between distal irrigation sleeve proximal fillet 3520 and distal irrigation sleeve chamfer 3510. In one or more embodiments, distal irrigation sleeve 3500 may comprise a distal irrigation sleeve proximal base 3525. In one or more embodiments, distal irrigation sleeve proximal fillet 3520 may be disposed between distal irrigation sleeve proximal base 3525 and distal irrigation sleeve distal fillet 3515.

Illustratively, distal irrigation sleeve 3500 may comprise a distal irrigation sleeve thread 3530. In one or more embodiments, distal irrigation sleeve 3500 may comprise a distal irrigation sleeve inner bore 3540. Illustratively, distal irrigation sleeve 3500 may comprise a distal irrigation sleeve distal inner bore 3541. In one or more embodiments, distal irrigation sleeve 3500 may comprise a distal irrigation sleeve proximal inner bore 3542. Illustratively, distal irrigation sleeve inner bore 3540 may be disposed between distal irrigation sleeve proximal inner bore 3542 and distal irrigation sleeve distal inner bore 3541.

In one or more embodiments, distal irrigation sleeve 3500 may be manufactured from any suitable material, e.g., polymers, metals, metal alloys, etc., or from any combination of suitable materials. Illustratively, distal irrigation sleeve 3500 may be manufactured from an electrical insulator material. In one or more embodiments, distal irrigation sleeve 3500 may be manufactured from a thermoplastic polymer material, e.g., distal irrigation sleeve 3500 may be manufactured from polyether ether ketone, polysulfone, poly(methyl methacrylate), acrylonitrile butadiene styrene, polylactide, polycarbonate, polybenzimidazole, polyetherether ketone, polyoxymethylene, polyether sulfone, polyetherimide, polyethylene, polyphenylene sulfide, polyphenylene oxide, polyvinyl chloride, polytetrafluoroethylene, polypropylene, polystyrene, etc.

Figure 36A:
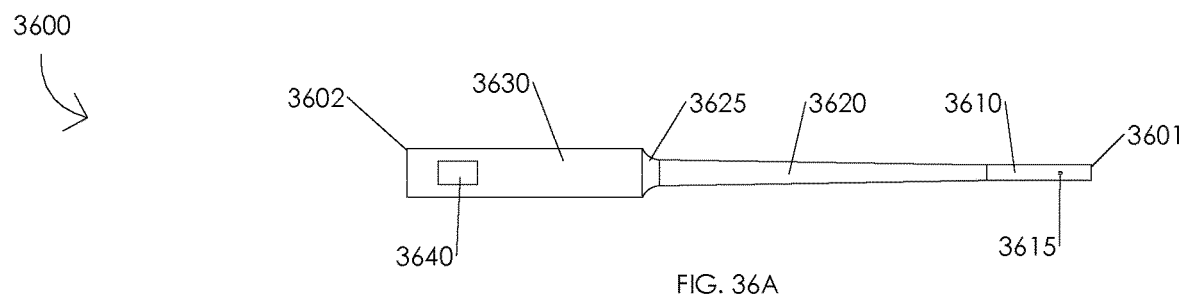
FIGS. 36A and 36B are schematic diagrams illustrating an ultrasonic tip.
Figure 36B:
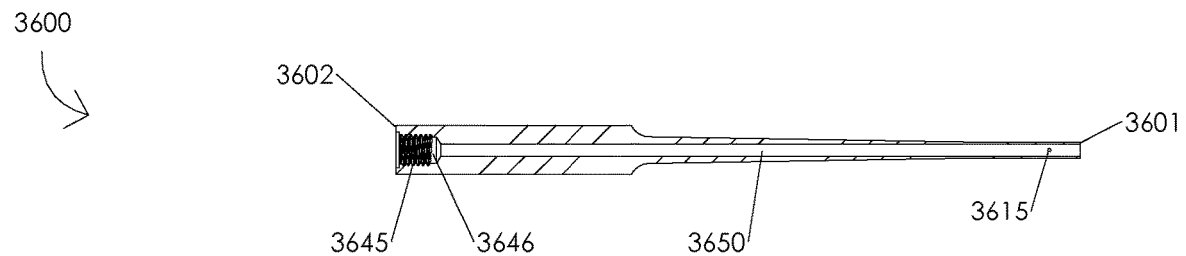

FIGS. 36A and 36B are schematic diagrams illustrating an ultrasonic tip 3600. FIG. 36A illustrates a side view of an ultrasonic tip 3600. FIG. 36B illustrates a cross-sectional view in a sagittal plane of an ultrasonic tip 3600. In one or more embodiments, an ultrasonic tip 3600 may comprise an ultrasonic tip distal end 3601 and an ultrasonic tip proximal end 3602. Illustratively, ultrasonic tip 3600 may comprise an ultrasonic tip distal base 3610. In one or more embodiments, ultrasonic tip 3600 may comprise a pre-aspiration port 3615. Illustratively, ultrasonic tip 3600 may comprise an ultrasonic tip chamfer 3620. In one or more embodiments, ultrasonic tip distal base 3610 may be disposed between ultrasonic tip chamfer 3620 and ultrasonic tip distal end 3601. Illustratively, ultrasonic tip 3600 may comprise an ultrasonic tip fillet 3625. In one or more embodiments, ultrasonic tip chamfer 3620 may be disposed between ultrasonic tip fillet 3625 and ultrasonic tip distal base 3610. Illustratively, ultrasonic tip 3600 may comprise an ultrasonic tip proximal base 3630. In one or more embodiments, ultrasonic tip fillet 3625 may be disposed between ultrasonic tip proximal base 3630 and ultrasonic tip chamfer 3620. Illustratively, ultrasonic tip 3600 may comprise an ultrasonic tip tool interface 3640. In one or more embodiments, ultrasonic tip 3600 may comprise an ultrasonic tip thread 3645. Illustratively, ultrasonic tip 3600 may comprise an angled adaptor temporary housing 3646. In one or more embodiments, ultrasonic tip 3600 may comprise an ultrasonic tip inner bore 3650.

Illustratively, ultrasonic tip 3600 may have an overall length between ultrasonic tip distal end 3601 and ultrasonic tip proximal end 3602 in a range of 3.675 to 5.875 inches, e.g., ultrasonic tip 3600 may have an overall length between ultrasonic tip distal end 3601 and ultrasonic tip proximal end 3602 of 4.375 inches. In one or more embodiments, ultrasonic tip 3600 may have an overall length between ultrasonic tip distal end 3601 and ultrasonic tip proximal end 3602 of less than 3.675 inches or greater than 5.875 inches. Illustratively, ultrasonic tip distal base 3610 may have a length in a range of 0.425 to 0.835 inches, e.g., ultrasonic tip distal base 3610 may have a length of 0.670 inches. In one or more embodiments, ultrasonic tip distal base 3610 may have a length of less than 0.425 inches or greater than 0.835 inches. Illustratively, ultrasonic tip proximal base 3630 may have a length in a range of 1.315 to 1.875 inches, e.g., ultrasonic tip proximal base 3630 may have a length of 1.505 inches. In one or more embodiments, ultrasonic tip proximal base 3630 may have a length of less than 1.315 inches or greater than 1.875 inches. In one or more embodiments, ultrasonic tip 3600 may have a minimum outer diameter in a range of 0.075 to 0.155 inches, e.g., ultrasonic tip 3600 may have a minimum outer diameter of 0.103 inches. For example, ultrasonic tip distal base 3610 may have an outer diameter in a range of 0.075 to 0.155 inches, e.g., ultrasonic tip distal base 3610 may have an outer diameter of 0.103 inches. Illustratively, ultrasonic tip 3600 may have a minimum outer diameter of less than 0.075 inches or greater than 0.155 inches, e.g., ultrasonic tip distal base 3610 may have an outer diameter of less than 0.075 inches or greater than 0.155 inches. In one or more embodiments, ultrasonic tip 3600 may have a maximum outer diameter in a range of 0.225 to 0.455 inches, e.g., ultrasonic tip 3600 may have a maximum outer diameter of 0.315 inches. For example, ultrasonic tip proximal base 3630 may have an outer diameter in a range of 0.225 to 0.455 inches, e.g., ultrasonic tip proximal base 3630 may have an outer diameter of 0.315 inches. Illustratively, ultrasonic tip 3600 may have a maximum outer diameter of less than 0.225 inches or greater than 0.455 inches, e.g., ultrasonic tip proximal base 3630 may have an outer diameter of less than 0.225 inches or greater than 0.455 inches.

In one or more embodiments, ultrasonic tip 3600 may be manufactured from any suitable material, e.g., polymers, metals, metal alloys, etc., or from any combination of suitable materials. Illustratively, ultrasonic tip 3600 may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, etc. For example, ultrasonic tip 3600 may be manufactured from a stainless steel, a brass, a bronze, a duralumin, a nitinol, etc. Illustratively, ultrasonic tip 3600 may be manufactured from an underdamped material. In one or more embodiments, ultrasonic tip 3600 may be manufactured from a material having a Q factor greater than 0.5. Illustratively, ultrasonic tip 3600 may be manufactured from a metal alloy in an annealed condition, e.g., ultrasonic tip 3600 may be manufactured from a titanium alloy in an annealed condition. In one or more embodiments, ultrasonic tip 3600 may be manufactured from Ti-6Al-4V extra-low interstitials in an annealed condition. Illustratively, flange 200, amplifier 100, inert ring 700, connector block 800, angled adaptor 1300, irrigation barb 1600, aspiration barb 1700, nosecone 2400, housing sleeve 2500, collar 2600, and ultrasonic tip 3600 may be manufactured from a same material. In one or more embodiments, flange 200, amplifier 100, inert ring 700, connector block 800, angled adaptor 1300, irrigation barb 1600, aspiration barb 1700, nosecone 2400, housing sleeve 2500, collar 2600, and ultrasonic tip 3600 may be manufactured from different materials, e.g., flange 200 may be manufactured from a first material, amplifier 100 may be manufactured from a second material, inert ring 700 may be manufactured from a third material, connector block 800 may be manufactured from a fourth material, angled adaptor 1300 may be manufactured from a fifth material, irrigation barb 1600 may be manufactured from a sixth material, aspiration barb 1700 may be manufactured from a seventh material, nosecone 2400 may be manufactured from an eighth material, housing sleeve 2500 may be manufactured from a ninth material, collar 2600 may be manufactured from a tenth material, and ultrasonic tip 3600 may be manufactured from an eleventh material.

Figure 37:
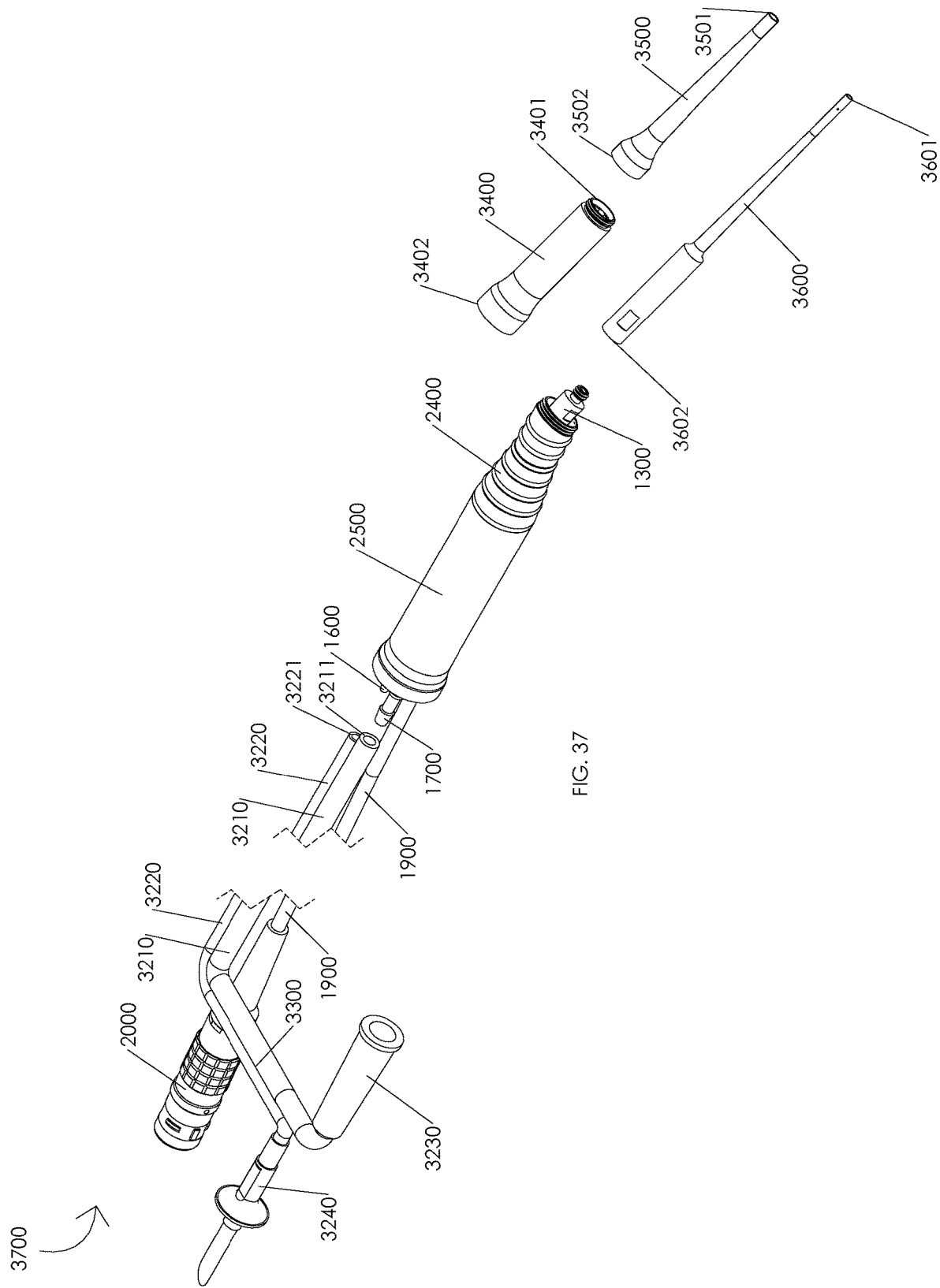
FIG. 37 is a schematic diagram illustrating an exploded view of an ultrasonic handpiece assembly.

FIG. 37 is a schematic diagram illustrating an exploded view of an ultrasonic handpiece assembly 3700. In one or more embodiments, an ultrasonic handpiece assembly 3700 may comprise an assembled handpiece 3100, an assembled tubing set 3300, a proximal irrigation sleeve 3400, a distal irrigation sleeve 3500, and an ultrasonic tip 3600.

Figure 38:
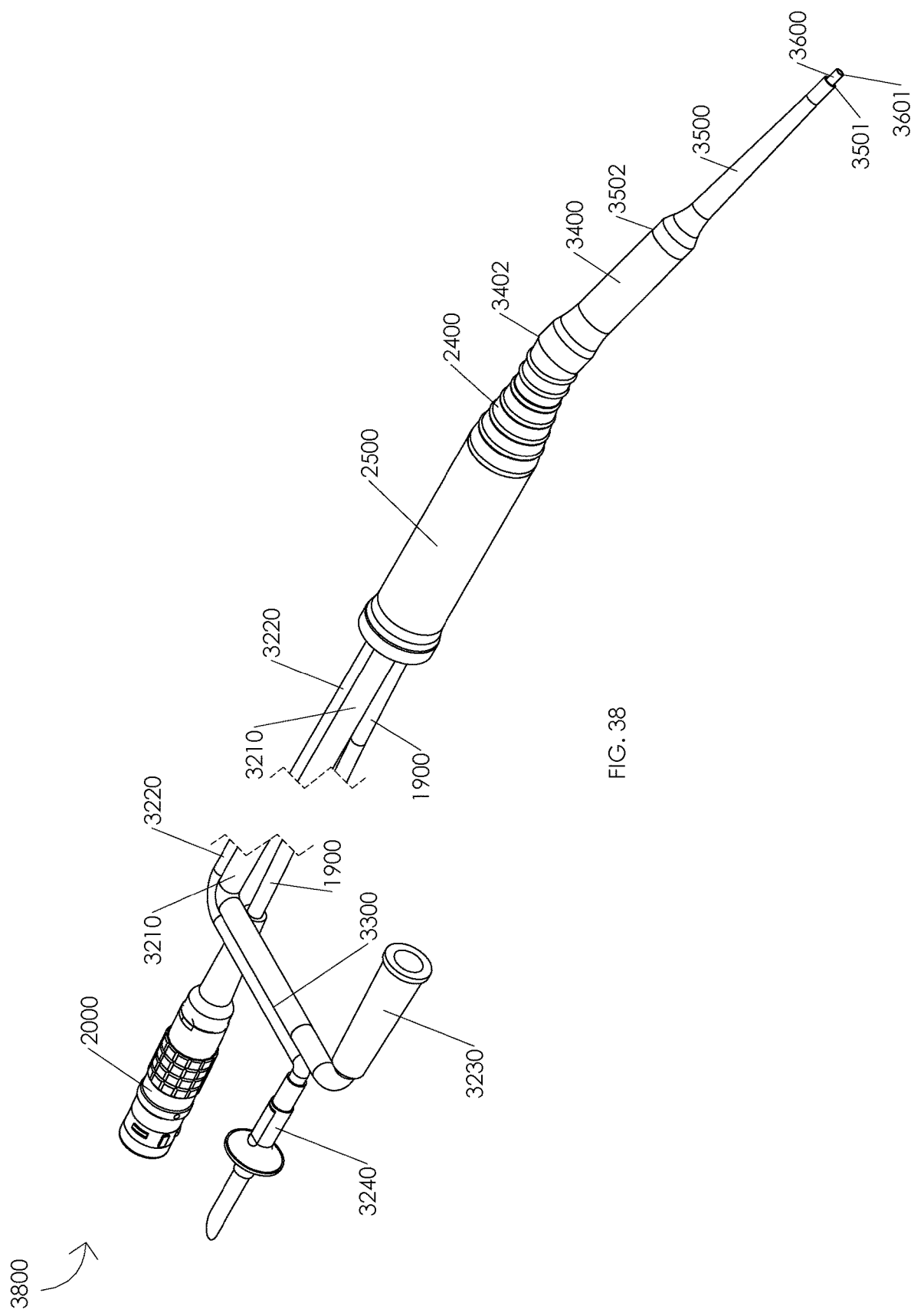
FIG. 38 is a schematic diagram illustrating an assembled ultrasonic handpiece.

FIG. 38 is a schematic diagram illustrating an assembled ultrasonic handpiece 3800. In one or more embodiments, a portion of aspiration tube 3210 may be disposed over a portion of aspiration barb 1700, e.g., aspiration tube distal end 3211 may be disposed over aspiration barb distal end 1701. Illustratively, a portion of aspiration tube 3210 may be disposed over aspiration barb head 1720, e.g., a portion of aspiration tube 3210 may be disposed over aspiration barb chamfer 1721. In one or more embodiments, a portion of aspiration tube 3210 may be disposed over a portion of aspiration barb 1700 wherein the portion of aspiration tube 3210 and the portion of aspiration barb 1700 form a hermetic seal, e.g., a portion of aspiration tube 3210 may be disposed over a portion of aspiration barb 1700 wherein the portion of aspiration tube 3210 and the portion of aspiration barb 1700 form a watertight seal. Illustratively, a portion of aspiration tube 3210 may be disposed over a portion of aspiration barb 1700 wherein the portion of aspiration tube 3210 is fixed to the portion of aspiration barb 1700, e.g., the portion of aspiration tube 3210 may be fixed to the portion of aspiration barb 1700 by a vacuum force, a force of friction, an interference fit, a weld, an adhesive, and epoxy, a crimp, a tie, a pin, etc.

In one or more embodiments, a portion of irrigation tube 3220 may be disposed over a portion of irrigation barb 1600, e.g., irrigation tube distal end 3221 may be disposed over irrigation barb distal end 1601. Illustratively, a portion of irrigation tube 3220 may be disposed over irrigation barb head 1620, e.g., a portion of irrigation tube 3220 may be disposed over irrigation barb chamfer 1621. In one or more embodiments, a portion of irrigation tube 3220 may be disposed over a portion of irrigation barb 1600 wherein the portion of irrigation tube 3220 and the portion of irrigation barb 1600 form a hermetic seal, e.g., a portion of irrigation tube 3220 may be disposed over a portion of irrigation barb 1600 wherein the portion of irrigation tube 3220 and the portion of irrigation barb 1600 form a watertight seal. Illustratively, a portion of irrigation tube 3220 may be disposed over a portion of irrigation barb 1600 wherein the portion of irrigation tube 3220 is fixed to the portion of irrigation barb 1600, e.g., the portion of irrigation tube 3220 may be fixed to the portion of irrigation barb 1600 by a vacuum force, a force of friction, an interference fit, a weld, an adhesive, and epoxy, a crimp, a tie, a pin, etc. In one or more embodiments, tube distal end offset distance 3310 may be configured to prevent a misconnection of assembled tubing set 3300, e.g., tube distal end offset distance 3310 may be configured to prevent a portion of aspiration tube 3210 from being disposed over irrigation barb 1600. Illustratively, tube distal end offset distance 3310 may be configured to prevent a portion of irrigation tube 3220 from being disposed over aspiration barb 1700.

In one or more embodiments, a portion of ultrasonic tip 3600 may be disposed over a portion of angled adaptor 1300, e.g., a portion of angled adaptor 1300 may be disposed in a portion of ultrasonic tip 3600. Illustratively, ultrasonic tip proximal end 3602 may be disposed over a portion of angled adaptor 1300, e.g., angled adaptor distal end 1301 may be disposed in a portion of ultrasonic tip 3600. In one or more embodiments, a portion of ultrasonic tip 3600 may be disposed over a portion of angled adaptor 1300 wherein ultrasonic tip proximal end 3602 is adjacent to angled tip interface 1330, e.g., a portion of ultrasonic tip 3600 may be disposed over a portion of angled adaptor 1300 wherein ultrasonic tip proximal end 3602 is abuts angled tip interface 1330. Illustratively, a portion of ultrasonic tip 3600 may be disposed over a portion of angled adaptor 1300 wherein angled inner bore 1360 is aligned with ultrasonic tip inner bore 3650, e.g., a portion of ultrasonic tip 3600 may be disposed over a portion of angled adaptor 1300 wherein angled inner bore 1360 is colinear with ultrasonic tip inner bore 3650. In one or more embodiments, a portion of angled adaptor 1300 may be fixed in a portion of ultrasonic tip 3600, e.g., angled inner bore distal bevel 1365 may be fixed in angled adaptor temporary housing 3646. Illustratively, a portion of angled adaptor distal thread 1320 may be disposed in a portion of ultrasonic tip thread 3645, e.g., a portion of angled adaptor distal thread 1320 may be fixed in a portion of ultrasonic tip thread 3645. In one or more embodiments, angled adaptor distal thread 1320 may comprise an external thread and ultrasonic tip thread 3645 may comprise an internal thread, e.g., angled adaptor distal thread 1320 and ultrasonic tip thread 3645 may be configured to convert a torque to a linear force. Illustratively, ultrasonic tip thread 3645 may comprise an external thread and angled adaptor distal thread 1320 may comprise an internal thread, e.g. ultrasonic tip thread 3645 and angled adaptor distal thread 1320 may be configured to convert a torque to a linear force. In one or more embodiments, angled adaptor distal thread 1320 may comprise a tapered external thread and ultrasonic tip thread 3645 may comprise a tapered internal thread, e.g., angled adaptor distal thread 1320 and ultrasonic tip thread 3645 may be configured to form a hermetic seal. For example, angled adaptor distal thread 1320 and ultrasonic tip thread 3645 may be configured to form a watertight seal. Illustratively, ultrasonic tip thread 3645 may comprise a tapered external thread and angled adaptor distal thread 1320 may comprise a tapered internal thread, e.g. ultrasonic tip thread 3645 and angled adaptor distal thread 1320 may be configured to form a hermetic seal. For example, ultrasonic tip thread 3645 and angled adaptor distal thread 1320 may be configured to form a watertight seal. In one or more embodiments, a portion of angled adaptor distal thread 1320 may be fixed in a portion of ultrasonic tip thread 3645 by a force of friction. Illustratively, a portion of angled adaptor 1300 may be fixed in a portion of ultrasonic tip 3600 by any suitable fixation means, e.g., the portion of angled adaptor 1300 may be fixed in the portion of ultrasonic tip 3600 by a force of friction, an interference fit, a weld, an adhesive, and epoxy, a crimp, a tie, a pin, etc.

In one or more embodiments, a portion of distal irrigation sleeve 3500 may be disposed over a portion of proximal irrigation sleeve 3400, e.g., a portion of proximal irrigation sleeve 3400 may be disposed in a portion of distal irrigation sleeve 3500. Illustratively, distal irrigation sleeve proximal end 3502 may be disposed over proximal irrigation sleeve distal end 3401, e.g., proximal irrigation sleeve distal end 3401 may be disposed in distal irrigation sleeve proximal inner bore 3542. In one or more embodiments, distal irrigation sleeve 3500 may be disposed over proximal irrigation sleeve 3400 wherein distal irrigation sleeve proximal end 3502 is adjacent to distal irrigation sleeve interface 3406, e.g., distal irrigation sleeve 3500 may be disposed over proximal irrigation sleeve 3400 wherein distal irrigation sleeve proximal end 3502 abuts distal irrigation sleeve interface 3406. Illustratively, distal irrigation sleeve 3500 may be disposed over proximal irrigation sleeve 3400 wherein a portion of distal irrigation sleeve 3500 is disposed over proximal irrigation sleeve distal undercut 3407, e.g., distal irrigation sleeve 3500 may be disposed over proximal irrigation sleeve 3400 wherein a portion of distal irrigation sleeve proximal base 3525 may be disposed over proximal irrigation sleeve distal undercut 3407. In one or more embodiments, a portion of distal irrigation sleeve 3500 may be disposed over a portion of proximal irrigation sleeve 3400 wherein the portion of proximal irrigation sleeve 3400 is fixed in the portion of distal irrigation sleeve 3500, e.g., a portion of distal irrigation sleeve thread 3530 may be disposed over a portion of proximal irrigation sleeve distal thread 3405 wherein the portion of proximal irrigation sleeve distal thread 3405 is fixed in the portion of distal irrigation sleeve thread 3530 by a force of friction. Illustratively, proximal irrigation sleeve distal thread 3405 may comprise an external thread and distal irrigation sleeve thread 3530 may comprise an internal thread, e.g., proximal irrigation sleeve distal thread 3405 and distal irrigation sleeve thread 3530 may be configured to convert a torque to a linear force. In one or more embodiments, distal irrigation sleeve thread 3530 may comprise an external thread and proximal irrigation sleeve distal thread 3405 may comprise an internal thread, e.g., distal irrigation sleeve thread 3530 and proximal irrigation sleeve distal thread 3405 may be configured to convert a torque to a linear force. Illustratively, proximal irrigation sleeve distal thread 3405 may comprise a tapered external thread and distal irrigation sleeve thread 3530 may comprise a tapered internal thread, e.g., proximal irrigation sleeve distal thread 3405 and distal irrigation sleeve thread 3530 may be configured to form a hermetic seal. For example, proximal irrigation sleeve distal thread 3405 and distal irrigation sleeve thread 3530 may be configured to form a watertight seal. In one or more embodiments, distal irrigation sleeve thread 3530 may comprise a tapered external thread and proximal irrigation sleeve distal thread 3405 may comprise a tapered internal thread, e.g., distal irrigation sleeve thread 3530 and proximal irrigation sleeve distal thread 3405 may be configured to form a hermetic seal. For example, distal irrigation sleeve thread 3530 and proximal irrigation sleeve distal thread 3405 may be configured to form a watertight seal. Illustratively, a portion of proximal irrigation sleeve 3400 may be fixed in a portion of distal irrigation sleeve 3500 by any suitable fixation means, e.g., a portion of proximal irrigation sleeve

3400 may be fixed in a portion of distal irrigation sleeve 3500 by force of friction, an interference fit, a weld, an adhesive, and epoxy, a crimp, a tie, a pin, etc.

In one or more embodiments, a portion of proximal irrigation sleeve 3400 may be disposed over a portion of nosecone 2400 wherein ultrasonic tip 3600 is disposed in proximal irrigation sleeve 3400 and distal irrigation sleeve 3500, e.g., proximal irrigation sleeve proximal end 3402 may be disposed over nosecone distal end 2401 wherein ultrasonic tip 3600 is disposed in proximal irrigation sleeve 3400 and distal irrigation sleeve 3500. Illustratively, proximal irrigation sleeve 3400 may be disposed over a portion of nosecone 2400 wherein ultrasonic tip 3600 is disposed in proximal irrigation sleeve inner bore 3425, proximal irrigation sleeve distal inner bore 3430, distal irrigation sleeve proximal inner bore 3542, distal irrigation sleeve inner bore 3540, and distal irrigation sleeve distal inner bore 3541, e.g., proximal irrigation sleeve 3400 may be disposed over a portion of nosecone 2400 wherein ultrasonic tip distal end 3601 extends out from distal irrigation sleeve distal end 3501. In one or more embodiments, proximal irrigation sleeve 3400 may be disposed over a portion of nosecone 2400 wherein preaspiration port 3615 is disposed in distal irrigation sleeve 3500, e.g., proximal irrigation sleeve 3400 may be disposed over a portion of nosecone 2400 wherein preaspiration port 3615 is disposed in distal irrigation sleeve distal inner bore 3541. Illustratively, proximal irrigation sleeve 3400 may be disposed over a portion of nosecone 2400 wherein ultrasonic tip proximal base 3630 is disposed in proximal irrigation sleeve distal inner bore 3430, e.g., proximal irrigation sleeve 3400 may be disposed over a portion of nosecone 2400 wherein ultrasonic tip fillet 3625 is disposed in distal irrigation sleeve proximal inner bore 3542. In one or more embodiments, proximal irrigation sleeve 3400 may be disposed over a portion of nosecone 2400 wherein ultrasonic tip proximal base 3630 is disposed between a first alignment mechanism 3440 and a second alignment mechanism 3440, e.g., proximal irrigation sleeve 3400 may be disposed over a portion of nosecone 2400 wherein ultrasonic tip proximal base 3630 is disposed between a first irrigation fluid guide 3450 and a second irrigation fluid guide 3450.

Illustratively, a first alignment mechanism 3440 and a second alignment mechanism 3440 may be configured to align ultrasonic tip 3600 within proximal irrigation sleeve 3400, e.g., a first alignment mechanism 3440 and a second alignment mechanism 3440 may be configured to align ultrasonic tip 3600 within distal irrigation sleeve 3500. In one or more embodiments, a first alignment mechanism 3440 and a second alignment mechanism 3440 may be configured to align ultrasonic tip 3600 in proximal irrigation sleeve 3400 and distal irrigation sleeve 3500 by preventing an off-axis movement of ultrasonic tip 3600 within proximal irrigation sleeve 3400 and distal irrigation sleeve 3500, e.g., a first alignment mechanism 3440 and a second alignment mechanism 3440 may be configured to align ultrasonic tip 3600 in proximal irrigation sleeve 3400 and distal irrigation sleeve 3500 by preventing an off-axis movement of ultrasonic tip 3600 within proximal irrigation sleeve 3400 and distal irrigation sleeve 3500 without frictional heating between the first alignment mechanism 3440 and ultrasonic tip 3600. For example, a first alignment mechanism 3440 and a second alignment mechanism 3440 may be configured to align ultrasonic tip 3600 in proximal irrigation sleeve 3400 and distal irrigation sleeve 3500 by preventing an off-axis movement of ultrasonic tip 3600 within proximal irrigation sleeve 3400 and distal irrigation sleeve 3500 without frictional heating between the second alignment mechanism 3440 and ultrasonic tip 3600. Illustratively, first alignment mechanism 3440 and second alignment mechanism 3440 may be disposed at or near a node of assembled ultrasonic handpiece 3800. In one or more embodiments, a feature of ultrasonic tip 3600 may be configured to align ultrasonic tip 3600 in proximal irrigation sleeve 3400 and distal irrigation sleeve 3500, e.g., ultrasonic tip 3600 may comprise one or more lateral projections configured to align ultrasonic tip 3600 in proximal irrigation sleeve 3400 and distal irrigation sleeve 3500. Illustratively, ultrasonic tip 3600 may comprise one or more lateral projections configured to align ultrasonic tip 3600 in proximal irrigation sleeve 3400 and distal irrigation sleeve 3500 without frictional heating between the one or more projections of ultrasonic tip 3600 and an inner portion of proximal irrigation sleeve 3400. For example, ultrasonic tip 3600 may comprise one or more lateral projections configured to align ultrasonic tip 3600 in proximal irrigation sleeve 3400 and distal irrigation sleeve 3500 without frictional heating between the one or more projections of ultrasonic tip 3600 and an inner portion of distal irrigation sleeve 3500. In one or more embodiments, ultrasonic tip 3600 may comprise one or more lateral projections disposed at or near a node of assembled ultrasonic handpiece 3800.

Illustratively, a portion of proximal irrigation sleeve proximal base 3413 may be disposed over a portion of angled adaptor guide 2447, e.g., a portion of proximal irrigation sleeve proximal base 3413 may be disposed over a portion of nosecone thread 2405. In one or more embodiments, a portion of proximal irrigation sleeve proximal thread 3420 may be disposed over a portion of nosecone thread 2405, e.g., the portion of proximal irrigation sleeve proximal thread 3420 may be fixed over the portion of nosecone thread 2405 by a force of friction. Illustratively, nosecone thread 2405 may comprise an external thread and proximal irrigation sleeve proximal thread 3420 may comprise an internal thread, e.g., nosecone thread 2405 and proximal irrigation sleeve proximal thread 3420 may be configured to convert a torque to a linear force. In one or more embodiments, proximal irrigation sleeve proximal thread 3420 may comprise an external thread and nosecone thread 2405 may comprise an internal thread, e.g., proximal irrigation sleeve proximal thread 3420 and nosecone thread 2405 may be configured to convert a torque to a linear force. Illustratively, nosecone thread 2405 may comprise a tapered external thread and proximal irrigation sleeve proximal thread 3420 may comprise a tapered internal thread, e.g., nosecone thread 2405 and proximal irrigation sleeve proximal thread 3420 may be configured to form a hermetic seal. For example, nosecone thread 2405 and proximal irrigation sleeve proximal thread 3420 may be configured to form a watertight seal. In one or more embodiments, proximal irrigation sleeve proximal thread 3420 may comprise a tapered external thread and nosecone thread 2405 may comprise a tapered internal thread, e.g., proximal irrigation sleeve proximal thread 3420 and nosecone thread 2405 may be configured to form a hermetic seal. For example, proximal irrigation sleeve proximal thread 3420 and nosecone thread 2405 may be configured to form a watertight seal. Illustratively, a portion of nosecone 2400 may be fixed in a portion of proximal irrigation sleeve 3400 by any suitable fixation means, e.g., a portion of nosecone 2400 may be fixed in a portion of proximal irrigation sleeve 3400 by force of friction, an interference fit, a snap-fit, a weld, an adhesive, and epoxy, a crimp, a tie, a pin, etc.

In one or more embodiments, an assembled ultrasonic handpiece 3800 may be used in a surgical procedure, e.g., an assembled ultrasonic handpiece 3800 may be used to perform a surgical procedure. Illustratively, assembled ultrasonic handpiece 3800 may have an operating frequency in a range of 24500 to 25500 Hz, e.g., assembled ultrasonic handpiece 3800 may have an operating frequency of 25000 Hz. In one or more embodiments, assembled ultrasonic handpiece 3800 may have an operating frequency of less than 24500 Hz or greater than 25500 Hz. Illustratively, assembled ultrasonic handpiece 3800 may be driven by a power in a range of 85 to 110 watts, e.g., assembled ultrasonic handpiece 3800 may be driven by a power of 100 watts. In one or more embodiments, assembled ultrasonic handpiece 3800 may be driven by a power of less than 85 watts or greater than 110 watts.

Illustratively, ultrasonic tip 3600 may have a maximum oscillation amplitude in a range of 355.6 to 660.4 micrometers, e.g., ultrasonic tip 3600 may have a maximum oscillation amplitude of 533.4 micrometers. In one or more embodiments, ultrasonic tip 3600 may have a maximum oscillation amplitude of less than 355.6 micrometers or greater than 660.4 micrometers. Illustratively, ultrasonic tip 3600 may have a maximum oscillation amplitude in a range of 0.320 to 0.594 percent of an overall length of ultrasonic tip 3600, e.g., ultrasonic tip 3600 may have a maximum oscillation amplitude of 0.480 percent of the overall length of ultrasonic tip 3600. In one or more embodiments, ultrasonic tip 3600 may have a maximum oscillation amplitude of less than 0.320 percentt of an overall length of ultrasonic tip 3600 or greater than 0.594 percent of the overall length of ultrasonic tip 3600. Illustratively, ultrasonic tip 3600 may have a maximum oscillation amplitude in a range of 13.922 to 25.243 percent of a minimum outer diameter of ultrasonic tip 3600, e.g., ultrasonic tip 3600 may have a maximum oscillation amplitude of 20.388 percent of the minimum outer diameter of ultrasonic tip 3600. In one or more embodiments, ultrasonic tip 3600 may have a maximum oscillation amplitude of less than 13.922 percent of a minimum outer diameter of ultrasonic tip 3600 or greater than 25.243 percent of the minimum outer diameter of ultrasonic tip 3600. Illustratively, ultrasonic tip 3600 may have a maximum oscillation amplitude in a range of 4.444 to 8.254 percent of a maximum outer diameter of ultrasonic tip 3600, e.g., ultrasonic tip 3600 may have a maximum oscillation amplitude of 6.667 percent of the maximum outer diameter of ultrasonic tip 3600. In one or more embodiments, ultrasonic tip 3600 may have a maximum oscillation amplitude of less than 4.444 percent of a maximum outer diameter of ultrasonic tip 3600 or greater than 8.254 percent of the maxium outer diameter of ultrasonic tip 3600.

Illustratively, ultrasonic tip 3600 may have a maximum oscillation amplitude of greater than 330.2 micrometers, e.g., ultrasonic tip 3600 may have a maximum oscillation amplitude of greater than 330.2 micrometers wherein assembled ultrasonic handpiece 3800 may be configured to maintain the maximum oscillation amplitude for at least 40 seconds. For example, ultrasonic tip 3600 may have a maximum oscillation amplitude of greater than 330.2 micrometers wherein assembled ultrasonic handpiece 3800 may be configured to maintain the maximum oscillation amplitude for at least 400 seconds. Illustratively, ultrasonic tip 3600 may have a maximum oscillation amplitude of greater than 0.297 percent of an overall length of ultrasonic tip 3600, e.g., ultrasonic tip 3600 may have a maximum oscillation amplitude of greater than 0.297 percent of the overall length of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 0.297 percent of an overall length of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 12.621 percent of a minimum outer diameter of ultrasonic tip 3600, e.g., ultrasonic tip 3600 may have a maximum oscillation amplitude of greater than 12.621 percent of the minimum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 12.621 percent of a minimum outer diameter of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 4.127 percent of a maximum outer diameter of ultrasonic tip 3600, e.g., ultrasonic tip 3600 may have a maximum oscillation amplitude of greater than 4.127 percent of the maximum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 4.127 percent of a maximum outer diameter of ultrasonic tip 3600 wherein assembled ultrasonic handpiece 3800 may be configured to maintain the maximum oscillation amplitude for at least 400 seconds.

In one or more embodiments, ultrasonic tip 3600 may have a maximum oscillation amplitude of greater than 355.6 micrometers, e.g., ultrasonic tip 3600 may have a maximum oscillation amplitude of greater than 355.6 micrometers wherein assembled ultrasonic handpiece 3800 may be configured to maintain the maximum oscillation amplitude for at least 40 seconds. For example, ultrasonic tip 3600 may have a maximum oscillation amplitude of greater than 355.6 micrometers wherein assembled ultrasonic handpiece 3800 may be configured to maintain the maximum oscillation amplitude for at least 400 seconds. Illustratively, ultrasonic tip 3600 may have a maximum oscillation amplitude of greater than 0.320 percent of an overall length of ultrasonic tip 3600, e.g., ultrasonic tip 3600 may have a maximum oscillation amplitude of greater than 0.320 percent of the overall length of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 0.320 percent of an overall length of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 13.592 percent of a minimum outer diameter of ultrasonic tip 3600, e.g., ultrasonic tip 3600 may have a maximum oscillation amplitude of greater than 13.592 percent of the minimum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 13.592 percent of a minimum outer diameter of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 4.444 percent of a maximum outer diameter of ultrasonic tip 3600, e.g., ultrasonic tip 3600 may have a maximum oscillation amplitude of greater than 4.444 percent of the maximum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 4.444 percent of a maximum outer diameter of ultrasonic tip 3600 wherein assembled ultrasonic handpiece 3800 may be configured to maintain the maximum oscillation amplitude for at least 400 seconds.

Illustratively, ultrasonic tip 3600 may have a maximum oscillation amplitude of greater than 381.0 micrometers, e.g., ultrasonic tip 3600 may have a maximum oscillation amplitude of greater than 381.0 micrometers wherein assembled ultrasonic handpiece 3800 may be configured to maintain the maximum oscillation amplitude for at least 40 seconds. For example, ultrasonic tip 3600 may have a maximum oscillation amplitude of greater than 381.0 micrometers wherein assembled ultrasonic handpiece 3800 may be configured to maintain the maximum oscillation amplitude for at least 400 seconds. Illustratively, ultrasonic tip 3600 may have a maximum oscillation amplitude of greater than 0.343 percent of an overall length of ultrasonic tip 3600, e.g., ultrasonic tip 3600 may have a maximum oscillation amplitude of greater than 0.343 percent of the overall length of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 0.343 percent of an overall length of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 14.563 percent of a minimum outer diameter of ultrasonic tip 3600, e.g., ultrasonic tip 3600 may have a maximum oscillation amplitude of greater than 14.563 percent of the minimum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 14.563 percent of a minimum outer diameter of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 4.762 percent of a maximum outer diameter of ultrasonic tip 3600, e.g., ultrasonic tip 3600 may have a maximum oscillation amplitude of greater than 4.762 percent of the maximum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 4.762 percent of a maximum outer diameter of ultrasonic tip 3600 wherein assembled ultrasonic handpiece 3800 may be configured to maintain the maximum oscillation amplitude for at least 400 seconds.

In one or more embodiments, ultrasonic tip 3600 may have a maximum oscillation amplitude of greater than 406.4 micrometers, e.g., ultrasonic tip 3600 may have a maximum oscillation amplitude of greater than 406.4 micrometers wherein assembled ultrasonic handpiece 3800 may be configured to maintain the maximum oscillation amplitude for at least 40 seconds. For example, ultrasonic tip 3600 may have a maximum oscillation amplitude of greater than 406.4 micrometers wherein assembled ultrasonic handpiece 3800 may be configured to maintain the maximum oscillation amplitude for at least 400 seconds. Illustratively, ultrasonic tip 3600 may have a maximum oscillation amplitude of greater than 0.366 percent of an overall length of ultrasonic tip 3600, e.g., ultrasonic tip 3600 may have a maximum oscillation amplitude of greater than 0.366 percent of the overall length of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 0.366 percent of an overall length of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 15.534 percent of a minimum outer diameter of ultrasonic tip 3600, e.g., ultrasonic tip 3600 may have a maximum oscillation amplitude of greater than 15.534 percent of the minimum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 15.534 percent of a minimum outer diameter of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 5.079 percent of a maximum outer diameter of ultrasonic tip 3600, e.g., ultrasonic tip 3600 may have a maximum oscillation amplitude of greater than 5.079 percent of the maximum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 5.079 percent of a maximum outer diameter of ultrasonic tip 3600 wherein assembled ultrasonic handpiece 3800 may be configured to maintain the maximum oscillation amplitude for at least 400 seconds.

Illustratively, ultrasonic tip 3600 may have a maximum oscillation amplitude of greater than 431.8 micrometers, e.g., ultrasonic tip 3600 may have a maximum oscillation amplitude of greater than 431.8 micrometers wherein assembled ultrasonic handpiece 3800 may be configured to maintain the maximum oscillation amplitude for at least 40 seconds. For example, ultrasonic tip 3600 may have a maximum oscillation amplitude of greater than 431.8 micrometers wherein assembled ultrasonic handpiece 3800 may be configured to maintain the maximum oscillation amplitude for at least 400 seconds. Illustratively, ultrasonic tip 3600 may have a maximum oscillation amplitude of greater than 0.389 percent of an overall length of ultrasonic tip 3600, e.g., ultrasonic tip 3600 may have a maximum oscillation amplitude of greater than 0.389 percent of the overall length of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 0.389 percent of an overall length of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 16.505 percent of a minimum outer diameter of ultrasonic tip 3600, e.g., ultrasonic tip 3600 may have a maximum oscillation amplitude of greater than 16.505 percent of the minimum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 16.505 percent of a minimum outer diameter of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 5.397 percent of a maximum outer diameter of ultrasonic tip 3600, e.g., ultrasonic tip 3600 may have a maximum oscillation amplitude of greater than 5.397 percent of the maximum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 5.397 percent of a maximum outer diameter of ultrasonic tip 3600 wherein assembled ultrasonic handpiece 3800 may be configured to maintain the maximum oscillation amplitude for at least 400 seconds.

Illustratively, ultrasonic tip 3600 may have a maximum oscillation amplitude of greater than 444.5 micrometers, e.g., ultrasonic tip 3600 may have a maximum oscillation amplitude of greater than 444.5 micrometers wherein assembled ultrasonic handpiece 3800 may be configured to maintain the maximum oscillation amplitude for at least 40 seconds. For example, ultrasonic tip 3600 may have a maximum oscillation amplitude of greater than 444.5 micrometers wherein assembled ultrasonic handpiece 3800 may be configured to maintain the maximum oscillation amplitude for at least 400 seconds. Illustratively, ultrasonic tip 3600 may have a maximum oscillation amplitude of greater than 0.400 percentt of an overall length of ultrasonic tip 3600, e.g., ultrasonic tip 3600 may have a maximum oscillation amplitude of greater than 0.400 percentt of the overall length of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 0.400 percentt of an overall length of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 16.990 percentt of a minimum outer diameter of ultrasonic tip 3600, e.g., ultrasonic tip 3600 may have a maximum oscillation amplitude of greater than 16.990 percentt of the minimum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 16.990 percentt of a minimum outer diameter of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 5.556 percent of a maximum outer diameter of ultrasonic tip 3600, e.g., ultrasonic tip 3600 may have a maximum oscillation amplitude of greater than 5.556 percent of the maximum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 5.556 percent of a maximum outer diameter of ultrasonic tip 3600 wherein assembled ultrasonic handpiece 3800 may be configured to maintain the maximum oscillation amplitude for at least 400 seconds.

In one or more embodiments, ultrasonic tip 3600 may have a maximum oscillation amplitude of greater than 457.2 micrometers, e.g., ultrasonic tip 3600 may have a maximum oscillation amplitude of greater than 457.2 micrometers wherein assembled ultrasonic handpiece 3800 may be configured to maintain the maximum oscillation amplitude for at least 40 seconds. For example, ultrasonic tip 3600 may have a maximum oscillation amplitude of greater than 457.2 micrometers wherein assembled ultrasonic handpiece 3800 may be configured to maintain the maximum oscillation amplitude for at least 400 seconds. Illustratively, ultrasonic tip 3600 may have a maximum oscillation amplitude of greater than 0.411 percent of an overall length of ultrasonic tip 3600, e.g., ultrasonic tip 3600 may have a maximum oscillation amplitude of greater than 0.411 percent of the overall length of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 0.411 percent of an overall length of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 17.476 percent of a minimum outer diameter of ultrasonic tip 3600, e.g., ultrasonic tip 3600 may have a maximum oscillation amplitude of greater than 17.476 percent of the minimum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 17.476 percent of a minimum outer diameter of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 5.714 percent of a maximum outer diameter of ultrasonic tip 3600, e.g., ultrasonic tip 3600 may have a maximum oscillation amplitude of greater than 5.714 percent of the maximum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 5.714 percent of a maximum outer diameter of ultrasonic tip 3600 wherein assembled ultrasonic handpiece 3800 may be configured to maintain the maximum oscillation amplitude for at least 400 seconds.

Illustratively, ultrasonic tip 3600 may have a maximum oscillation amplitude of greater than 482.6 micrometers, e.g., ultrasonic tip 3600 may have a maximum oscillation amplitude of greater than 482.6 micrometers wherein assembled ultrasonic handpiece 3800 may be configured to maintain the maximum oscillation amplitude for at least 40 seconds. For example, ultrasonic tip 3600 may have a maximum oscillation amplitude of greater than 482.6 micrometers wherein assembled ultrasonic handpiece 3800 may be configured to maintain the maximum oscillation amplitude for at least 400 seconds. Illustratively, ultrasonic tip 3600 may have a maximum oscillation amplitude of greater than 0.434 percent of an overall length of ultrasonic tip 3600, e.g., ultrasonic tip 3600 may have a maximum oscillation amplitude of greater than 0.434 percent of the overall length of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 0.434 percent of an overall length of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 18.447 percent of a minimum outer diameter of ultrasonic tip 3600, e.g., ultrasonic tip 3600 may have a maximum oscillation amplitude of greater than 18.447 percent of the minimum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 18.447 percent of a minimum outer diameter of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 6.032 percent of a maximum outer diameter of ultrasonic tip 3600, e.g., ultrasonic tip 3600 may have a maximum oscillation amplitude of greater than 6.032 percent of the maximum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 6.032 percent of a maximum outer diameter of ultrasonic tip 3600 wherein assembled ultrasonic handpiece 3800 may be configured to maintain the maximum oscillation amplitude for at least 400 seconds.

In one or more embodiments, ultrasonic tip 3600 may have a maximum oscillation amplitude of greater than 508.0 micrometers, e.g., ultrasonic tip 3600 may have a maximum oscillation amplitude of greater than 508.0 micrometers wherein assembled ultrasonic handpiece 3800 may be configured to maintain the maximum oscillation amplitude for at least 40 seconds. For example, ultrasonic tip 3600 may have a maximum oscillation amplitude of greater than 508.0 micrometers wherein assembled ultrasonic handpiece 3800 may be configured to maintain the maximum oscillation amplitude for at least 400 seconds. Illustratively, ultrasonic tip 3600 may have a maximum oscillation amplitude of greater than 0.457 percent of an overall length of ultrasonic tip 3600, e.g., ultrasonic tip 3600 may have a maximum oscillation amplitude of greater than 0.457 percent of the overall length of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 0.457 percent of an overall length of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 19.417 percent of a minimum outer diameter of ultrasonic tip 3600, e.g., ultrasonic tip 3600 may have a maximum oscillation amplitude of greater than 19.417 percent of the minimum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 19.417 percent of a minimum outer diameter of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 6.349 percent of a maximum outer diameter of ultrasonic tip 3600, e.g., ultrasonic tip 3600 may have a maximum oscillation amplitude of greater than 6.349 percent of the maximum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 6.349 percent of a maximum outer diameter of ultrasonic tip 3600 wherein assembled ultrasonic handpiece 3800 may be configured to maintain the maximum oscillation amplitude for at least 400 seconds.

Illustratively, ultrasonic tip 3600 may have a maximum oscillation amplitude of greater than 533.4 micrometers, e.g., ultrasonic tip 3600 may have a maximum oscillation amplitude of greater than 533.4 micrometers wherein assembled ultrasonic handpiece 3800 may be configured to maintain the maximum oscillation amplitude for at least 40 seconds. For example, ultrasonic tip 3600 may have a maximum oscillation amplitude of greater than 533.4 micrometers wherein assembled ultrasonic handpiece 3800 may be configured to maintain the maximum oscillation amplitude for at least 400 seconds. Illustratively, ultrasonic tip 3600 may have a maximum oscillation amplitude of greater than 0.480 percentt of an overall length of ultrasonic tip 3600, e.g., ultrasonic tip 3600 may have a maximum oscillation amplitude of greater than 0.480 percentt of the overall length of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 0.480 percentt of an overall length of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 20.388 percent of a minimum outer diameter of ultrasonic tip 3600, e.g., ultrasonic tip 3600 may have a maximum oscillation amplitude of greater than 20.388 percent of the minimum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 20.388 percent of a minimum outer diameter of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 6.667 percent of a maximum outer diameter of ultrasonic tip 3600, e.g., ultrasonic tip 3600 may have a maximum oscillation amplitude of greater than 6.667 percent of the maximum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 6.667 percent of a maximum outer diameter of ultrasonic tip 3600 wherein assembled ultrasonic handpiece 3800 may be configured to maintain the maximum oscillation amplitude for at least 400 seconds.

In one or more embodiments, ultrasonic tip 3600 may have a maximum oscillation amplitude of greater than 558.8 micrometers, e.g., ultrasonic tip 3600 may have a maximum oscillation amplitude of greater than 558.8 micrometers wherein assembled ultrasonic handpiece 3800 may be configured to maintain the maximum oscillation amplitude for at least 40 seconds. For example, ultrasonic tip 3600 may have a maximum oscillation amplitude of greater than 558.8 micrometers wherein assembled ultrasonic handpiece 3800 may be configured to maintain the maximum oscillation amplitude for at least 400 seconds. Illustratively, ultrasonic tip 3600 may have a maximum oscillation amplitude of greater than 0.503 percent of an overall length of ultrasonic tip 3600, e.g., ultrasonic tip 3600 may have a maximum oscillation amplitude of greater than 0.503 percent of the overall length of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 0.503 percent of an overall length of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 21.359 percent of a minimum outer diameter of ultrasonic tip 3600, e.g., ultrasonic tip 3600 may have a maximum oscillation amplitude of greater than 21.359 percent of the minimum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 21.359 percent of a minimum outer diameter of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 6.984 percent of a maximum outer diameter of ultrasonic tip 3600, e.g., ultrasonic tip 3600 may have a maximum oscillation amplitude of greater than 6.984 percent of the maximum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 6.984 percent of a maximum outer diameter of ultrasonic tip 3600 wherein assembled ultrasonic handpiece 3800 may be configured to maintain the maximum oscillation amplitude for at least 400 seconds.

Illustratively, ultrasonic tip 3600 may have a maximum oscillation amplitude of greater than 584.2 micrometers, e.g., ultrasonic tip 3600 may have a maximum oscillation amplitude of greater than 584.2 micrometers wherein assembled ultrasonic handpiece 3800 may be configured to maintain the maximum oscillation amplitude for at least 40 seconds. For example, ultrasonic tip 3600 may have a maximum oscillation amplitude of greater than 584.2 micrometers wherein assembled ultrasonic handpiece 3800 may be configured to maintain the maximum oscillation amplitude for at least 400 seconds. Illustratively, ultrasonic tip 3600 may have a maximum oscillation amplitude of greater than 0.526 percent of an overall length of ultrasonic tip 3600, e.g., ultrasonic tip 3600 may have a maximum oscillation amplitude of greater than 0.526 percent of the overall length of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 0.526 percent of an overall length of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 22.330 percentt of a minimum outer diameter of ultrasonic tip 3600, e.g., ultrasonic tip 3600 may have a maximum oscillation amplitude of greater than 22.330 percentt of the minimum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 22.330 percentt of a minimum outer diameter of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 7.302 percent of a maximum outer diameter of ultrasonic tip 3600, e.g., ultrasonic tip 3600 may have a maximum oscillation amplitude of greater than 7.302 percent of the maximum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 7.302 percent of a maximum outer diameter of ultrasonic tip 3600 wherein assembled ultrasonic handpiece 3800 may be configured to maintain the maximum oscillation amplitude for at least 400 seconds.

In one or more embodiments, ultrasonic tip 3600 may have a maximum oscillation amplitude of greater than 609.6 micrometers, e.g., ultrasonic tip 3600 may have a maximum oscillation amplitude of greater than 609.6 micrometers wherein assembled ultrasonic handpiece 3800 may be configured to maintain the maximum oscillation amplitude for at least 40 seconds. For example, ultrasonic tip 3600 may have a maximum oscillation amplitude of greater than 609.6 micrometers wherein assembled ultrasonic handpiece 3800 may be configured to maintain the maximum oscillation amplitude for at least 400 seconds. Illustratively, ultrasonic tip 3600 may have a maximum oscillation amplitude of greater than 0.549 percent of an overall length of ultrasonic tip 3600, e.g., ultrasonic tip 3600 may have a maximum oscillation amplitude of greater than 0.549 percent of the overall length of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 0.549 percent of an overall length of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 23.301 percent of a minimum outer diameter of ultrasonic tip 3600, e.g., ultrasonic tip 3600 may have a maximum oscillation amplitude of greater than 23.301 percent of the minimum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 23.301 percent of a minimum outer diameter of ultrasonic tip 3600 wherein assembled ultrasonic handpiece 3800 may be configured to maintain the maximum oscillation amplitude for at least 400 seconds. Illustratively, ultrasonic tip 3600 may have a maximum oscillation amplitude of greater than 7.619 percent of a maximum outer diameter of ultrasonic tip 3600, e.g., ultrasonic tip 3600 may have a maximum oscillation amplitude of greater than 7.619 percent of the maximum outer diameter of ultrasonic tip 3600 wherein assembled ultrasonic handpiece 3800 may be configured to maintain the maximum oscillation amplitude for at least 40 seconds. For example, ultrasonic tip 3600 may have a maximum oscillation amplitude of greater than 7.619 percent of a maximum outer diameter of ultrasonic tip 3600 wherein assembled ultrasonic handpiece 3800 may be configured to maintain the maximum oscillation amplitude for at least 400 seconds.

Illustratively, ultrasonic tip 3600 may be configured to increase a displacement of assembled motor 2300, e.g., ultrasonic tip 3600 may be configured to increase a displacement of ultrasonic tip distal end 3601 relative to connector block proximal end 802. In one or more embodiments, a displacement of ultrasonic tip distal end 3601 relative to connector block proximal end 802 may be greater than a displacement of amplifier distal end 101 relative to connector block proximal end 802, e.g., ultrasonic tip 3600 may have a gain of greater than 1.0. Illustratively, a displacement of ultrasonic tip distal end 3601 relative to connector block proximal end 802 may be less than a displacement of amplifier distal end 101 relative to connector block proximal end 802, e.g., ultrasonic tip 3600 may have a gain of less than 1.0. In one or more embodiments, a displacement of ultrasonic tip distal end 3601 relative to connector block proximal end 802 may be equal to a displacement of amplifier distal end 101 relative to connector block proximal end 802, e.g., ultrasonic tip 3600 may have a gain equal to 1.0. Illustratively, ultrasonic tip 3600 may have a gain in a range of 7.5 to 14.0, e.g., ultrasonic tip 3600 may have a gain of 10.5. In one or more embodiments, ultrasonic tip 3600 may have a gain of less than 7.5 or greater than 14.0.

In one or more embodiments, angled adaptor 1300 may be configured to offset ultrasonic tip 3600 at an angle relative to amplifier 100, e.g., angled adaptor 1300 may be configured to offset ultrasonic tip 3600 at an angle relative to amplifier 100 to improve a surgeon's visualization of ultrasonic tip distal end 3601. Illustratively, angled adaptor 1300 may be configured to offset ultrasonic tip 3600 at an angle relative to amplifier 100 to improve a surgeon's line-of-sight while observing ultrasonic tip distal end 3601 through a microscope, e.g., angled adaptor 1300 may be configured to offset ultrasonic tip 3600 at an angle relative to amplifier 100 to improve a surgeon's line-of-sight while observing ultrasonic tip distal end 3601 through a cannula. In one or more embodiments, angled adaptor 1300 may be configured to offset ultrasonic tip 3600 at an angle relative to amplifier 100 wherein the angle is in a range of 5.0 to 25.0 degrees, e.g., angled adaptor 1300 may be configured to offset ultrasonic tip 3600 at an angle relative to amplifier 100 wherein the angle is 20.0 degrees. Illustratively, angled adaptor 1300 may be configured to offset ultrasonic tip 3600 at an angle relative to amplifier 100 wherein the angle is less than 5.0 degrees or greater than 25.0 degrees. In one or more embodiments, angled adaptor 1300 and ultrasonic tip 3600 may be configured to stabilize an instability caused by maintaining a standing wave through an angled portion of assembled ultrasonic handpiece 3800, e.g., angled tip interface 1330 may be disposed at or near an antinode of assembled ultrasonic handpiece 3800.

Illustratively, ultrasonic tip 3600 may be configured to receive the second half of the standing wave of assembled motor 2300. In one or more embodiments, ultrasonic tip 3600 may be configured to increase an amplitude of the second half of the standing wave of assembled motor 2300, e.g., ultrasonic tip 3600 may be configured to increase an amplitude of the second half of the standing wave of assembled motor 2300 by reducing a cross-sectional area of a portion of assembled ultrasonic handpiece 3800. Illustratively, ultrasonic tip chamfer 3620 may be configured to increase an amplitude of the second half of the standing wave of assembled motor 2300, e.g., ultrasonic tip chamfer 3620 may be configured to reduce a cross-sectional area of ultrasonic tip 3600. In one or more embodiments, ultrasonic tip fillet 3625 may be configured to increase an amplitude of the second half of the standing wave of assembled motor 2300, e.g., ultrasonic tip fillet 3625 may be configured to reduce a cross-sectional area of ultrasonic tip 3600. Illustratively, ultrasonic tip inner bore 3650 may be configured to increase an amplitude of the second half of the standing wave of assembled motor 2300, e.g., ultrasonic tip inner bore 3650 may be configured to reduce a cross-sectional area of ultrasonic tip 3600. In one or more embodiments, pre-aspiration port 3615 may be configured to increase an amplitude of the second half of the standing wave of assembled motor 2300, e.g., pre-aspiration port 3615 may be configured to reduce a cross-sectional area of ultrasonic tip 3600.

Illustratively, assembled ultrasonic handpiece 3800 may be configured to direct an irrigation fluid to ultrasonic tip 3600, e.g., assembled ultrasonic handpiece 3800 may be configured to direct an irrigation fluid to ultrasonic tip 3600 to prevent ultrasonic tip 3600 from overheating. In one or more embodiments, a portion of irrigation spike 3240 may be disposed in an irrigation fluid source, e.g., a portion of irrigation spike 3240 may be disposed in a saline bag. Illustratively, a pump of an ultrasonic surgical system may be configured to pump an irrigation fluid out from an irrigation fluid source, e.g., a pump of an ultrasonic surgical system may be configured to pump an irrigation fluid into a portion of irrigation spike 3240. In one or more embodiments, a pump of an ultrasonic surgical system may be configured to pump an irrigation fluid out from a portion of irrigation spike 3240, e.g., a pump of an ultrasonic surgical system may be configured to pump an irrigation fluid into irrigation tube 3220. Illustratively, a pump of an ultrasonic surgical system may be configured to pump an irrigation fluid out from irrigation tube 3220, e.g., a pump of an ultrasonic surgical system may be configured to pump an irrigation fluid into irrigation barb 1600. In one or more embodiments, a pump of an ultrasonic surgical system may be configured to pump an irrigation fluid out from irrigation barb 1600, e.g., a pump of an ultrasonic surgical system may be configured to pump an irrigation fluid into irrigation barb housing 851. Illustratively, a pump of an ultrasonic surgical system may be configured to pump an irrigation fluid out from irrigation barb housing 851, e.g., a pump of an ultrasonic surgical system may be configured to pump an irrigation fluid into conduit 805. In one or more embodiments, a pump of an ultrasonic surgical system may be configured to pump an irrigation fluid out from conduit 805, e.g., a pump of an ultrasonic surgical system may be configured to pump an irrigation fluid into a space between an outer diameter of transducer sleeve 1200 and an inner diameter of housing sleeve 2500. Illustratively, a pump of an ultrasonic surgical system may be configured to pump an irrigation fluid out from a space between an outer diameter of transducer sleeve 1200 and an inner diameter of housing sleeve 2500, e.g., a pump of an ultrasonic surgical system may be configured to pump an irrigation fluid into distal aperture 1225. In one or more embodiments, a pump of an ultrasonic surgical system may be configured to pump an irrigation fluid out from distal aperture 1225, e.g., a pump of an ultrasonic surgical system may be configured to pump an irrigation fluid into transducer sleeve housing 2446. Illustratively, a pump of an ultrasonic surgical system may be configured to pump an irrigation fluid out from transducer sleeve housing 2446, e.g., a pump of an ultrasonic surgical system may be configured to pump an irrigation fluid into nosecone proximal inner bore 2445. In one or more embodiments, a pump of an ultrasonic surgical system may be configured to pump an irrigation fluid out from nosecone proximal inner bore 2445, e.g., a pump of an ultrasonic surgical system may be configured to pump an irrigation fluid into nosecone distal inner bore 2440. Illustratively, a pump of an ultrasonic surgical system may be configured to pump an irrigation fluid out from nosecone distal inner bore 2440, e.g., a pump of an ultrasonic surgical system may be configured to pump an irrigation fluid into angled adaptor guide 2447. In one or more embodiments, a pump of an ultrasonic surgical system may be configured to pump an irrigation fluid out from angled adaptor guide 2447, e.g., a pump of an ultrasonic surgical system may be configured to pump an irrigation fluid into proximal irrigation sleeve proximal undercut 3421. Illustratively, a pump of an ultrasonic surgical system may be configured to pump an irrigation fluid out from proximal irrigation sleeve proximal undercut 3421, e.g., a pump of an ultrasonic surgical system may be configured to pump an irrigation fluid into proximal irrigation sleeve inner bore 3425. In one or more embodiments, a pump of an ultrasonic surgical system may be configured to pump an irrigation fluid out from proximal irrigation sleeve inner bore 3425, e.g., a pump of an ultrasonic surgical system may be configured to pump an irrigation fluid into proximal irrigation sleeve distal inner bore 3430. Illustratively, a pump of an ultrasonic surgical system may be configured to pump an irrigation fluid out from proximal irrigation sleeve distal inner bore 3430, e.g., a pump of an ultrasonic surgical system may be configured to pump an irrigation fluid into distal irrigation sleeve proximal inner bore 3542. In one or more embodiments, a pump of an ultrasonic surgical system may be configured to pump an irrigation fluid out from distal irrigation sleeve proximal inner bore 3542, e.g., a pump of an ultrasonic surgical system may be configured to pump an irrigation fluid into distal irrigation sleeve inner bore 3540. Illustratively, a pump of an ultrasonic surgical system may be configured to pump an irrigation fluid out from distal irrigation sleeve inner bore 3540, e.g., a pump of an ultrasonic surgical system may be configured to pump an irrigation fluid into distal irrigation sleeve distal inner bore 3541. In one or more embodiments, pumping an irrigation fluid into distal irrigation sleeve distal inner bore 3541 may be configured to direct an irrigation fluid to ultrasonic tip 3600 to prevent ultrasonic tip 3600 from overheating.

Illustratively, assembled ultrasonic handpiece 3800 may be configured to remove an irrigation fluid from a surgical site, e.g., assembled ultrasonic handpiece 3800 may be configured to remove tissue or bone from a surgical site. In one or more embodiments, a pump of an ultrasonic surgical system may be configured to pump an irrigation fluid out from a surgical site, e.g., a pump of an ultrasonic surgical system may be configured to pump an irrigation fluid out from distal irrigation sleeve 3500. Illustratively, a pump of an ultrasonic surgical system may be configured to pump an irrigation fluid out from distal irrigation sleeve distal inner bore 3541, e.g., a pump of an ultrasonic surgical system may be configured to pump an irrigation fluid into ultrasonic tip inner bore 3650. In one or more embodiments, a pump of an ultrasonic surgical system may be configured to pump an irrigation fluid out from ultrasonic tip inner bore 3650, e.g., a pump of an ultrasonic surgical system may be configured to pump an irrigation fluid into angled adaptor temporary housing 3646. Illustratively, a pump of an ultrasonic surgical system may be configured to pump an irrigation fluid out from angled adaptor temporary housing 3646, e.g., a pump of an ultrasonic surgical system may be configured to pump an irrigation fluid into angled inner bore distal bevel 1365. In one or more embodiments, a pump of an ultrasonic surgical system may be configured to pump an irrigation fluid out from angled inner bore distal bevel 1365, e.g., a pump of an ultrasonic surgical system may be configured to pump an irrigation fluid into angled inner bore 1360. Illustratively, a pump of an ultrasonic surgical system may be configured to pump an irrigation fluid out from angled inner bore 1360, e.g., a pump of an ultrasonic surgical system may be configured to pump an irrigation fluid into medial inner bore 1350. In one or more embodiments, a pump of an ultrasonic surgical system may be configured to pump an irrigation fluid out from medial inner bore 1350, e.g., a pump of an ultrasonic surgical system may be configured to pump an irrigation fluid into medial inner bore proximal bevel 1355. Illustratively, a pump of an ultrasonic surgical system may be configured to pump an irrigation fluid out from medial inner bore proximal bevel 1355, e.g., a pump of an ultrasonic surgical system may be configured to pump an irrigation fluid into amplifier distal undercut 135. In one or more embodiments, a pump of an ultrasonic surgical system may be configured to pump an irrigation fluid out from amplifier distal undercut 135, e.g., a pump of an ultrasonic surgical system may be configured to pump an irrigation fluid into amplifier inner bore 130. Illustratively, a pump of an ultrasonic surgical system may be configured to pump an irrigation fluid out from amplifier inner bore 130, e.g., a pump of an ultrasonic surgical system may be configured to pump an irrigation fluid into amplifier housing 833. In one or more embodiments, a pump of an ultrasonic surgical system may be configured to pump an irrigation fluid out from amplifier housing 833, e.g., a pump of an ultrasonic surgical system may be configured to pump an irrigation fluid into amplifier housing taper 834. Illustratively, a pump of an ultrasonic surgical system may be configured to pump an irrigation fluid out from amplifier housing taper 834, e.g., a pump of an ultrasonic surgical system may be configured to pump an irrigation fluid into connector block inner bore 830. In one or more embodiments, a pump of an ultrasonic surgical system may be configured to pump an irrigation fluid out from connector block inner bore 830, e.g., a pump of an ultrasonic surgical system may be configured to pump an irrigation fluid into aspiration barb housing taper 838. Illustratively, a pump of an ultrasonic surgical system may be configured to pump an irrigation fluid out from aspiration barb housing taper 838, e.g., a pump of an ultrasonic surgical system may be configured to pump an irrigation fluid into aspiration barb housing 837. In one or more embodiments, a pump of an ultrasonic surgical system may be configured to pump an irrigation fluid out from aspiration barb housing 837, e.g., a pump of an ultrasonic surgical system may be configured to pump an irrigation fluid into aspiration barb 1700. Illustratively, a pump of an ultrasonic surgical system may be configured to pump an irrigation fluid out from aspiration barb 1700, e.g., a pump of an ultrasonic surgical system may be configured to pump an irrigation fluid into aspiration tube 3210. In one or more embodiments, a pump of an ultrasonic surgical system may be configured to pump an irrigation fluid out from aspiration tube 3210, e.g., a pump of an ultrasonic surgical system may be configured to pump an irrigation fluid into canister connector 3230. Illustratively, a pump of an ultrasonic surgical system may be configured to pump an irrigation fluid out from canister connector 3230, e.g., a pump of an ultrasonic surgical system may be configured to pump an irrigation fluid into a suction canister for disposal.

In one or more embodiments, angled adaptor 1300 may be substituted with a straight adaptor, e.g., the second half of the standing wave of assembled motor 2300 may not be maintained through an angled portion of assembled ultrasonic handpiece 3800. Illustratively, ultrasonic tip 3600 may be connected directly or indirectly to amplifier 100, e.g., ultrasonic tip proximal end 3602 may be adjacent to amplifier distal end 101. In one or more embodiments, ultrasonic tip proximal end 3602 may abut amplifier distal end 101. Illustratively, ultrasonic tip 3600 may be connected to amplifier 100 wherein a portion of ultrasonic tip 3600 is fixed to a portion of amplifier 100 by any suitable fixation means, e.g., the portion of ultrasonic tip 3600 may be fixed to the portion of amplifier 100 by force of friction, an interference fit, a weld, an adhesive, and epoxy, a crimp, a tie, a pin, etc.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A surgical instrument comprising:
   an ultrasonic handpiece having an ultrasonic handpiece distal end and an ultrasonic handpiece proximal end;
   a transducer of the ultrasonic handpiece having a transducer distal end and a transducer proximal end;
   an amplifier of the transducer having an amplifier distal end and an amplifier proximal end; and
   an ultrasonic tip having an ultrasonic tip distal end, an ultrasonic tip proximal end, an ultrasonic tip overall length, an ultrasonic tip minimum outer diameter, and an ultrasonic tip maximum outer diameter wherein the ultrasonic tip proximal end is connected directly or indirectly to the amplifier distal end and wherein the ultrasonic tip has a maximum oscillation amplitude of greater than about 444.5 micrometers and wherein the ultrasonic handpiece is configured to maintain the maximum oscillation amplitude for at least about 40 seconds.

2. The surgical instrument of claim 1 wherein the maximum oscillation amplitude is at least about 0.400 percent of the ultrasonic tip overall length.

3. The surgical instrument of claim 1 wherein the maximum oscillation amplitude is at least about 16.990 percent of the ultrasonic tip minimum outer diameter.

4. The surgical instrument of claim 1 wherein the maximum oscillation amplitude is at least about 5.556 percent of the ultrasonic tip maximum outer diameter.

5. The surgical instrument of claim 1 further comprising a pre-aspiration port of the ultrasonic tip.

6. The surgical instrument of claim 1 further comprising an irrigation sleeve having an irrigation sleeve distal end and an irrigation sleeve proximal end wherein the irrigation sleeve is configured to direct an irrigation fluid to the ultrasonic tip.

7. The surgical instrument of claim 1 further comprising an antinode step of the amplifier.

8. The surgical instrument of claim 1 further comprising a piezoelectric ring of the transducer.

9. The surgical instrument of claim 1 further comprising an outer electrode stack of the transducer.

10. The surgical instrument of claim 9 further comprising an inner electrode stack of the transducer.

11. The surgical instrument of claim 1 further comprising an amplifier sleeve having an amplifier sleeve distal end and an amplifier sleeve proximal end wherein the amplifier sleeve is disposed over a portion of the amplifier.

12. The surgical instrument of claim 1 further comprising a flange having a flange distal end and a flange proximal end wherein the flange is disposed over a portion of the amplifier.

13. The surgical instrument of claim 1 further comprising an inert ring of the transducer having an inert ring distal end and an inert ring proximal end.

14. The surgical instrument of claim 1 further comprising a connector block of the transducer having a connector block distal end and a connector block proximal end.

15. The surgical instrument of claim 1 further comprising an irrigation barb of the ultrasonic handpiece having an irrigation barb distal end and an irrigation barb proximal end.

16. The surgical instrument of claim 1 further comprising an aspiration barb of the ultrasonic handpiece having an aspiration barb distal end and an aspiration barb proximal end.

17. The surgical instrument of claim 1 further comprising a transducer sleeve of the ultrasonic handpiece having a transducer sleeve distal end and a transducer sleeve proximal end wherein the transducer sleeve is disposed over a portion of the transducer.

18. The surgical instrument of claim 17 further comprising a distal aperture of the transducer sleeve.

19. The surgical instrument of claim 17 further comprising a nosecone interface of the transducer sleeve.

20. The surgical instrument of claim 17 further comprising a nosecone mount of the transducer sleeve.

\* \* \* \* \*